(12) United States Patent
Heid et al.

(10) Patent No.: US 9,364,829 B2
(45) Date of Patent: Jun. 14, 2016

(54) ANALYSIS USING MICROFLUIDIC PARTITIONING DEVICES

(75) Inventors: Christian A. Heid, Redwood City, CA (US); Antoine Daridon, Mont-sur-Rolle (CH)

(73) Assignee: FLUIDIGM CORPORATION, South San Francisco, CA (US)

( * ) Notice: Subject to any disclaimer, the term of this patent is extended or adjusted under 35 U.S.C. 154(b) by 244 days.

(21) Appl. No.: 12/945,483

(22) Filed: Nov. 12, 2010

(65) Prior Publication Data

US 2011/0129841 A1 Jun. 2, 2011

Related U.S. Application Data

(63) Continuation of application No. 11/916,025, filed as application No. PCT/US2006/021416 on Jun. 2, 2006.

(60) Provisional application No. 60/687,010, filed on Jun. 2, 2005.

(51) Int. Cl.
| | |
|---|---|
| *B01L 3/00* | (2006.01) |
| *C12Q 1/68* | (2006.01) |
| *B01L 7/00* | (2006.01) |

(52) U.S. Cl.
CPC ............ *B01L 3/5027* (2013.01); *C12Q 1/686* (2013.01); *B01L 7/52* (2013.01); *B01L 2300/0864* (2013.01); *B01L 2300/0867* (2013.01); *B01L 2300/0874* (2013.01); *B01L 2400/0487* (2013.01); *B01L 2400/0655* (2013.01)

(58) Field of Classification Search
CPC ............ C12Q 1/686; C12Q 2525/155; C12Q 2525/301; B01L 2300/0864; B01L 2300/0867; B01L 2300/0874; B01L 2400/0487; B01L 2400/0655; B01L 3/5027; B01L 7/52
See application file for complete search history.

(56) References Cited

U.S. PATENT DOCUMENTS

| | | | |
|---|---|---|---|
| 4,508,625 A | 4/1985 | Graham | |
| 4,822,733 A | 4/1989 | Morrison | |
| 5,272,081 A * | 12/1993 | Weinreb et al. | ............... 435/29 |
| 5,300,779 A | 4/1994 | Hillman et al. | |
| 5,556,773 A | 9/1996 | Yourno | |
| 5,622,821 A | 4/1997 | Selvin et al. | |
| 5,639,615 A | 6/1997 | Selvin et al. | |
| 5,641,628 A | 6/1997 | Bianchi | |
| 5,656,433 A | 8/1997 | Selvin et al. | |
| 5,723,591 A | 3/1998 | Livak et al. | |
| 5,750,339 A | 5/1998 | Smith | |
| 5,840,502 A | 11/1998 | Van Vlasselaer | |
| 5,879,883 A | 3/1999 | Benson et al. | |
| 5,932,415 A | 8/1999 | Schubert et al. | |
| 5,945,283 A | 8/1999 | Kwok et al. | |
| 6,013,435 A | 1/2000 | Nusbaum | |
| 6,045,993 A | 4/2000 | Mahony et al. | |
| 6,100,029 A | 8/2000 | Lapidus et al. | |
| 6,143,496 A | 11/2000 | Brown et al. | |
| 6,154,707 A | 11/2000 | Livak et al. | |
| 6,159,685 A | 12/2000 | Pinkel et al. | |
| 6,214,558 B1 | 4/2001 | Shuber et al. | |
| 6,225,094 B1 | 5/2001 | Ludwig et al. | |
| 6,251,639 B1 | 6/2001 | Kurn | |
| 6,258,540 B1 | 7/2001 | Lo et al. | |
| 6,300,077 B1 | 10/2001 | Shuber et al. | |
| 6,368,871 B1 | 4/2002 | Christel et al. | |
| 6,387,652 B1 | 5/2002 | Haugland et al. | |
| 6,391,559 B1 | 5/2002 | Brown et al. | |
| 6,408,878 B2 | 6/2002 | Unger et al. | |
| 6,432,630 B1 | 8/2002 | Blankenstein | |
| 6,440,706 B1 | 8/2002 | Vogelstein et al. | |
| 6,503,722 B1 | 1/2003 | Valkirs | |
| 6,511,967 B1 | 1/2003 | Weissleder et al. | |
| 6,618,679 B2 | 9/2003 | Loehrlein et al. | |
| 6,632,642 B1 | 10/2003 | Motoyama et al. | |
| 6,706,471 B1 | 3/2004 | Brow et al. | |
| 6,723,505 B1 | 4/2004 | Karlsen | |
| 6,753,147 B2 | 6/2004 | Vogelstein et al. | |
| 6,783,928 B2 | 8/2004 | Hvichia et al. | |
| 6,927,028 B2 | 8/2005 | Dennis et al. | |
| 6,960,437 B2 | 11/2005 | Enzelberger et al. | |
| 7,442,506 B2 | 10/2008 | Dhallan | |
| 7,476,363 B2 | 1/2009 | Unger et al. | |
| 7,887,753 B2 | 2/2011 | Quake et al. | |
| 8,628,923 B2 | 1/2014 | Hamilton et al. | |

(Continued)

FOREIGN PATENT DOCUMENTS

| | | |
|---|---|---|
| WO | 9116452 A1 | 10/1991 |
| WO | 9722719 A1 | 6/1997 |

(Continued)

OTHER PUBLICATIONS

Leary, J. F. et al., SPIE, vol. 3603, pp. 93-101 (1999).*
Picot, J. et al., Cytotechnol., vol. 64, pp. 109-130 (2012).*
Gross, H-J. et al., PNAS USA, vol. 92, pp. 537-541 (1995).*
Beitsch, P.D. et al., Am. J. Surg., vol. 180, pp. 446-449 (2000).*
Thorsen, T. et al., Science, vol. 298, pp. 580-584 (2002).*
Wang, M.M. et al., Nature Biotechnol., vol. 23, pp. 83-87 (Jan. 2005).*
White, A.K. et al., PNAS USA, vol. 108, pp. 13999-14004 (2011).*
Thompson, A.M. et al., Lab on a Chip, vol. 14, pp. 3135-3142 (2014).*

(Continued)

*Primary Examiner* — Teresa E Strzelecka
(74) *Attorney, Agent, or Firm* — Emily M. Haliday; Weaver Austin Villeneuve & Sampson LLP

(57) ABSTRACT

The invention relates to methods, reagents and devices for detection and characterization of nucleic acids, cells, and other biological samples. Assay method are provided in which a sample is partitioned into sub-samples, and analysis of the contents of the sub-samples carried out. The invention also provides microfluidic devices for conducting the assay. The invention also provides an analysis method using a universal primers and probes for amplification and detection.

22 Claims, 7 Drawing Sheets

(56) References Cited

U.S. PATENT DOCUMENTS

| | | |
|---|---|---|
| 2002/0064779 A1 | 5/2002 | Landegren et al. |
| 2002/0160404 A1 | 10/2002 | Dietmaier et al. |
| 2002/0166760 A1 | 11/2002 | Prentiss et al. |
| 2003/0017591 A1 | 1/2003 | Kurn |
| 2003/0022207 A1 | 1/2003 | Balasubramanian et al. |
| 2003/0033091 A1 | 2/2003 | Opalsky et al. |
| 2003/0138829 A1* | 7/2003 | Unger et al. ............... 435/6 |
| 2003/0180715 A1 | 9/2003 | Kemp et al. |
| 2003/0204331 A1 | 10/2003 | Whitney et al. |
| 2003/0228613 A1 | 12/2003 | Bornarth et al. |
| 2004/0005582 A1 | 1/2004 | Shipwash |
| 2004/0037470 A1 | 2/2004 | Simske |
| 2004/0048360 A1 | 3/2004 | Wada |
| 2004/0053352 A1 | 3/2004 | Ouyang |
| 2004/0096892 A1 | 5/2004 | Wang et al. |
| 2004/0110166 A1 | 6/2004 | Macevicz |
| 2004/0137470 A1 | 7/2004 | Dhallan |
| 2004/0142463 A1 | 7/2004 | Walker |
| 2004/0144651 A1 | 7/2004 | Huang |
| 2004/0185495 A1 | 9/2004 | Schueler et al. |
| 2004/0203037 A1 | 10/2004 | Lo et al. |
| 2004/0229349 A1 | 11/2004 | Daridon |
| 2005/0019792 A1 | 1/2005 | McBride et al. |
| 2005/0049793 A1 | 3/2005 | Paterlini-Brechot |
| 2005/0072946 A1 | 4/2005 | Studer et al. |
| 2005/0129581 A1 | 6/2005 | McBride et al. |
| 2005/0145496 A1 | 7/2005 | Goodsaid et al. |
| 2005/0158754 A1 | 7/2005 | Puffenberger et al. |
| 2005/0164241 A1 | 7/2005 | Hahn et al. |
| 2005/0221341 A1 | 10/2005 | Shimkets |
| 2005/0221373 A1 | 10/2005 | Enzelberger et al. |
| 2005/0250111 A1 | 11/2005 | Xie |
| 2005/0252773 A1 | 11/2005 | McBride et al. |
| 2005/0287611 A1 | 12/2005 | Nugent, IV et al. |
| 2006/0000772 A1 | 1/2006 | Sano |
| 2006/0046258 A1 | 3/2006 | Lapidus et al. |
| 2006/0051265 A1 | 3/2006 | Mohamed |
| 2006/0051775 A1 | 3/2006 | Bianchi |
| 2006/0053503 A1 | 3/2006 | Culiat et al. |
| 2006/0073125 A1 | 4/2006 | Clarke et al. |
| 2006/0121452 A1 | 6/2006 | Dhallan |
| 2006/0141518 A1 | 6/2006 | Lao et al. |
| 2006/0223178 A1 | 10/2006 | Barber |
| 2006/0252068 A1 | 11/2006 | Lo |
| 2006/0252071 A1 | 11/2006 | Lo |
| 2007/0059680 A1 | 3/2007 | Kapur |
| 2007/0059683 A1 | 3/2007 | Barber |
| 2007/0059716 A1 | 3/2007 | Balis |
| 2007/0059719 A1 | 3/2007 | Grisham |
| 2007/0059774 A1 | 3/2007 | Grisham |
| 2007/0059781 A1 | 3/2007 | Kapur |
| 2007/0072290 A1 | 3/2007 | Hvichia |
| 2007/0202525 A1 | 8/2007 | Quake et al. |
| 2007/0207466 A1 | 9/2007 | Cantor |
| 2008/0020390 A1 | 1/2008 | Mitchell |
| 2008/0023399 A1 | 1/2008 | Inglis |
| 2008/0026390 A1 | 1/2008 | Stoughton |
| 2008/0038733 A1 | 2/2008 | Bischoff |
| 2008/0050739 A1 | 2/2008 | Stoughton |
| 2008/0070792 A1 | 3/2008 | Stoughton |
| 2008/0071076 A1 | 3/2008 | Hahn |
| 2008/0090239 A1 | 4/2008 | Shoemaker |
| 2008/0096766 A1 | 4/2008 | Lee |
| 2008/0108063 A1 | 5/2008 | Lucero et al. |
| 2008/0138809 A1 | 6/2008 | Kapur |
| 2008/0153090 A1 | 6/2008 | Lo |
| 2008/0182261 A1 | 7/2008 | Bianchi |
| 2008/0220422 A1 | 9/2008 | Shoemaker et al. |
| 2008/0223721 A1 | 9/2008 | Cohen et al. |
| 2009/0029377 A1 | 1/2009 | Lo et al. |
| 2009/0053719 A1 | 2/2009 | Lo et al. |
| 2009/0087847 A1 | 4/2009 | Lo et al. |
| 2009/0170113 A1 | 7/2009 | Quake et al. |
| 2009/0170114 A1 | 7/2009 | Quake et al. |
| 2009/0257920 A1 | 10/2009 | Facer et al. |
| 2009/0317798 A1 | 12/2009 | Heid et al. |
| 2010/0120077 A1 | 5/2010 | Daridon |
| 2010/0178655 A1 | 7/2010 | Hamilton et al. |
| 2010/0203538 A1 | 8/2010 | Dube et al. |
| 2010/0273219 A1 | 10/2010 | May et al. |
| 2011/0143949 A1 | 6/2011 | Heid et al. |
| 2011/0257039 A1 | 10/2011 | Wang et al. |
| 2014/0193812 A1 | 7/2014 | Hamilton et al. |

FOREIGN PATENT DOCUMENTS

| | | |
|---|---|---|
| WO | 9802528 A1 | 1/1998 |
| WO | 9839474 A1 | 9/1998 |
| WO | WO 98/47003 | 10/1998 |
| WO | 0101025 A2 | 1/2001 |
| WO | 0212896 A1 | 2/2002 |
| WO | WO 02/40874 * | 5/2002 |
| WO | WO02/40874 A1 * | 5/2002 |
| WO | 0243615 A2 | 6/2002 |
| WO | 02072772 A2 | 9/2002 |
| WO | 03048295 A1 | 6/2003 |
| WO | WO 03/085379 | 10/2003 |
| WO | WO 04/000721 | 12/2003 |
| WO | 2004029221 A2 | 4/2004 |
| WO | 2004029221 A3 | 4/2004 |
| WO | 2004088310 A1 | 10/2004 |
| WO | 2004089810 A2 | 10/2004 |
| WO | 2004113877 A1 | 12/2004 |
| WO | 2005023091 A2 | 3/2005 |
| WO | 2005023091 A3 | 3/2005 |
| WO | 2005030822 A2 | 4/2005 |
| WO | 2005084191 A2 | 9/2005 |
| WO | 2007044091 A2 | 4/2007 |
| WO | 2007044091 A3 | 4/2007 |
| WO | 2009013492 A1 | 1/2009 |
| WO | 2009013496 A1 | 1/2009 |
| WO | 2009019455 A2 | 2/2009 |
| WO | WO 2010/083250 | 7/2010 |

OTHER PUBLICATIONS

Adams et al., "Increase of Circulating Endothelial Progenitor Cells in Patients With Coronary Artery Disease After Exercise-Induced Ischemia," Arterioscler. Thromb. Vasc. Biol., pp. 1-8, 2004.

Akimitsu et al., "Enforced cytokinesis without complete nuclear division in embryonic cells depleting the activity of DNA topoisomerase IIalpha," Genes to Cells, 8:393-402, 2003.

Amirlak and Couldwell, "Apoptosis in glioma cells: review and analysis of techniques used for study with focus on the laser scanning cytometer," J. Neuro-Oncol., 63:129-45, 2003.

Anderson and Young, "Chapter 4: Quantitative Filter Hybridisation," Nucleic Acid Hybridisation, pp. 73-111, 1985.

Klein et al., "Discovery and analysis of differentially expressed genes in single cells and cell populations," Current Protocols in Molecular Biology, Greene Publishing and Wiley-Interscience, New York; Chapter 25:25.0.1-25B.8.18, 2009.

Awais et al., "A genetically encoded fluorescent indicator capable of discriminating estrogen agonists from antagonists in living cells," Anal Chem., 76:2181-6, 2004.

Balaji et al., "Live cell ultraviolet microscopy: a comparison between two- and three-photon excitation," Microsc. Res. Tech., 63:67-71, 2004.

Balmer et al., "Elevated methyl-CpG-binding protein 2 expression is acquired during postnatal human brain development and is correlated with alternative polyadenylation," J. Mol. Med., 81:61-8, 2002.

Baskin et al., "Thimerosal Induces DNA Breaks, Caspase-3 Activation, Membrane Damage, and Cell Death in Cultured Human Neurons and Fibroblasts," Toxicol. Sci., 74:361-368, 2003.

Beliakoff et al., "Hormone-Refractory Breast Cancer Remains Sensitive to the Antitumor Activity of Heat Shock Protein 90 Inhibitors," Clin. Cancer Res., 9:4961-71, 2003.

Bocsi et al., "Scanning fluorescent microscopy analysis is applicable for absolute and relative cell frequency determinations," Cytometry, 61A:1-8, 2004.

Bollmann et al., "Determination of features indicating progression in atypical squamous cells with undetermined significance," Cancer, 99:113-7, 2003.

(56) References Cited

OTHER PUBLICATIONS

Bollmann, et al., "Human papillomavirus typing and DNA ploidy determination of squamous intraepithelial lesions in liquid-based cytologic samples," Cancer, 99:57-62, 2003.
Braunschweig et al., "X-chromosome inactivation ratios affect wild-type MeCP2 expression within mosaic Rett syndrome and Mecp2-I+ mouse brain," Hum. Mol. Genet., 13(12):1275-86, 2004.
Brower, "Evidence of efficacy: researchers investigating markers for angiogenesis inhibitors," J. Natl. Cancer. Inst., 95 (19):1425-27, 2003.
Cai et al., "Toxicity of Acetaminophen, Salicylic Acid, and Caffeine for First-Passage Rat Renal Inner Medullary Collecting Duct Cells," J. Phannacol. Exp. Ther., 306:35-42, 2003.
Cheng et al, "Immunocytochemical analysis of prostate stem cell antigen as adjunct marker for detection of urothelial transitional cell carcinoma in voided urine specimens," J. Urol., 169:2094-100, 2003.
Chigaev et al., "Conformational regulation of alpha4beta1-integrin affinity by reducing agents. 'Inside-out' signaling is independent of and additive to reduction-regulated integrin activation," J. Biol. Chem., 279(31):32435-43, 2004.
Chou, et al., "Integrated Elastomer Fluidic Lab-on-a-chip-Surface Patterning and DNA Diagnostics," in Proceedings of the Solid State Actuator and Sensor Workshop, Hilton Head, S.C., 4 pages, 2000.
Chung et al., "Tea and Cancer Prevention: Studies in Animals and Humans," J. Nutr., 133:3268S-3274S, 2003.
Claytor et al., "The cleaved peptide of PAR1 is a more potent stimulant of platelet-endothelial cell adhesion than is thrombin," J. Vasc. Surg., 37:440-5, 2003.
Crowder et al., "PML mediates IFN-alpha-induced apoptosis in myeloma by regulating TRAIL induction," Blood, 105 (3):1280-87, 2005.
Cummins et al., "Persistent Localization of Activated Extracellular Signal-Regulated Kinases (ERK1/2) is Epithelial Cell-Specific in an Inhalation Model of Asbestosis," Am. J. Pathol., 162(3):713-20, 2003.
D'Amico et al., "The Role of Ink4(alpha)/Arf in ErbB2 Mammary Gland Tumorigenesis," Cancer Res., 63:3395-3402, 2003.
Davis et al., "Automated quantification of apoptosis after neoadjuvant chemotherapy for breast cancer: early assessment predicts clinical response," Clin. Cancer Res., 9:955-60, 2003.
Davis et al., "Surrogate markers in antiangiogenesis clinical trials," Br. J. Cancer, 89:8-14, 2003.
Davis et al., "Antiangiogenic tumor therapy," BioTechniques, 34(4):1048-63, 2003.
Davis et al., "Quantitative Analysis of Biomarkers Defines an Optimal Biological Dose for Recombinant Human Endostatin in Primary Human Tumors," Clin. Cancer Res., 10:33-42, 2004.
Denmeade et al., "Prostate-Specific Antigen Activated Thapsigargin Prodrug as Targeted Therapy for Prostate Cancer," J Natl Cancer Inst., 95(13):990-1000, 2003.
Di Pinto et al., A collagenase-targeted multiplex PCR assay for identification of Vibrio alginolyticus, Vibrio cholerae, and Vibrio parahaemolyticus, J. Food Prot., 68(1):150-3, 2005.
Dirks et al., "Visualizing RNA molecules inside the nucleus of living cells," Methods, 29:51-7, 2003.
Dmitrieva et al., "High NaCl causes Mre11 to leave the nucleus, disrupting DNA damage signaling and repair, Am. J. Physiol. Renal. Physiol.," 285:F266-74, 2003.
Dmitrieva et al., "Cells adapted to high NaCl have many DNA breaks and impaired DNA repair both in cell culture and in vivo," PNAS, 101(8):2317-22, 2004.
Doyle et al., "Toll-like Receptors Induce a Phagocytic Gene Program through p38," J. Exp. Med., 199(1):81-90, 2004.
Fortunel et al., "Long-term expansion of human functional epidermal precursor cells: promotion of extensive amplification by low TGF-beta1 concentrations," J. Cell Sci., 116:4043-52, 2003.
Foster et al., "Laser scanning cytometry for the detection of neoplasia in urologic cytology specimens," Cancer, 102:115-23, 2004.
Fredriksson et al., Protein detection using proximity-dependent DNA ligation assays, Nat. Biotech., 20:473-7, 2002.
Furuta et al., "Phosphorylation of Histone H2AX and Activation of Mre11, Rad50, and Nbsl in Response to Replication-dependent DNA Double-strand Breaks Induced by Mammalian DNA Topoisomerase I Cleavage Complexes," J. Biol. Chem., 278(22):20303-12, 2003.
Furuya et al., "A Novel Technology Allowing Immunohistochemical Staining of a Tissue Section with 50 Different Antibodies in a Single Experiment," J. Histochem. Cytochem., 52(2):205-10, 2004.
Gardiner, "Spatial and temporal analysis of Rac activation during live neutrophil chemotaxis," Curr. Biol., 12:2029-34, 2002.
Gerstner et al, "Eosinophilia in nasal polyposis: its objective quantification and clinical relevance," Clin. Exp. Allergy, 34:65-70, 2004.
Gerstner et al., "Analysis of ploidy in hypopharyngeal cancer by laser scanning cytometry on fine needle aspirate biopsies," Anal. Cell. Pathol., 25:51-62, 2003.
Gerstner et al., "Slide-based cytometry for predicting malignancy in solid salivary gland tumors by fine needle aspirate biopsies," Cytometry, 53B:20-5, 2003.
Gerstner et al., "Quantitative histology by multicolor slide-based cytometry," Cytometry, 59A:210-9, 2004.
Gniadecki, and Bang, "Flotillas of Lipid Rafts in Transit Amplifying Cell-Like Keratinocytes," J. Invest. Dermatol., 121:522-28, 2003.
Gniadecki and Rossen, "Expression of T-cell activation marker CD134 (0X40) in lymphomatoid papulosis," Br. J. Dermatol., 148:885-91, 2003.
Greene et al., "Secretory Leucoprotease Inhibitor Impairs Toll-Like Receptor 2- and 4-Mediated Responses in Monocytic Cells," Infect. Immun., 72(6):3684-87, 2004.
Griffin et al., "Neutrophil elastase up-regulates human beta-defensin-2 expression in human bronchial epithelial cells," FEBS Lett., 546:233-6, 2003.
Guatelli et al., "Isothermal, in vitro amplification of nucleic acids by a multienzyme reaction modeled after retrorvial replication," Proc. Nat. Acad. Sci. USA, 87:1874-78, 1990.
Gui and Zheng, "Epidermal Growth Factor Induction of Phenotype-dependent Cell Cycle Arrest in Vascular Smooth Muscle Cells is through the Mitogen-activated Protein Kinase Pathway," J. Biol. Chem., 278(52):53017-25, 2003.
Gullberg et al., "Cytokine detection by antibody-based proximity ligation," Proc. Natl. Acad. Sci. USA, 101(22):8420-4, 2004.
Haider et al., "Dual Functionality of Cyclooxygenase-2 as a Regulator of Tumor Necrosis Factor-Mediated G1 Shortening and Nitric Oxide-Mediated Inhibition of Vascular Smooth Muscle Cell Proliferation," Circulation, 108:1015-21, 2003.
Haider et al., "In vitro model of 'wound healing' analyzed by laser scanning cytometry: Accelerated healing of epithelial cell monolayers in the presence of hyaluronate," Cytometry, 53A:1-8, 2003.
Heitmann et al., "Solution structure of the matrix attachment region-binding domain of chicken MeCP2," Eur. J. Biochem., 270:3263-70, 2003.
Hennerbichler et al., "Fetal nucleated red blood cells in peripheral blood of pregnant women: detection and determination of location on a slide using laser-scanning cytometry," Prenat. Diagn., 23:710-5, 2003.
Heymach et al., "Phase II study of the antiangiogenic agent SU5416 in patients with advanced soft tissue sarcomas," Clin. Cancer Res., 10:5732-40, 2004.
Hirabayashi et al., "The Wnt/beta-catenin pathway directs neuronal differentiation of cortical neural precursor cells," Development, 131:2791-801, 2004.
Huang et al., "Histone H2AX phosphorylation induced by selective photolysis of BrdU-labeled DNA with UV light: Relation to cell cycle phase," Cytometry, 62A:1-7, 2004.
Huang et al., "Assessment of histone H2AX phosphorylation induced by DNA topoisomerase I and II inhibitors topotecan and mitoxantrone and by the DNA cross-linking agent cisplatin," Cytometry, 58A:99-110, 2004.
Huang et al., "DNA Damage Induced by DNA Topoisomerase I- and Topoisomerase II-Inhibitors Detected by Histone H2AX phosphorylation in Relation to the Cell Cycle Phase and Apoptosis," Cell Cycle, 2:614-9, 2003.

(56) References Cited

OTHER PUBLICATIONS

Huletsky et al., "New real-time PCR assay for rapid detection of methicillin-resistant Staphylococcus aureus directly from specimens containing a mixture of staphylococci." J. Clin. Microbiol., 42(5):1875-84, 2004.

Isaka et al., "Chromosomal Variations Within Aneuploid Cancer Lines," J. Histochem. Cytochem., 51(10):1343-53, 2003.

Johnson et al., "Aluminum-Maltolate Induces Apoptosis and Necrosis in Neuro-2a Cells: Potential Role for p53 Signaling," Toxicol. Sci., 83(2):329-39, 2005.

Kamat et al., "The proteasome inhibitor bortezomib synergizes with gemcitabine to block the growth of human 253JB-V bladder tumors in vivo," Mol. Cancer Ther., 3(3):279-90, 2004.

Kang et al., "Analysis of tyrosine phosphorylation in resident peritoneal cells during diet restriction by laser scanning cytometry," Shock, 19(3):238-44, 2003.

Kang et al., "Brief refeeding rapidly reverses dietary restriction-induced nuclear factor-kappaB downregulation in peritoneal resident cells," J. Parenter. Enteral Nutr, 27(3):193-7, 2003.

Kawamura et al., "Centrosome hyperamplification and chromosomal instability in bladder cancer," Eur. Urol. 43:505-15, 2003.

Kawasaki et al., "11q23-24 loss is associated with chromosomal instability in endometrial cancer," Int. J. Mol. Med., 12:727-31, 2003.

Kobie et al., "Transforming Growth Factor (beta) Inhibits the Antigen-Presenting Functions and Antitumor Activity of Dendritic Cell Vaccines," Cancer Res., 63:1860-64, 2003.

Kolek et al., "Antiproliferative and apoptotic effect of TGF-beta1 in bovine mammary epithelial BME-UV1 cells," Comp. Biochem. Physiol. Part C, 134:417-30, 2003.

Kolek et al., "Co-localization of apoptosis-regulating proteins in mouse mammary epithelial 1-1C11 cells exposed to TGF-beta1," Eur. J. Cell Biol., 82:303-12, 2003.

Koup et al., "Limiting dilution analysis of cytotoxic T lymphocytes to human immunodeficiency virus gag antigens in infected persons: in vitro quantitation of effector cell populations with p17 and p24 specificities" J. Exp. Med., 174:1593-600, 1991.

Kranc et al., "Transcriptional Coactivator Cited2 Induces Bmi1 and Me118 and Controls Fibroblast Proliferation via Ink4a/AFR," Mol. Cell. Biol., 23(21):7658-66, 2003.

Kriaucionis and Bird, "DNA methylation and Rett syndrome," Hum. Mol. Genet., 12(2):R221-27, 2003.

Kulkarni et al., "Micropatterning of endothelial cells by guided stimulation with angiogenic factors," Biosens. Bioelectron., 19:1401-7, 2004.

Kwoh et al., "Transcription-based amplification system and detection of amplified human immunodeficiency virus type 1 with a bead-based sandwich hybridization format," Proc. Natl. Acad. Sci. USA, 86:1173-77, 1989.

Lamas et al., "Quantitative Fluorescence Imaging Approach for the Study of Polyploidization in Hepatocytes," J. Histochem. Cytochem., 51(3):319-30, 2003.

Landegren et al., "Molecular tools for a molecular medicine: analyzing genes, transcripts and proteins using padlock and proximity probes," J. Mol. Recognit., 17:194-7, 2003.

Landegren et al., "A Ligase-Mediated Gene Detection Technique," Science 241:1077-80, 1988.

Landegren et al., "Padlock and proximity probes for in situ and array-based analyses: tools for the post-genomic era," Comparative and Functional Genomics, 4:525-30, 2003.

Lima and Kueltz, "Laser scanning cytometry and tissue microarray analysis of salinity effects on killifish chloride cells," J. Exp. Biol., 207:1729-39, 2004.

Lim et al., "Detection of Helicobacter pylori in gastric mucosa of patients with gastroduodenal disease by PCR-restriction analysis using the RNA polymerase gene (rpoB)," J. Clin. Micro. 41(7):3387-91, 2003.

Lin et al., "Evaluation of adipocyte apoptosis by laser scanning cytotnetry," Int. J. Obes., 28:1535-40, 2004.

Ma et al., "E2FBP1/DRIL1, an AT-Rich Interaction Domain-Family Transcription Factor, is Regulated by p53," Mol. Cancer Res., 1:438-44, 2003.

Maher et al., "Evaluation of culture methods and a DNA probe-based PCR assay for detection of campylobacter species in clinical specimens of feces," J. Clin. Micro. 41(7):2980-6, 2003.

Marras et al., "Genotyping SNPs with molecular beacons," Methods in Molecular Biol., 212:111-28, 2003.

Martin-Fernandez et al., "Adenovirus type-5 entry and disassembly followed in living cells by FRET, fluorescence anisotropy, and FLIM," Biophys. J., 87:1316-27, 2004.

Maruvada et al., "Cell cycle-dependent expression of thyroid hormone receptor-beta is a mechanism for variable hormone sensitivity," Mol. Biol. Cell, 15:1895-903, 2004.

Masiuk et al., "Simultaneous measurement of nucleolin and estrogen receptor in breast cancer cells by laser scanning cytometry," Anticancer Res., 24:963-6, 2004.

Mazur et al., "Induction of apoptosis in bone marrow cells after treatment of mice with WR-2721 and gamma-rays: relationship to the cell cycle," Cell Bio. Toxicol., 19:13-27, 2003.

Medina et al., "LAV694, a new antiproliferative agent showing improved skin tolerability vs. clinical standards for the treatment of actinic keratosis," Biochem. Pharmacol., 66:1885-95, 2003.

Megyeri et al., "Laser Scanning Cytometry for selection of green fluorescent protein transgenic mice using small number of blood cells," J. Biochem. Biophys. Methods, 61:183-7, 2004.

Miyaji-Yamaguchi et al., "Involvement of Nucleocytoplasmic Shuttling of Yeast Nap1 in Mitotic Progression," Mol. Cell. Biol., 23:6672-84, 2003.

Mocellin et al., "Use of laser scanning cytometry to study tumor microenvironment," Histol Histopathol, 18:609-15, 2003.

Mongillo et al, "Fluorescence resonance energy transfer-based analysis of cAMP dynamics in live neonatal rat cardiac myocytes reveals distinct functions of compartmentalized phosphodiesterases," Circ. Res., 95:1-8, 2004.

Moos et al., "Curcumin impairs tumor suppressor p53 function in colon cancer cells," Carcinogenesis, 25(9):1611-7, 2004.

Morales et al., "Role for the BRCA1 C-terminal Repeats (BRCT) Protein 53BP1 in Maintaining Genomic Stability," J. Biol. Chem. Chem. 278(17):14971-7, 2003.

Moshinsky et al., "A Widely Applicable, High-Throughput TR-FRET Assay for the Measurement of Kinase Autophosphoiylation: VEGFR-2 as a Prototype," J. of Biomolecular Screening, pp. 447-452, 2003.

Nawrocki et al., "The proteasome inhibitor bortezomib enhances the activity of docetaxel in ordiotopic human pancreatic tumor xenografts," Mol. Cancer Ther., 3(1):59-70, 2004.

Neri et al., "Transferring automation for large-scale development and production of invaderTM SNP assays," Advances in Nucleic Acid and Protein Analysis, 3926:117-25, 2000.

Nilsson et al., "Padlock probes: circularizing oligonucleotides for localized DNA detection," Science, 265:2085-8, 1994.

Nilsson et al., "Analyzing genes using closing and replicating circles," Trends in Biotechnol., 24(2):83-8, 2006.

Nohe and Petersen, "Analyzing for co-localization of proteins at a cell membrane," Curr. Pharm. Biotechnol., 5:213-20, 2004.

Oleinik and Krupenko, "Ectopic Expression of 10-Formyltetrahydrofolate Dehydrogenase in A549 Cells Induces 01 Cell Cycle Arrest and Apoptosis," Mol. Cancer Res., 1:577-88, 2003.

Oswald et al., "Mesenchymal Stem Cells Can Be Differentiated Into Endothelial Cells In Vitro," Stem Cells, 22:377-84, 2004.

Oswald et al., "Comparison offlow cytometry and laser scanning cytometry for the analysis of CD34+ hematopoietic stein cells," Cytometry, 57A:100-7, 2004.

Pfau et al., "Environmental oxygen tension affects phenotype in cultured bone marrow-derived macrophages," Am. J. Physiol. Lung Cell Mol. Physiol., 286:L354-62, 2004.

Piatek et al., "Molecular beacon sequence analysis for detecting drug resistance in Mycobacterium tuberculosis," Nat. Biotechnol., 16:359-63, 1998.

Pina-Vaz et al., "Novel Method Using a Laser Scanning Cytometer for Detection of Mycobacteria in Clinical Samples," J. Clin. Microbiol., 42(2):906-8, 2004.

(56) References Cited

OTHER PUBLICATIONS

Pozarowski et al., "Cell Cycle Effects and Caspase-Dependent and Independent Death of HL-60 and Jurkat Cells Treated with the Inhibitor of NF-kappaB Parthenolide," Cell Cycle, 2:377-83, 2003.
Pozarowski et al., "Simple, semiautomatic assay of cytostatic and cytotoxic effects of antitumor drugs by laser scanning cytometry: Effects of the bis-intercalator WP631 on growth and cell cycle of T-24 cells," Cytometry, 57A:113-9, 2004.
Pullen et al., "The flame retardants tetrabromobisphenol A and tetrabromobisphenol A-bisallylether suppress the induction of interleukin-2 receptor alpha chain (CD25) in murine splenocytes," Toxicology, 184:11-22, 2003.
Reed et al., "Mutation of hCDC4 Leads to Cell Cycle Deregulation of Cyclin E in Cancer," Cancer Res., 64:795-800, 2004.
Roth et al., "Effects of epithelial growth factor receptor (EGFR) kinase inhibitors on genetically reconstituted mouse mammary glands," Exp. Toxic. Pathol., 55:237-45, 2003.
Samaco et al., "Multiple pathways regulate MeCP2 expression in normal brain development and exhibit defects in autism-spectrum disorders," Hum. Mol. Genet., 13(6):629-39, 2004.
Santangelo et al., "Dual FRET molecular beacons for mRNA detection in living cells," Nucleic Acids Res., 32(6):1-9, 2004.
Schuemann et al., "Parenchymal, But Not Leukocyte, TNF Receptor 2 Mediates T Cell-Dependent Hepatitis in Mice," J. Immunol., 170:2129-37, 2003.
Schwartz et al., "Inhibition of experimental tobacco carcinogen induced head and neck carcinogenesis," Oral Oncol., 40:611-23, 2004.
Schwartz et al., "Oral cytology assessment by flow cytometry of DNA adducts, aneuploidy, proliferation and apoptosis shows differences between smokers and non-smokers," Oral Oncol., 39:842-54, 2003.
Shackney et al., "A suitable method for identifying cell aggregates in laser scanning cytometry listmode data for analyzing disaggregated cell suspensions obtained from human cancers," Cytometry, 59B:10-23, 2004.
Shackney et al., "Intracellular Patterns of Her-2/neu, ras, and Ploidy Abnormalities in Primary Human Breast Cancers Predict Postoperative Clinical Disease-Free Survival," Clin. Cancer Res., 10:3042-52, 2004.
Shakhman et al., "Induction by beta-bungarotoxin of apoptosis in cultured hippocainpal neurons is mediated by Ca2+-dependent formation of reactive oxygen species," J. Neurochem., 87:598-608, 2003.
Shibata et al., Lovastatin inhibits tumor growth and lung metastasis in mouse mammary carcinoma model: a p53-independent mitochondrial-mediated apoptotic mechanism. Carcinogenesis, 25(1):1887-98, 2004.
Smith et al., "LFA-1-induced T cell migration on ICAM-1 involves regulation of MLCK-mediated attachment and ROCK-dependent detachment," J. Cell Sci., 116:3123-33, 2003.
Smolewska et al., "Apoptosis of peripheral blood lymphocytes in patients with juvenile idiopathic arthritis," Ann. Rheum. Dis., 62:761-3, 2003.
Smolewski et al., "Caspase-mediated cell death in hematological malignancies: theoretical considerations, methods of assessment, and clinical implications," Leuk Lymphoma, 44(7):1089-104, 2003.
Solinas et al., "Duplex Scorpion primers in SNP analysis and FRET applications," Nucleic Acids Research 29(20):1-9, 2001.
Sooknanan and Malek, "NASBA: a detection and amplification system uniquely suited for RNA," Bio/Technology 13:563-64, 1995.
Strasberg Rieber et al., "Tumor apoptosis induced by ruthenium(II)-ketoconazole is enhanced in nonsusceptible carcinoma by monoclonal antibody to EGF receptor," Int. J. Cancer, 112:376-84, 2004.
Strife et al., "Direct Evidence That Bcr-Abl Tyrosine Kinase Activity Disrupts Normal Synergistic Interactions Between Kit Ligand and Cytokines in Primary Primitive Progenitor Cells," Mol. Cancer Res., 1:176-85, 2003.

Szodoray et al., "Programmed cell death in rheumatoid arthritis peripheral blood T-cell subpopulations determined by laser scanning cytometry," Lab. Invest., 83(12):1839-48, 2003.
Takemoto et al., "Cell Cycle-dependent Phosphorylation, Nuclear Localization, and Activation of Human Condensin," J. Biol. Chem., 279(6):4551-9, 2004.
Takita et al., "An analysis of changes in the expression of cyclins A and B1 by the cell array system during the cell cycle: Comparison between cell synchronization methods," Cytometry, 55A:24-9, 2003.
Tamamori-Adachi et al., "Critical Role of Cyclin D1 Nuclear Import in Cardiomyocyte Proliferation," Circ. Res., 92: e12-9, 2003.
Tamamori-Adachi et al., "Down-regulation of p27Kip1 promotes cell proliferation of rat neonatal cardiornyocytes induced by nuclear expression of cyclin DI and CDK4: Evidence for impaired Skp2-dependent degradation of p27 in terminal differentiation," J. Biol. Chem., 279(48):50429-36, 2004.
Thelwell et al., Mode of action and application of scorpion primers to mutation detection, Nucleic Acids Research, 28 (19):3752-61, 2000.
Thoren et al., "Membrane binding and translocation of cell penetrating peptides," Biochemistry, 43:3471-89, 2004.
Tyagi and Kramer, "Molecular beacons: probes that fluoresce upon hybridization," Nat. Biotechnology, 14:303-8, 1996.
Tyagi, et al., "Multicolor molecular beacons for allele discrimination," Nature Biotechnology, 16:49-53, 1998.
Unger et al. , "Monolithic microfabricated valves and pumps by multilayer soft lithography," Science, 288:113-6, 2000.
Valet et al., "Cytomics—new technologies: towards a human cytome project." Cytometry, 59A:167-71, 2004.
Vieyra et al., "Altered Subcellular Localization and Low Frequency of Mutations of INGI in Human Brain Tumors," Clin. Cancer Res., 9:5952-61, 2003.
Villamarin et al., A comparative analysis of the time-dependent antiproliferative effects of daunorubicin and WP631, Eur. J. Biochem., 270:764-70, 2003.
Walker et al., "Phenotype versus Genotype in Gliomas Displaying Inter- or Intratumoral Histological Heterogeneity," Clin. Cancer Res., 9:4841-51, 2003.
Wang et al., "Loss of 13q14-q21 and Gain of 5p14-pter in the Progression of Leiomyosarcoma," Mod. Pathol., 16 (8):778-85, 2003.
Wang et al., "Genomic instability and endoreduplication triggered by RAD17 deletion," Genes & Dev., 17:965-70, 2003.
Williams et al., "Differential effects of the proteasome inhibitor bortezomib on apoptosis and angiogenesis in human prostate tumor xenografts," Mol. Cancer Ther., 2:835-43, 2003.
Wilson et al., "Detection of Legionella pneumophila by real-time PCR for the mip gene" J. Clin. Micro., 41(7):3327-30, 2003.
Wu et al., "Telomere dysfunction: a potential cancer predisposition factor.," J. Natl. Cancer Inst., 95(16):1211-8, 2003.
Wu and Wallace, "The ligation amplification reaction (LAR)—amplification of specific DNA sequences using sequential rounds of template-dependent ligation," Genomics 4:560-9, 1989.
Yellon et al., "The role of leukocyte traffic and activation in parturition," Soc. Gynecol. Investig., 10:323-38, 2003.
Yuan et al., "The duration of nuclear extracellular signal-regulated kinase 1 and 2 signaling during cell cycle reentry distinguishes proliferation from apoptosis in response to asbestos," Cancer Res., 64:6530-6, 2004.
Zabaglo et al., "Measurement of proliferation marker Ki67 in breast tumour FNAs using laser scanning cytometry in comparison to conventional immunocytochemistry," Cytometrv, 56B:55-61, 2003.
Zabaglo et al., "Cell filtration-laser scanning cytometry for the characterisation of circulating breast cancer cells," Cytometry, 55A:102-8, 2003.
Zaccolo, "Use of chimeric fluorescent proteins and fluorescence resonance energy transfer to monitor cellular responses," Circ. Res., 94:866-73, 2004.
Zhang et al., "High urea and NaCl carbonylate proteins in renal cells in culture and in vivo, and high urea causes 8-oxoguanine lesions in their DNA," PNAS, 101(25):9491-6, 2004.
Zhang et al., "Detection of mitochondrial caspase activity in real time in situ in live cells," Microsc. Microanal., 10:442-8, 2004.

(56) References Cited

OTHER PUBLICATIONS

Zheng et al., "Calphostin-C Induction of Vascular Smooth Muscle Cell Apoptosis Proceeds through Phospholipase D and Microtubule Inhibition," J. Biol. Chem., 279(8):7112-8, 2004.
Lin et al., "Multiplex genotype determination at a large number of gene loci," Proc. Natl. Acad. Sci. USA, 93: 2582-7, 1996.
Zhu et al., "High-sensitivity capillary electrophoresis of double-stranded DNA fragments using monomeric and dimeric fluorescent intercalating dyes," Anal. Chem., 66:1941-8, 1994.
Zorov et al., "Examining intracellular organelle function using fluorescent probes: from animalcules to quantum dots," Circ. Res., 95:239-52, 2004.
Adinolfi et al., "Rapid detection of aneuploidies by microsatellite and the quantitative fluorescent polymerase chain reaction," Prenatal Diagnosis, 17(13):1299-311, 1997.
Ahn et al., "A fully integrated micromachined magnetic particle separator," J. of Microelectromechanical systems, 5 (3):151-8, 1996.
Bennett et al., "Toward the $1000 human genome," Pharmacogenomics, 6(4):373-82, 2005.
Berger et al., "Design of a microfabricated magnetic cell separator," Electrophoresis, 22:3883-92, 2001.
Blake et al., "Assessment of multiplex fluorescent PCR for screening single cells for trisomy 21 and single gene defects," Mol. Human Reproduction, 5(12):1166-75, 1999.
Bode et al., "Mutations in the tyrosine kinase domain of the EGFR gene are rare in synovial sarcoma," Modern Pathology, 19:541-7, 2006.
Braslavsky et al., "Sequence information can be obtained from single DNA molecules," PNAS, 100(7):3960-4, 2003.
Caggana, "Microfabricated devices for sparse cell isolation," CNF Project #905-00, Cornell Nanoscale Facility, pp. 32-33, May 2004.
Chan et al., "DNA mapping using microfluidic stretching and single-molecule detection of fluorescent site-specific tags," Genome Res., 14:1137-46, 2004.
Choesmel et al., "Enrichment methods to detect bone marrow micrometastases in breast carcinoma patients: clinical relevance," Breast Cancer Res., 6:R556-69, 2004.
Chiu et al., "Effects of blood-processing protocols on fetal and total DNA quantification in maternal plasma," Clin. Chem., 47(9):1607-13, 2001.
Chou et al., "A microfabricated device for sizing and sorting DNA molecules," Proc. Natl. Acad. Sci. USA, 96:11-13, 1999.
Cirigliano et al., "Clinical application of multiplex quantitative fluorescent polymerase chain reaction (QF-PCR) for the rapid prenatal detection of common chromosome aneuploidies," Mol. Human Reproduction, 7(10):1001-6, 2001.
De Alba et al., "Prenatal diagnosis on fetal cells obtained from maternal peripheral blood: report of 66 cases," Prenatal Diagnosis, 19:934-40, 1999.
Diehl and Diaz Jr., "Digital quantification of mutant DNA in cancer patients," Curr. Opin. Oncol. 19:36-42, 2007.
Di Naro et al., "Prenatal diagnosis of beta-thalassaemia using fetal erythroblasts enriched from maternal blood by a novel gradient," Mol. Human Reproduction, 6(6):571-4, 2000.
Dressman et al., "Transforming single DNA molecules into fluorescent magnetic particles for detection and enumeration of genetic variations," PNAS, 100(15):8817-22, 2003.
Emanuel and Pestka, "Amplification of specific gene products from human serum," GATA, 10(6):144-6, 1993.
Fan et al., "Noninvasive diagnosis of fetal aneuploidy by shotgun sequencing DNA from maternal blood," PNAS, 105 (42):16266-71, 2008.
Fan et al., "Single cell degenerate oligonucleotide primer-PCR and comparative genomic hybridization with modified control reference," J. of Zhejiang University (Science), 2(3):318-21, 2001.
Findlay et al., "Using MF-PCR to diagnose multiple defects from single cells: implications for PGD," Mol. Cell. Endocrinology, 183:S5-12, 2001.

Guetta et al., "Analysis of fetal blood cells in the maternal circulation: challenges, ongoing efforts, and potential solutions," Stem Cells and Development, 13:93-9, 2004.
Hahn et al., "Current applications of single-cell PCR," CMLS, Cell. Mol. Life Sci., 57:96-105, 2000.
Hahn and Holzgreve, "Prenatal diagnosis using fetal cells and cell-free fetal DNA in maternal blood: what is currently feasible?," Clin. Obstetrics and Gynecology, 45(3):649-56, 2002.
Hardenbol et al., "Highly multiplexed molecular inversion probe genotyping: over 10,000 targeted SNPs genotyped in a single tube assay," Genome Res., 15:269-75, 2005.
Hardenbol et al., "Multiplexed genotyping with sequence-tagged molecular inversion probes," Nature Biotechnology, 21 (6):673-8, 2003.
Hong et al., "A nanoliter-scale nucleic acid processor with parallel architecture," Nature Biotechnology, 22(4):435-9, 2004.
Hong et al., "Molecular biology on a microfluidic chip," J. Phys.: Condens. Matter, 18:S691-701, 2006.
Hromadnikova et al., "Quantitative analysis of DNA levels in maternal plasma in normal and Down syndrome pregnancies," BMC Pregnancy and Childbirth, 2(4):1-5, 2002.
Kazakov et al., "Extraceullular DNA of pregnant women blood," Tsitologiia, 37(3):232-6, 1995.
Kimura et al., "The DYRK1A gene, encoded in chromosome 21 Down syndrome critical region, bridges between beta-amyloid production and tau phosphorylation in Alzheimer disease," Human Molecular Genetics, 16(1):15-23, 2007.
Klein et al., "Comparative genomic hybridization, loss of heterozygosity, and DNA sequence analysis of single cells," Proc., Natl. Acad. Sci. USA, 96:4494-9, 1999.
Klein, "Single cell amplification methods for the study of cancer and cellular ageing," Mech. Ageing and Dev., 126:147-51, 2005.
Krivacic et al., "A rare-cell detector for cancer," PNAS, 101(29):10501-4, 2004.
Lo and Chiu, "Prenatal diagnosis: progress through plasma nucleic acids," Genetics, 8:71-7, 2007.
Lo et al., "Detection of fetal RhD sequence from peripheral blood of sensitized RhD-negative pregnant women," British J. of Haematology, 87:658-60, 1994.
Lo et al., "Detection of single-copy fetal DNA sequence from maternal blood," The Lancet, 335:1463-4, 1990.
Lo et al., "Digital PCR for the molecular detection of fetal chromosomal aneuploidy," PNAS, 104(32):13116-21, 2007.
Lo, "Fetal DNA in maternal plasma," Annals New York Academy of Sciences, 906:141-7, 2000.
Lo, "Noninvasive prenatal detection of fetal chromosomal aneuploidies by maternal plasma nucleic acid analysis: a review of the current state of the art," BJOB, 116:152-7, 2009.
Lo et al., "Plasma placental RNA allelic ratio permits noninvasive prenatal chromosomal aneuploidy detection," Nature Medicine, 13(2):218-23, 2007.
Lo et al., "Prenatal sex determination by DNA amplification from maternal peripheral blood," The Lancet, 2 (8676):1363-5, 1989.
Lo et al., "Presence of fetal DNA in maternal plasma and serum," The Lancet, 350:485-87, 1997.
Lo et al., "Quantitative analysis of fetal DNA in maternal plasma and serum: implications for noninvasive prenatal diagnosis," Am. J. Hum. Genet. 62:768-75, 1998.
Lun et al., "Microfluidics digital PCR reveals a higher than expected fraction of fetal DNA in maternal plasma," Clin. Chem., 54(10):1664-72, 2008.
Maloney et al., "Microchimerism of maternal origin persists into adult life," J. Clin. Invest., 104(1):41-7, 1999.
Marcus et al., "Microfluidic single-cell mRNA isolation and analysis," Anal. Chem., 78:3084-9, 2006.
Marcus et al., "Parallel picoliter RT-PCR assays using microfluidics," Anal. Chem., 78:956-8, 2006.
Martin et al., "A method for using serum or plasma as a source of DNA for HLA typing," Human Immunology, 33:108-13, 1992.
Mohamed et al., "Biochip for separating fetal cells from maternal circulation," J. of Chromatography, 1162:187-92, 2007.
Nagrath et al., "Isolation of rare circulating tumour cells in cancer patients by microchip technology," Nature, 450:1235-41, 2007.

(56) References Cited

OTHER PUBLICATIONS

Nelson et al., "Genotyping fetal DNA by non-invasive means: extraction from maternal plasma," Vox Sanguinis, 80:112-6, 2001.
Ng et al., "The concentration of circulating corticotropin-releasing hormone mRNA in maternal plasma is increased in preeclampsia," Clin. Chem., 49(5):727-31, 2003.
Oosterwijk et al., "Prenatal diagnosis of trisomy 13 on fetal cells obtained from maternal blood after minor enrichment," Prenatal Diagnosis, 18:1082-5, 1998.
Ottesen et al., "Microfluidic digital PCR enables multigene analysis of individual environment bacteria," Science, 314:1464-7, 2006.
Owen, "High gradient magnetic separation of erythrocytes," Biophys. J., 22:171-8, 1978.
Pertl and Bianchi, "Fetal DNA in maternal plasma: emerging clinical applications," Obstet. Gynecol., 98:483-90, 2001.
Poon and Lo, "Circulating fetal DNA in maternal plasma," Clinica Chimica Acta, 313:151-5, 2001.
Prieto et al., "Isolation of fetal nucleated red blood cells from maternal blood in normal and aneuploid pregnancies," Clin. Chem. Lab. Med., 40(7):667-72, 2002.
Purwosunu et al., "Clinical potential for noninvasive prenatal diagnosis through detection of fetal cells in maternal blood," Taiwanese J. Obstet. Gynecol., 45(1):10-20, 2006.
Rahil et al., "Rapid detection of common autosomal aneuploidies by quantitative fluorescent PCR on uncultured amniocytes," European J. of Human Genetics, 10:462-6, 2002.
Rickman et al., "Prenatal diagnosis by array-CGH," European J. Med. Genetics, 48:232-40, 2005.
Sakhnini and Khuzaie, "Magnetic behavior of human erythrocytes at different hemoglobin states," Eur. Biophys. J., 30:467-70, 2001.
Samura et al., "Diagnosis of trisomy 21 in fetal nucleated erythrocytes from maternal blood by use of short tandem repeat sequences," Clin. Chem., 47(9):1622-6, 2001.
Samura et al., "Female fetal cells in maternal blood: use of DNA polymorphisms to prove origin," Hum. Genet., 107:28-32, 2000.
Sambrook et al., Molecular Cloning: A Laboratory Manual, 2nd Ed., pp. 9.50-1; 11.46-49; 11.55-57; 15.55, 1989.
"Separation of RNA & DNA by gel filtration chromotagraphy," Edvotek, pp. 1-9, 1987.
Shendure et al., "Accurate multiplex polony sequencing of an evolved bacterial genome," Science, 309:1728-32, 2005.
Shendure and Ji, "Next-generation DNA sequencing," Nature Biotechnology, 26(10):1135-45, 2008.
Sherlock et al., "Assessment of diagnostic quantitative fluorescent multiplex polymerase chain reaction assays performed on single cells," Ann. Hum. Genet., 62:9-23, 1998.
Sparkes, et al., "New molecular techniques for the prenatal detection of chromosomal aneuploidy," J. Obstet. Gynaecol. Can., 30(7):617-21, 2008.
Sykes et al., "Quantitation of targets for PCR by use of limiting dilution," BioTechniques, 13(3):444-9, 1992.
Tanaka et al., "Genome-wide expression profiling of mid-gestation placenta and embryo using a 15,000 mouse developmental cDNA microarray," PNAS, 97(16):9127-32, 2000.
Troeger et al., "Approximately half of the erythroblasts in maternal blood are of fetal origin," Mol. Human Reporduction, 5(12):1162-5, 1999.
Uitto et al., "Probing the fetal genome: progress in non-invasive prenatal diagnosis," Trends in Mol. Medicine, 9 (8):339-43, 2003.
Vogelstein and Kinzler, "Digital PCR," Proc. Natl. Acad. Sci. USA, 96:9236-41, 1999.
Vona et al., "Enrichment, immunomorphological, and genetic characterization of fetal cells circulating in maternal blood," Am. J. of Pathology, 160(1):51-8, 2002.
Vrettou et al., "Real-time PCR for single-cell genotyping in sickle cell and thalassemia syndromes as a rapid, accurate, reliable, and widely applicable protocol for preimplantation genetic diagnosis," Human Mutation, 23:513-21, 2004.
Wang et al., "Allele quantification using molecular inversion probes (MIP)," Nucleic Acids Research, 33(21):1-14, 2005.
White et al., "Digital PCR provides sensitive and absolute calibration for high throughput sequencing," BMC Genomics, 10(116):1-12, 2009.
Xiong et al., "A simple, rapid, high-fidelity and cost-effective PCR-based two-step DNA synthesis method for long gene sequences," Nucleic Acids Research, 32(12):1-10, 2004.
Yang et al., "Rapid prenatal diagnosis of trisomy 21 by real-time quantitative polymerase chain reaction with amplification of small tandem repeats and S100B in chromosome21," Yonsei Medical J., 46(2):193-7, 2005.
Yu et al., "Objective aneuploidy detection for fetal and neonatal screening using comparative genomic hybridization (CGH)," Cytometry, 28:191-7, 1997.
Zhu et al., "Single molecule profiling of alternative pre-mRNA splicing," Science, 301:836-8, 2003.
Zimmermann, "Molecular diagnosis in prenatal medicine," Ph.D. thesis, 1-160, 2004.
International Search Report and Written Opinion for PCT/US2007/003209 dated Sep. 18, 2008, 8 pages.
U.S. Appl. No. 60/764,420 filed by Quake on Feb. 2, 2006.
Caggana, "Microfabricated devices for sparse cell isolation," CNF Project #905-00, Cornell NanScale Facility, 2 cover pages; pp. 38-39, 2003.
Margulies et al., "Genome sequencing in microfabricated high-density picolitre reactors," Nature, 437:376-80, 2005.
Non-Final Office Action, U.S. Appl. No. 11/701,686, dated Jan. 18, 2009, 24 pages.
Applicant's Response to Non-Final Office Action, U.S. Appl. No. 11/701,686, dated Jun. 17, 2009, 25 pages.
Final Office Action, U.S. Appl. No. 11/701,686, dated Sep. 11, 2009, 40 pages.
Allcock, H. R. and F. W. Lampe, "The Scope of Polymer Chemistry," Contemporary Polymer Chemistry, 2nd Ed., Prentice Hall: Englewood Cliffs, NJ, 1990, pp. 1-20 (plus cover and copyright pages).
Berlman, I. B., Handbook of Fluorescence Spectra of Aromatic Molecules, 2nd Ed., Academic Press: New York, NY, 1971, Chapters 1 and 3, pp. 1-38, 47-66 (plus cover and copyright pages).
Dieffenbach, C. W. and G. S. Dveksler, eds., PCR Primer: A Laboratory Manual, Cold Spring Harbor Laboratory Press: Plainview, NY, 1995, pp. 131-155, 193-202, 235-248, 287-409, 507-536 (plus cover and copyright pages).
Griffiths, J., Colour and Constitution of Organic Molecules, Academic Press: London, UK, 1976, Chapters 3 and 9; pp. 55-80, 240-270 (plus cover and copyright pages).
Kirkbright, G. F., "Fluorescent Indicators," Indicators, Pergamon Press: Oxford, UK, 1972, Chapter 9, pp. 685-708 (plus cover and copyright pages).
Mohamed, H. et al., "A Micromachiens Sparse-Cell Isolation Device: Application in Prenatal Diagnostics," Nanotech, vol. 3, 2006, pp. 641-644.
Pesce, A. J. et al., Fluorescence Spectroscopy: An Introduction for Biology and Medicine, Marcel Dekker Inc.: New York, NY, 1971, pp. v-247 (plus cover and copyright pages).
Spoerel, N. A. and F. C. Kafatos, "Identification of Genomic Sequences Corresponding to cDNA Clones," Methods in Enzymology: Guide to Molecular Cloning Techniques, vol. 152, Academic Press, Inc.:Orlando, FL, 1987, pp. 588-597 (plus cover and copyright pages).
White, C. E. and R. J. Argauer, Fluorescence Analysis: A Practical Approach, Mercel Dekker, Inc.: New York, NY, 1970, Chapters, 1, 3 and 6, pp. 1-9, 30-53, and 102-115 (plus cover and copyright pages).
Haugland, R. P. and K. D. Larison, eds., Handbook of Fluorescent Probes and Research Chemicals, 5th Edition, Molecular Probes, Inc.: Eugene, OR, 1992-1994, pp. 1-71, 89-98, 230-234 (plus cover and copyright pages).
PCT International Search Report and Written Opinion dated Sep. 24, 2007 issued in PCT/US2006/021416.
PCT International Preliminary Report on Patentability dated Dec. 6, 2007 issued in PCT/US2006/021416.
PCT International Search Report and Written Opinion dated Sep. 16, 2010 issued in PCT/US2010/020942.

(56) References Cited

OTHER PUBLICATIONS

Chinese Office Action dated Feb. 26, 2013 issued in 201080011426.7.
EP Supplemental Search Report and Written Opinion dated Aug. 28, 2009 issued in EP06836075.
EP Office Action dated Dec. 23, 2009 issued in EP06836075.
EP Office Action dated May 14, 2012 issued in EP06836075.
EP Oral Proceedings dated May 17, 2013 issued in EP06836075.
EP Supplemental Search Report dated Jun. 14, 2012 issued in EP11196269.
European Supplementary Search Report on Patentability and Written Opinion dated Apr. 26, 2012 issued in EP10732056.6.
US Office Action dated Apr. 13, 2012 issued in U.S. Appl. No. 12/687,018.
US Final Office Action dated Mar. 1, 2013 issued in U.S. Appl. No. 12/687,018.
US Office Action dated Sep. 27, 2010 issued in U.S. Appl. No. 11/916,025.
US Final Office Action dated May 13, 2011 issued in U.S. Appl. No. 11/916,025.
US Office Action dated Aug. 17, 2012 issued in U.S. Appl. No. 11/916,025.
US Final Office Action dated Apr. 26, 2013 issued in U.S. Appl. No. 11/916,025.
Ao et al. (1998) "Preimplantation genetic diagnosis of inherited cancer:Familial adenomatous *Polyposis coli*" *Journal of Assisted Reproduction and Genetics* 15(3): 140-144.
C1 Single-Cell AutoPrep System (2012) *Fluidigm Corporation* pp. 1-4.
Deitmaier et al. (1999) "Multiple mutation analyses in single tumor cells with improved whole genome amplification" *American Journal of Pathology* 154(1): 83-95.
Gibson et al. (1996) "A Novel Method for Real Time Quantitative RT-PCR" *Genome Research* 6(10) : 995-1001.
Heinmoller et al. (2002) "Toward efficient analysis of mutations in single cells from ethanol-fixed, paraffin-embedded, and immunohistochemically stained tissues" *Laboratory Investigation* 82(4): 443-453.
Laboratory Talk (2012) "Isolation and processing of individual cells" 1 page.
Lovmar et al. (2003) "Quantitative evaluation by minisequencing and microarrays reveals accurate multiplexed SNP genotyping of whole genome amplified DNA" *Nucleic Acids Research* 31(21) : (E129)1-9.
Lovmar et al. (2005) "Silhouette scores for assessment of SNP genotype clusters" *BMC Genomics* 6(1): (35)1-6.
Simpson et al. (1994) "Isolating fetal cells in maternal circulation for prenatal diagnosis" *Prenatal Diagnosis* 14(13): 1229-1242.
Snabes et al. (1994) "Preimplantation Single-Cell Analysis of Multiple Genetic Loci by Whole-Genome Amplification" *Proceedings of the National Academy of Sciences of USA* 91(13): 6181-6185.
Wells et al. (1999) "Detailed chrnlosomal and molecular genetic analysis of single cells by whole genome amplification and comparative genomic hybridisation" *Nucleic Acids Research* 27(4): 1214-18.
Wheeler et al. (2003) "Microfluidic Device for Single-Cell Analysis" *Analytical Chemistry* 75(14): 3581-3586.
White et al. (2011) "High-throughput microfluidic single-cell RT-qPCR" *PNAS USA* 108: 13999-14004 plus supplement.
U.S. Appl. No. 14/102,331, filed Dec. 13, 2013, Hamilton et al.
PCT International Preliminary Report on Patentability and Written Opinion dated Jul. 19, 2011 issued in PCT/US2010/020942.
EA Office Action dated Mar. 29, 2013 issued in 201170933.
Chinese Second Office Action dated Nov. 15, 2013 issued in 201080011426.7.
Israeli Office Action dated Nov. 14, 2013 issued in IL 214034.
Singapore Search Report and Written Opinion dated Feb. 26, 2013 issued in SG 201205203-1.
Singapore Search Report and Written Opinion dated Dec. 13, 2013 issued in SG 201205203-1.
EP Extended Search Report dated Jan. 30, 2014 issued in EP 13 18 1405.
US Notice of Allowance dated Sep. 9, 2013 issued in U.S. Appl. No. 12/687,018.
Bertram et al., (Jan. 1, 1995) "Detection of DNA in Single Cells Using an Automated Cell Deposition Unit and PCR", *Biotechniques, Informa Healthcare*, US, 19(4):616, 618-620.
Miyaji et al., (Jan. 1, 1998) "A novel single cell PCR assay: detection of human T lymphotropic virus type 1 DNA in lymphocytes of patients with adult T cell leukemia," Bio-Technical Methods Section (BTS), *Leukemia*, pp. 1645-1650 [Retrieved from the Internet on Jan. 20, 2014: URL:http://www.nature.com/leu/journal/v12/n10/pdf/2401154a.pdf].
Rettig et al., (Sep. 1, 2005) "Large-scale single-cell trapping and imaging using microwell arrays", *Analytical Chemistry, American Chemical Society*, US, 77(17):5628-5634.
Xing et al., (Sep. 15, 2004) "A Three-Dimensional Flow Control Concept for Single-Cell Experiments on a Microship. 1. Cell Selection, Cell Retention, Cell Culture, Cell Balancing, and Cell Scanning," *Analytical Chemistry, American Chemical Society*, U.S., 76(18):5273-5281.
US Office Action dated Oct. 21, 2014 issued in U.S. Appl. No. 14/102,331.
Chinese Third Office Action dated May 13, 2014 issued in 201080011426.7.
Chinese Fourth Office Action dated Dec. 2, 2014 issued in 201080011426.7.
European Office Action dated Apr. 7, 2014 issued in EP 10 732 056.6.
Singapore Search Report and Written Opinion dated Nov. 6, 2014 issued in SG 201205203-1.
Saitou et al., (Jan. 1, 2008) "Single-cell cDNA high-density oligonucleotide microarray analysis: detection of individual cell types and properties in complex biological processes", *Reproductive Biomedicine Online, Reproductive Healthcare Ltd.* GB, 16(1):26-40.

\* cited by examiner

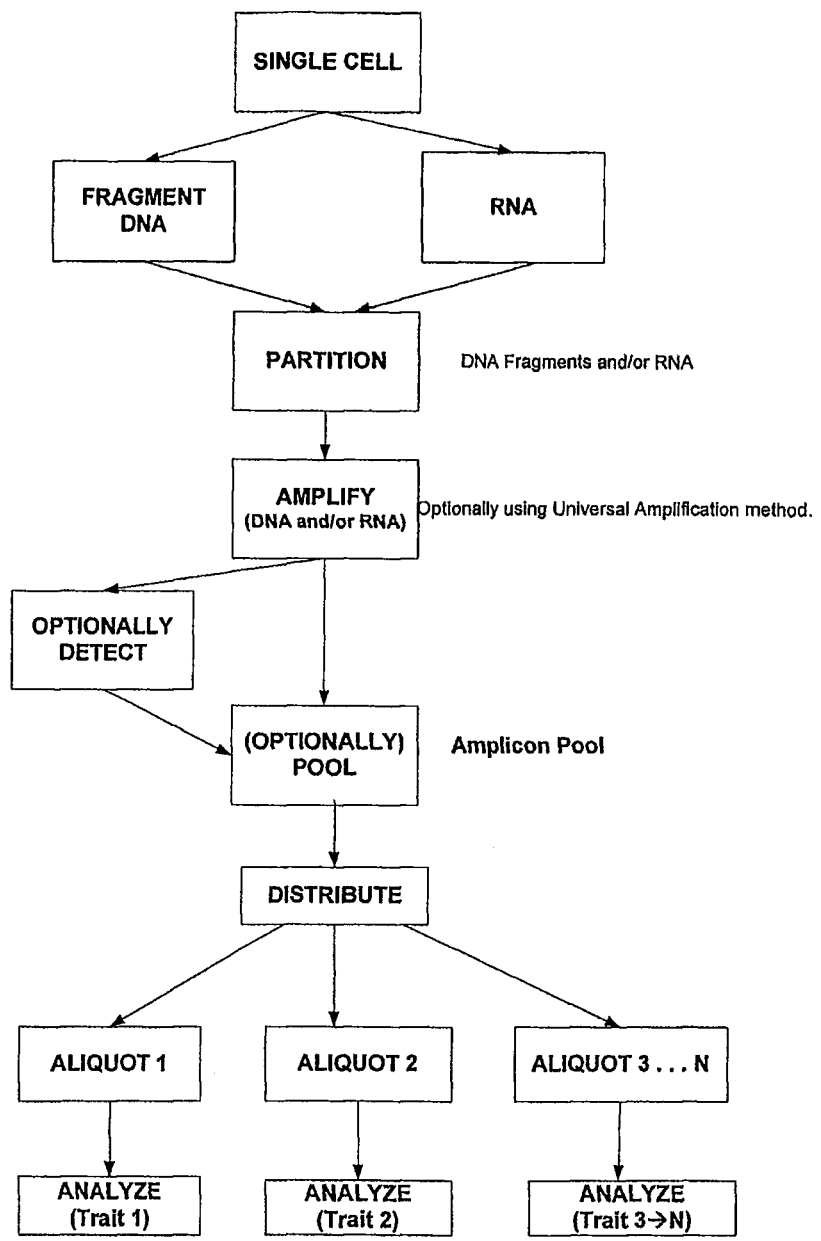

Partition of Cells

Target 1

Target 2

SEQUENCE LISTING

<160> NUMBER OF SEQ ID NOS: 12

<210> SEQ ID NO 1
<211> LENGTH: 25
<212> TYPE: DNA

```
<213> ORGANISM: Artificial Sequence
<220> FEATURE:
<223> OTHER INFORMATION: primer

<400> SEQUENCE: 1
ccccaataga agattcaata ttaag                                    25

<210> SEQ ID NO 2
<211> LENGTH: 25
<212> TYPE: DNA
<213> ORGANISM: Artificial Sequence
<220> FEATURE:
<223> OTHER INFORMATION: primer

<400> SEQUENCE: 2
atgtagaagt aaacttactt ggatg                                    25

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
ggtggagctt caattggaga g                                        21

<210> SEQ ID NO 4
<211> LENGTH: 24
<212> TYPE: DNA
<213> ORGANISM: Artificial Sequence
<220> FEATURE:
<223> OTHER INFORMATION: primer

<400> SEQUENCE: 4
gtgtaaccta ctttcataac acca                                     24

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
aagtgttctg taacaggtat acc                                      23

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
ggtccattag cagcctcaca                                          20

<210> SEQ ID NO 7
<211> LENGTH: 19
<212> TYPE: DNA
<213> ORGANISM: Artificial Sequence
<220> FEATURE:
<223> OTHER INFORMATION: primer

<400> SEQUENCE: 7
agtcgtaaca aggtagccg                                           19
```

```
<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
cyrytgccaa ggcatccacc                                              20

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
actttaaacg catgaagata t                                            21

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
atattttgac cttctggggt                                              20

<210> SEQ ID NO 11
<211> LENGTH: 16
<212> TYPE: DNA
<213> ORGANISM: Artificial Sequence
<220> FEATURE:
<223> OTHER INFORMATION: primer

<400> SEQUENCE: 11
gcaatgtcaa cagcaa                                                  16

<210> SEQ ID NO 12
<211> LENGTH: 16
<212> TYPE: DNA
<213> ORGANISM: Artificial Sequence
<220> FEATURE:
<223> OTHER INFORMATION: primer

<400> SEQUENCE: 12
catagcgtct tgcatg                                                  16
```

ANALYSIS USING MICROFLUIDIC PARTITIONING DEVICES

CROSS-REFERENCE TO RELATED APPLICATIONS

This application is a continuation of U.S. application Ser. No. 11/916,025, filed Dec. 10, 2008, which is a 371 of international application No. PCT/US2006/021416, filed Jun. 2, 2006, which claims benefit of U.S. provisional application No. 60/687,010, filed Jun. 2, 2005, the entire contents of which are herein incorporated by reference.

FIELD OF THE INVENTION

The invention relates to methods, reagents and devices for detecting and characterizing nucleic acids, cells, and other biological samples.

BACKGROUND

A variety of nucleic acid amplification assays and immunological assays are used for analysis of cells and nucleic acids. These assays can be used to detect or characterize nucleic acid sequences associated with particular diseases or genetic disorders, for genotyping, for gene expression analyses, to detect and identify pathogens such as viruses, bacteria and fungi), for paternity and forensic identification, and for many other purposes. However, in some applications the efficiency and sensitivity of these assays is reduced, which may render the assays useless or at minimum require that additional manipulations and/or significant amounts of expensive reagents be used. For example, when a cell or molecule to be analyzed is from a sample with a large excess of non-target cells or molecules (e.g., as in genetic or phenotypic analysis of a rare cell in a background of other cells) conventional assay methods are inadequate. Similarly, when a number of different targets must be detected in a single sample, conventional approaches (e.g., multiplex PCR) are expensive, inefficient or not sufficiently sensitive. Thus, new methods, reagents and devices for detection and characterization of nucleic acids, cells, and other biological molecules will find broad application in biomedicine and other fields.

BRIEF SUMMARY

The invention relates to methods, reagents and devices for detection and characterization of nucleic acids, cells, and other biological samples. In one aspect, the invention provides an assay method including the following steps (a) partitioning a sample into a plurality of sub-samples, where said sample comprises a plurality of nucleic acid molecules, and where at least two sub-samples comprise at least one nucleic acid molecule; (b) providing sufficient reagents in each sub-sample to amplify a target sequence or sequences; (c) amplifying the target sequence(s) in the sub-sample(s) containing target sequence(s) thereby producing amplicons in the sub-sample; (d) distributing the amplicons into a plurality of aliquots; and, (e) for each aliquot, determining a property of amplicons in the aliquot.

In a related aspect, the invention provides an assay method including the following steps (a) partitioning a sample into a plurality of sub-samples, where said sample comprises a plurality of nucleic acid molecules, and where at least two sub-samples comprise at least one nucleic acid molecule; (b) providing sufficient reagents in each sub-sample to amplify at least two different target sequences; (c) amplifying target sequence(s) in at least two sub-sample(s) thereby producing amplicons in the sub-sample(s); (d) combining the amplicons from said at least two sub-samples to create an amplicon pool; (d) dividing the amplicon pool into a plurality of aliquots; and, (e) for each aliquot, determining a property of amplicons in the aliquot. In one embodiment, the sample is partitioned into at least $10^4$ sub-samples. In one embodiment, each sub-sample has a volume of less than one nanoliter. In one embodiment, the nucleic acid molecules comprise DNA and/or mRNA. In one embodiment, the amplification is by PCR or RT-PCR. In one embodiment, sufficient reagents are provided to amplify at least 10, 20, or 50 different target sequences, if present. In one embodiment, the amplicon pool is divided into at least 10, 20, 50 or 100 aliquots. In one embodiment, the sample contains a plurality of cells having nucleic acid molecules, and partitioning the sample involves partitioning intact cells into a plurality of sub-samples. In one embodiment, the sample contains only one cell.

In another aspect, the invention provides an assay method including the following steps (a) partitioning a sample comprising a plurality of separable cells into at least 1000 separate reaction chambers in a massively partitioning device (MPD), where after partitioning at least two reaction chambers each comprise exactly one cell; (b) providing in each reaction chamber one or more reagents for determining a property or properties of a cell, where the same reagents are provided in each chamber; and (c) determining at least two different properties of a single cell in a chamber and/or determining at least one property for at least two different cells in different chambers. In one embodiment, at least 99% of the reaction chambers contain zero or one cell. In one embodiment, the cells are bacterial cells. In one embodiment, the reagents include reagents for nucleic acid amplification. In one embodiment, at least one property is the presence or absence in the cell of a nucleic acid having a specified sequence. In one embodiment, at least one property is other than the presence or absence in the cell of a nucleic acid having a specified sequence.

In another aspect, the invention provides a method for amplification and detection of multiple target DNA sequences in a sample, including the following steps: (a) providing a sample containing (i) multiple target DNA sequences, (ii) a primer pair corresponding to each of said multiple target DNA sequences, each pair consisting of a first primer comprising $U_1$, $B_1$ and F domains in the order 5'-$U_1$-$B_1$-F-3' and a second primer comprising $U_2$ and R domains in the order 5'-$U_2$-R-3', where each pair of F and R primers is capable of annealing specifically to a different target DNA sequence under stringent annealing conditions; (iii) a universal primer pair capable of amplifying a double stranded DNA molecule with the structure

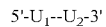

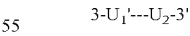

where $U_1'$ is the sequence complementary to $U_1$ and $U_2'$ is the sequence complementary to $U_2$; (b) subjecting the sample to multiple cycles of melting, reannealing, and DNA synthesis thereby producing amplicons for each of said multiple target DNA sequences, and (c) detecting the amplicons using a probe that anneals to sequence of the amplicon having the sequence of the $B_1$ domain or its complement. In one embodiment, the sample also contains a second set of multiple target sequences, a primer pair corresponding to to each of the target sequences in the second set, each pair consisting of a first primer comprising $U_1$, $B_2$ and F domains in the order 5'-$U_1$-$B_2$-F-3' and a second primer comprising $U_2$ and R domains in the order 5'-$U_2$-R-3', where each pair of F and R oligonucleotides is capable of annealing specifically to a different target DNA sequence in the second set of multiple target sequences under stringent annealing conditions; and where amplicons for each of the multiple target DNA sequences of the second set are produced; and detecting the amplicons for each of the multiple target DNA sequences using a probe that anneals to sequence of the amplicon having the sequence of the $B_2$ domain or its complement. In one embodiment, $U_1, B_1, F_1, U_2$ and $R_1$ domains are between 6 and 30 nucleotides in length. In one embodiment the probe is a molecular beacon. In one embodiment, the probe is a a Taqman™-type probe.

In another aspect, the invention provides a microfluidic device, having (a) a first region comprising (i) a flow channel formed within an elastomeric material and having a first end and a second end in fluid communication with each other through said channel, where said channel may be branched or unbranched; (ii) an inlet for introducing a sample fluid in communication with said channel, said inlet; (iii) an outlet in communication with said flow channel; (iv) a plurality of control channels overlaying the flow channel(s), where an elastomeric membrane separates the control channels from the flow channels at each intersection, the elastomeric membrane disposed to be deflected into or withdrawn from the flow channel in response to an actuation force, and where, when the control channels are actuated the flow channel is partitioned into at least 1000 reaction chambers not in fluidic communication with each other; (b) a second region compromising a channel or chamber interposed between and in communication with said outlet in (a) and a flow channel in the third region; (c) a third region comprising a plurality of flow channels (e.g., blind flow channels), in fluidic communication with the channel or chamber of the second region, with a region of each flow channel defining a reaction site; (d) a control channel or channels that when actuated separates the first and second regions; (e) a control channel or channels that when actuated separates the second and third regions; and (f) a control channel or channels that when actuated separates the reaction sites of said flow channels from the other portions of control channels.

BRIEF DESCRIPTION OF THE FIGURES

FIGS. 3A-C are flow charts illustrating partition and analysis of nucleic acids using methods of the invention. FIG. 3A illustrates partition and analysis of nucleic acids in which multiple target sequences are amplified. FIG. 3B illustrates partition and analysis acids in which target sequences in only a single chamber are amplified. FIG. 3C illustrates analysis of nucleic acids of a single cell.

DETAILED DESCRIPTION

Definitions

Figure 1A:
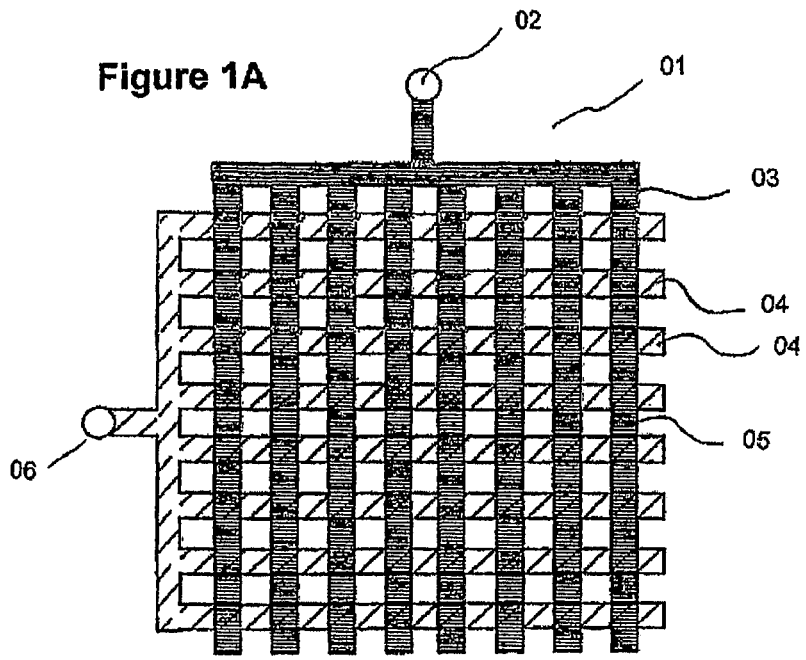
FIGS. 1A and 1B show an exemplary design of a massively partitioning device (MPD) in valve off (FIG. 1A) and valve actuated (FIG. 1B) states.

The term "elastomer" has the general meaning used in the art. Thus, for example, Allcock et al. (Contemporary Polymer Chemistry, 2nd Ed.) describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials can be characterized by a Young's modulus. The elastomeric materials utilized in the microfluidic devices disclosed herein typically have a Young's modulus of between about 1 Pa-1 TPa, in other instances between about 10 Pa-100 GPa, in still other instances between about 20 Pa-1 GPa, in yet other instances between about 50 Pa-10 MPa, and in certain instances between about 100 Pa-1 MPa. Elastomeric materials having a Young's modulus outside of these ranges can also be utilized depending upon the needs of a particular application. Microfluidic devices can be fabricated from an elastomeric polymer such as GE RTV 615 (formulation), a vinylsilane crosslinked (type) silicone elastomer (family). However, elastomeric microfluidic systems are not limited to this one formulation, type or even this family of polymer; rather, nearly any elastomeric polymer is suitable. Given the tremendous diversity of polymer chemistries, precursors, synthetic methods, reaction conditions, and potential additives, there are a large number of possible elastomer systems that can be used to make monolithic elastomeric microvalves and pumps (including, for example, perfluoropolyethers, polyisoprene, polybutadiene, polychloroprene, polyisobutylene, poly(styrene-butadiene-styrene), polyurethanes, and silicones, for example, or poly(bis(fluoroalkoxy)phosphazene) (PNF, Eypel-F), poly(carborane-siloxanes) (Dexsil), polyacrylonitrile-butadiene) (nitrile rubber), poly(1-butene), poly(chlorotrifluoroethylene-vinylidene fluoride) copolymers (Kel-F), poly(ethyl vinyl ether), poly(vinylidene fluoride), poly(vinylidene fluoride-hexafluoropropylene) copolymer (Viton), elastomeric compositions of polyvinylchloride (PVC), polysulfone, polycarbonate, polymethylmethacrylate (PMMA), polytertrafluoroethylene (Teflon), polydimethylsiloxane, polydimethylsiloxane copolymer, and aliphatic urethane diacrylate). The choice of materials typically depends upon the particular material properties (e.g., solvent resistance, stiffness, gas permeability, and/or temperature stability) required for the application being conducted. Additional details regarding the type of elastomeric materials that can be used in the manufacture of the components of the microfluidic devices disclosed herein are set forth in Unger et al. (2000) *Science* 288:113-116, PCT Publications WO 02/43615, WO 2005030822, WO 2005084191 and WO 01/01025; and U.S. patent publication No. 20050072946.

A "reagent" refers broadly to any agent used in a reaction, other than the analyte (e.g., cell or nucleic acid being analyzed). Exemplary reagents for a nucleic acid amplification reaction include, but are not limited to, buffer, metal ions, polymerase, reverse transcriptase, primers, template nucleic acid, nucleotides, labels, dyes, nucleases and the like. Reagents for enzyme reactions include, for example, substrates, cofactors, buffer, metal ions, inhibitors and activators. Reagents for cell-based reactions include, but are not limited to, cells, cell specific dyes and ligands (e.g., agonists and antagonists) that bind to cellular receptors.

The terms "nucleic acid," "polynucleotide," and "oligonucleotide" include a polymeric form of nucleotides of any length, including, but not limited to, ribonucleotides or deoxyribonucleotides. There is no intended distinction in length between these terms. Further, these terms refer only to the primary structure of the molecule. Thus, in certain embodiments these terms can include triple-, double- and single-stranded DNA, as well as triple-, double- and single-stranded RNA. They also include modifications, such as by methylation and/or by capping, and unmodified forms of the polynucleotide. More particularly, the terms "nucleic acid," "polynucleotide," and "oligonucleotide," include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA.

A "primer" is a single-stranded polynucleotide capable of acting as a point of initiation of template-directed DNA or RNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically is at least 7 nucleotides long and, more typically range from 10 to 30 nucleotides in length. Other primers can be somewhat longer such as 30 to 50 nucleotides long. In this context, primer "length" refers to the portion of an oligo- or polynucleotide that hybridizes to a complementary "target" sequence and primes synthesis. For example, in the primer 5'-$U_1$-$B_1$-F1-3' the length of $F_1$ might be 20 nucleotides and the combined length of U, B and F1 could be 60 nucleotides or more (typically between 30 and 100 nucleotides). Short primer molecules generally require cooler temperatures to form sufficiently stable hybrid complexes with the template. A primer need not reflect the exact sequence of the template but must be sufficiently complementary to hybridize with a template. The term "primer site" or "primer binding site" refers to the segment of the target DNA to which a primer hybridizes. The term "primer pair" means a set of primers including a 5' "upstream primer" that hybridizes with the complement of the 5' end of the DNA sequence to be amplified and a 3' "downstream primer" that hybridizes with the 3' end of the sequence to be amplified.

A primer or probe anneals or hybridizes to a complementary target sequence. The primer or probe may be exactly complementary to the target sequence or can be less than perfectly complementary. Typically the primer has at least 65% identity to the complement of the target sequence over a region of at least 7 nucleotides, more typically over a region in the range of 10-30 nucleotides, and often over a region of at least 14-25 nucleotides, and more often has at least 75% identity, at least 85% identity or 90% identity. It will be understood that certain bases (e.g., the 3' base of a primer) generally should be exactly complementary to corresponding base of the target sequence. Primer and probes generally anneal to the target sequence under stringent conditions. Stringent annealing conditions refers to conditions in a range from about 5° C. to about 20° C. or 25° C. below the melting temperature ($T_m$) of the target sequence and a probe with exact or nearly exact complementarity to the target. As used herein, the melting temperature is the temperature at which a population of double-stranded nucleic acid molecules becomes half-dissociated into single strands. Methods for calculating the $T_m$ of nucleic acids are well known in the art (see, e.g., Berger and Kimmel (1987) METHODS IN ENZYMOLOGY, VOL. 152: GUIDE TO MOLECULAR CLONING TECHNIQUES, San Diego: Academic Press, Inc. and Sambrook et al. (1989) MOLECULAR CLONING: A LABORATORY MANUAL, 2ND ED., VOLS. 1-3, Cold Spring Harbor Laboratory), both incorporated herein by reference). As indicated by standard references, a simple estimate of the $T_m$ value may be calculated by the equation: $T_m=81.5+0.41$(% G+C), when a nucleic acid is in aqueous solution at 1 M NaCl (see e.g., Anderson and Young, Quantitative Filter Hybridization in NUCLEIC ACID HYBRIDIZATION (1985)). The melting temperature of a hybrid (and thus the conditions for stringent hybridization) is affected by various factors such as the length and nature (DNA, RNA, base composition) of the probe and nature of the target (DNA, RNA, base composition, present in solution or immobilized, and the like), and the concentration of salts and other components (e.g., the presence or absence of formamide, dextran sulfate, polyethylene glycol). The effects of these factors are well known and are discussed in standard references in the art A "probe" is an nucleic acid capable of binding to a target nucleic acid of complementary sequence through one or more types of chemical bonds, usually through complementary base pairing, usually through hydrogen bond formation, thus forming a duplex structure. The probe binds or hybridizes to a "probe binding site." The probe can be labeled with a detectable label to permit facile detection of the probe, particularly once the probe has hybridized to its complementary target. The label attached to the probe can include any of a variety of different labels known in the art that can be detected by chemical or physical means, for example. Suitable labels that can be attached to probes include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates. Probes can vary significantly in size. Some probes are relatively short. Generally, probes are at least 7 to 15 nucleotides in length. Other probes are at least 20, 30 or 40 nucleotides long. Still other probes are somewhat longer, being at least 50, 60, 70, 80, 90 nucleotides long. Yet other probes are longer still, and are at least 100, 150, 200 or more nucleotides long. Probes can be of any specific length that falls within the foregoing ranges as well.

The term "label" refers to a molecule or an aspect of a molecule that can be detected by physical, chemical, electromagnetic and other related analytical techniques. Examples of detectable labels that can be utilized include, but are not limited to, radioisotopes, fluorophores, chromophores, mass labels, electron dense particles, magnetic particles, spin labels, molecules that emit chemiluminescence, electrochemically active molecules, enzymes, cofactors, enzymes linked to nucleic acid probes and enzyme substrates. The term "detectably labeled" means that an agent has been conjugated with a label or that an agent has some inherent characteristic (e.g., size, shape or color) that allows it to be detected without having to be conjugated to a separate label.

A "polymorphic marker" or "polymorphic site" is the locus at which divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms.

A "single nucleotide polymorphism" (SNP) occurs at a polymorphic site occupied by a single nucleotide, which is the site of variation between allelic sequences. The site is usually preceded by and followed by highly conserved sequences of the allele (e.g., sequences that vary in less than $\frac{1}{100}$ or $\frac{1}{1000}$ members of the populations). A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

The term "haplotype" refers to the designation of a set of polymorphisms or alleles of polymorphic sites within a gene of an individual.

A used herein, "plurality" means at least three. In general a plurality of cells, nucleic acid molecules, etc., will contain at least 10, at least about $10^2$, at least about $10^3$, or at least about $10^4$ different cells, molecules, etc.

A used herein, "entities" refers to a plurality of structurally similar biological molecules or structures (e.g., macromolecules such as nucleic acids, protein, carbohydrates and lipids; cells or subcellular structures or components; viruses) or nonbiological particles that are separate and distinct from each other in the sense that they can be separated into separate reaction chambers using a MPD. "Entity" refers to a single such molecule or structure.

The term "biological sample", refers to a sample obtained from an organism or from components of an organism, such as cells, biological tissues and fluids. In some methods, the sample is from a human patient. Such samples include sputum, blood, blood cells (e.g., white cells), tissue or fine needle biopsy samples, urine, peritoneal fluid, and fleural fluid, or cells therefrom.

A. Introduction

The invention relates generally to analysis of macromolecules and small particles, and particularly to analysis of nucleic acids, proteins, and individual cells. In certain aspects, the invention relates to analysis methods involving massive partitioning. Massive partitioning of liquid samples, i.e., dividing the sample into thousands of isolated reaction volumes, has been made possible by the development of specially designed elastomeric microfluidic devices. These devices can be referred to as "massively partitioning devices" or MPDs and are sometimes referred to as "chips" or Digital Isolation and Detection Integrated Fluidic Circuits (DID IFCs). Exemplary devices are described in McBride et al. (PCT publication WO 2004/089,810, published on Oct. 21, 2004; copending, commonly assigned U.S. patent application Ser. No. 10/819,088 published as patent publication No. 20050019792 on Jan. 27, 2005; and copending, commonly assigned U.S. patent application Ser. No. 10/819,088 published as patent publication No. 20050252773 on Nov. 17, 2005, each of which is incorporated by reference in its entirety for all purposes and the specific purposes describe therein and herein; hereinafter referred to together as "McBride et al."). Using MPDs, a sample can be partitioned into a multitude of isolated reaction chambers, and reactions carried out simultaneously in each chamber. For example, McBride et al., supra, describes the performance of 21,000 simultaneous PCR reactions in a single microfluidic chip, in a volume of 90 picoliters per reaction and with single template molecule sensitivity.

In a first broad aspect, the invention provides new methods and devices for analysis of a sample containing nucleic acids, proteins, other biomolecules, cells, microorganisms, viruses, and other biological or nonbiological entities, in which the sample undergoes massive partitioning as part of the analysis process.

In a second broad aspect, the invention provides methods and reagents for amplification and/or detection of a nucleic acid. These methods and reagents find particular application in the analysis of nucleic acids partitioned using a MPD, but may be used in amplification-based analysis of any nucleic acid.

These and other inventions are described in the following sections.

B. Massively Partitioning Devices

Methods described in this disclosure can be, and in some cases are necessarily, carried out using an elastomeric microfluidic device. Methods for fabricating elastomeric microfluidic devices capable of separating molecules or cells and for carrying out reactions are known in the art (see, e.g., Unger et al., 2000, Science 288:113-116, PCT Publications WO 01/01025 and WO/02/43615; and U.S. patent application Ser. No. 10/306,798 published as Pat App. No. 20030138829 on Jul. 24, 2003). In particular, exemplary elastomeric massively partitioning devices (MPDs) are described in McBride et al., supra and references cited therein. Based on these and other publications, one of ordinary skill in the art guided by this disclosure will be able to practice all aspects of the inventions described herein. Accordingly, elastomeric microfluidic devices are described only briefly below.

General Structure of Microfluidic Devices

Figure 1B:
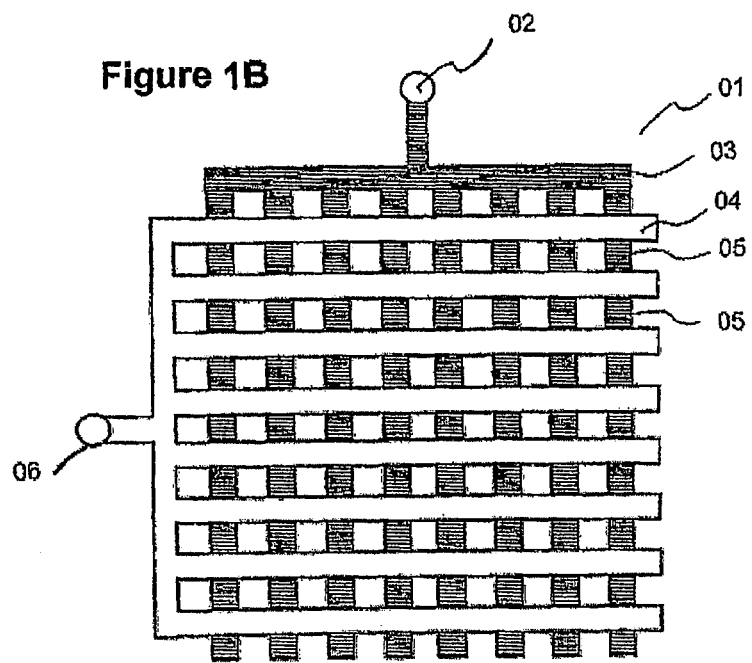

Elastomeric microfluidic devices are characterized in part by utilizing various components such as flow channels, control channels, valves, pumps, vias, and/or guard channels from elastomeric materials. FIGS. 1A and 1B show an exemplary design of a massively partitioning device.

A "flow channel" refers generally to a flow path through which a solution can flow. A "blind channel" refers to a flow channel which has an entrance but not a separate exit. A "control channel" is a channel separated from a flow channel by an elastomeric membrane that can be deflected into or retracted from the flow channel in response to an actuation force. The term "valve" refers to a configuration in which a flow channel and a control channel intersect and are separated by an elastomeric membrane that can be deflected into or retracted from the flow channel in response to an actuation force. An "isolated reaction site" or "reaction chamber" refers to a reaction site that is not in fluid communication with other reactions sites present on the device, and which is created by the actuation of control channels in the device. A "via" refers to a channel formed in an elastomeric device to provide fluid access between an external port of the device and one or more flow channels. Thus, a via can serve as a sample input or output, for example. "Guard channels" may be included in elastomeric microfluidic devices for use in heating applications to minimize evaporation of sample from the reaction sites. Guard channels are channels formed within the elastomeric device through which water can be flowed, to increase the water vapor pressure within the elastomeric material from which the device is formed, thereby reducing evaporation of sample from the reaction sites. The guard channels are similar to the control channels in that typically they are formed in a layer of elastomer that overlays the flow channels and/or reaction site. Typically, the guard channels are placed adjacent and over flow channels and reaction sites as these are the primary locations at which evaporation is the primary concern. Guard channels are typically formed in the elastomer utilizing the MSL techniques and/or sacrificial-layer encapsulation methods cited above. The solution flowed through the guard channel includes any substance that can reduce evaporation of water.

The devices incorporate flow channels, control channels and valves to isolate selectively a reaction site at which reagents are allowed to react. FIGS. 1A and 1B depict an exemplary design of a partitioning microfluidic device 01 in a valve off and valve actuated state. Referring to the figure, a sample is injected into inlet 02 which is in communication with branched partitioning channel system 03 of the device. Solution flow through flow channels of the device is controlled, at least in part, with one or more control channels that are separated from the flow channel by an elastomeric membrane or segment. This membrane or segment can be deflected into or retracted from the flow channel with which a control channel is associated by applying an actuation force to the control channels so that solution flow can be entirely blocked by valves. Actuating the control valves creates isolated reaction chambers 05 in which individual reactions can be conducted. The reaction chambers can number from $10^3$ to $10^5$ or more be at a density of at least 100 sites/cm$^2$ and can range up to at least 2000, 3000, 4000 or more than 4000 sites/cm$^2$. Very small wells or cavities can be formed within an elastomeric material to increase the volume of the reaction chamber. Valves can be actuated by injecting gases (e.g., air, nitrogen, and argon), liquids (e.g., water, silicon oils and other oils), solutions containing salts and/or polymers (including but not limited to polyethylene glycol, glycerol and carbohydrates), and the like into the port.

Although FIG. 1 illustrates a MPD with branched flow channels, any channel configuration (flow channel path) that can be partitioned by control channels can be used in accordance with the invention, including, for example, square, spiral or serpentine configurations.

The dimensions of flow channels in a MPD can vary widely. Typically channels are from about 0.1 μm to about 1000 μm in any dimension, sometimes from about 0.1 to about 100 μm, and sometimes from about 0.1 to about 10 μm. In one embodiment the channels have a high aspect ratio (e.g., a height to width ratio of from about 2:1 to about 10:1) to increase channel density and/or to increase signal collection from channels containing a detectably labeled moiety. For example, in some embodiments the channel has a columnar shape in which the dimensions of floor and ceiling are smaller that the dimensions of the walls, and a signal (e.g., fluorescence, infra red or visible radiation) is detected through the ceiling or floor. Appropriate channel dimensions will depend in part on the nature of the entities being partitioned. For partition of eukaryotic cells, for example, a dimension should be at least sufficient for passage of the cell (e.g., 2-5 times the dimension of the cell). However, for the purpose of restricting movement the dimensions can be on the order of 0.75 times the smallest dimension of the particle. Microfluidic manipulation and analysis of particles is also described in U.S. Patent Pub. 20040229349 entitled "Microfluidic particle-analysis systems" and incorporated herein by reference.

Reactions (e.g., nucleic acid amplification, protein binding, etc.) are allowed to occur in each chamber. For example, PCR reactions can be initiated by heating the chambers (e.g., placing the device on a suitably programmed flat plate thermocycler.

The results or products of the reaction can be detected using any of a number of different detection strategies. Because the MPDs are usually made of elastomeric materials that are relatively optically transparent, reactions can be readily monitored using a variety of different detection systems at essentially any location on the microfluidic device. Most typically, however, detection occurs at the reaction site itself.

The nature of the signal to be detected will, of course, determine, to a large extent, the type of detector to be used. The detectors can be designed to detect a number of different signal types including, but not limited to, signals from radioisotopes, fluorophores, chromophores, electron dense particles, magnetic particles, spin labels, molecules that emit chemiluminescence, electrochemically active molecules, enzymes, cofactors, enzymes linked to nucleic acid probes and enzyme substrates. Illustrative detection methodologies suitable for use with the present microfluidic devices include, but are not limited to, light scattering, multichannel fluorescence detection, infra-red, UV and visible wavelength absorption, luminescence, differential reflectivity, and confocal laser scanning. Additional detection methods that can be used in certain application include scintillation proximity assay techniques, radiochemical detection, fluorescence polarization, fluorescence correlation spectroscopy (FCS), time-resolved energy transfer (TRET), fluorescence resonance energy transfer (FRET) and variations such as bioluminescence resonance energy transfer (BRET). Additional detection options include electrical resistance, resistivity, impedance, and voltage sensing.

A detector can include a light source for stimulating a reporter that generates a detectable signal. The type of light source utilized depends in part on the nature of the reporter being activated. Suitable light sources include, but are not limited to, lasers, laser diodes and high intensity lamps. If a laser is utilized, the laser can be utilized to scan across a set of detection sections or a single detection section. Laser diodes can be microfabricated into the microfluidic device itself. Alternatively, laser diodes can be fabricated into another device that is placed adjacent to the microfluidic device being utilized to conduct a thermal cycling reaction such that the laser light from the diode is directed into the detection section.

Detectors can be microfabricated within the microfluidic device, or can be a separate element. A number of commercially-available external detectors can be utilized. Many of these are fluorescent detectors because of the ease in preparing fluorescently labeled reagents. Specific examples of detectors that are available include, but are not limited to, Applied Precision ArrayWoRx (Applied Precision, Issaquah, Wash.) and the ABI 7700 (Applied Biosystems, Inc., Foster City, Calif.).

Fabrication

Microfluidic devices are generally constructed utilizing single and multilayer soft lithography (MSL) techniques and/or sacrificial-layer encapsulation methods. The basic MSL approach involves casting a series of elastomeric layers on a micro-machined mold, removing the layers from the mold and then fusing the layers together. In the sacrificial-layer encapsulation approach, patterns of photoresist are deposited wherever a channel is desired. These techniques and their use in producing microfluidic devices is discussed in detail, for example, by Unger et al., 2000, *Science* 288:113-116; by Chou, et al., 2000, "Integrated Elastomer Fluidic Lab-on-a-chip-Surface Patterning and DNA Diagnostics, in Proceedings of the Solid State Actuator and Sensor Workshop, Hilton Head, S.C.; in PCT Publication WO 01/01025; and in published U.S. patent application No. 20050072946 (each incorporated herein by reference).

In one approach, the foregoing fabrication methods initially involve fabricating mother molds for top layers (e.g., the elastomeric layer with the control channels) and bottom layers (e.g., the elastomeric layer with the flow channels) on silicon wafers by photolithography with photoresist (Shipley SJR 5740). Channel heights can be controlled precisely by the spin coating rate. Photoresist channels are formed by exposing the photoresist to UV light followed by development. Heat reflow process and protection treatment is typically achieved as described by Unger et al. supra. A mixed two-part-silicone elastomer (GE RTV 615) is then spun into the bottom mold and poured onto the top mold, respectively. Spin coating can be utilized to control the thickness of bottom polymeric fluid layer. The partially cured top layer is peeled off from its mold after baking in the oven at 80° C. for 25 minutes, aligned and assembled with the bottom layer. A 1.5-hour final bake at 80° C. is used to bind these two layers irreversibly. Once peeled off from the bottom silicon mother mold, this RTV device is typically treated with HCL (0.1N, 30 min at 80° C.). This treatment acts to cleave some of the Si—O—Si bonds, thereby exposing hydroxy groups that make the channels more hydrophilic.

The device can then optionally be hermetically sealed to a support. The support can be manufactured of essentially any material, although the surface should be flat to ensure a good seal, as the seal formed is primarily due to adhesive forces. Examples of suitable supports include glass, plastics and the like.

In certain devices, the devices formed according to the foregoing method result in the substrate (e.g., glass slide) forming one wall of the flow channel. Alternatively, the device once removed from the mother mold is sealed to a thin elastomeric membrane such that the flow channel is totally enclosed in elastomeric material. For certain uses, e.g., PCR amplification, flow channels and chambers enclosed in elastomeric material (i.e., without a glass wall) are preferred. The resulting elastomeric device can then optionally be joined to a substrate support. In some cases, the device is made as described in U.S. patent publication No. 20050072946. In some cases, the device uses "push-up valves" described in U.S. patent publication No. 20050072946 (e.g., FIG. 37B). "Push-up" refers to low actuation pressure geometry in which the membrane deflects upwards to seal off the upper fluid channel. In this geometry, the deflectable membrane is featureless and exhibits a substantially constant thickness.

Reagents can be deposited in reaction chambers before addition of a sample to the MPD. A number of commercially available reagent spotters and established spotting techniques can be used to deposit the reagent(s). Microfluidic devices in which reagents are deposited at the reaction sites during manufacture are typically formed of three layers. The bottom layer is the layer upon which reagents are deposited. The bottom layer can be formed from various elastomeric materials as described in the references cited above on MLS methods. Typically, the material is polydimethylsiloxane (PDMS) elastomer. Based upon the arrangement and location of the reaction sites that is desired for the particular device, one can determine the locations on the bottom layer at which the appropriate reagents should be spotted. Because PDMS is hydrophobic, the deposited aqueous spot shrinks to form a very small spot. The deposited reagents are deposited such that a covalent bond is not formed between the reagent and the surface of the elastomer because, as described earlier, the reagents are intended to dissolve in the sample solution once it is introduced into the reaction site. In some versions, the reagent is designed to be inactive or unavailable to a reaction until a specified condition occurs (e.g., a polymerase not activated until heated or until the addition of a necessary cofactor).

The other two layers of the device are the layer in which the flow channels are formed and the layer in which the control and optionally guard channels are formed. These two layers are prepared according to the general methods set forth earlier in this section. The resulting two layer structure is then placed on top of the first layer onto which the reagents have been deposited. A specific example of the composition of the three layers is as follows (ration of component A to component B): first layer (sample layer) 30:1 (by weight); second layer (flow channel layer) 30:1; and third layer (control layer) 4:1. It is anticipated, however, that other compositions and ratios of the elastomeric components can be utilized as well. During this process, the reaction sites are aligned with the deposited reagents such that the reagents are positioned within the appropriate reaction site.

C. Partitioning, Detection and Analysis of Nucleic Acids

In this section, methods for analysis of nucleic acids in a sample are described. The methods involve massive partitioning of the sample and any nucleic acid molecules it contains, and amplification (as defined herein) of target sequences in the partitioned nucleic acid molecules. Various versions of the methods may also involve application of particular amplication strategies, pooling of amplification products, analysis of pooled amplification products and/or other features that will be apparent upon reading this disclosure. This section also describes devices (i.e., massively partitioning devices, MPDs) useful in carrying out analyses according to the method.

Figure 3A:
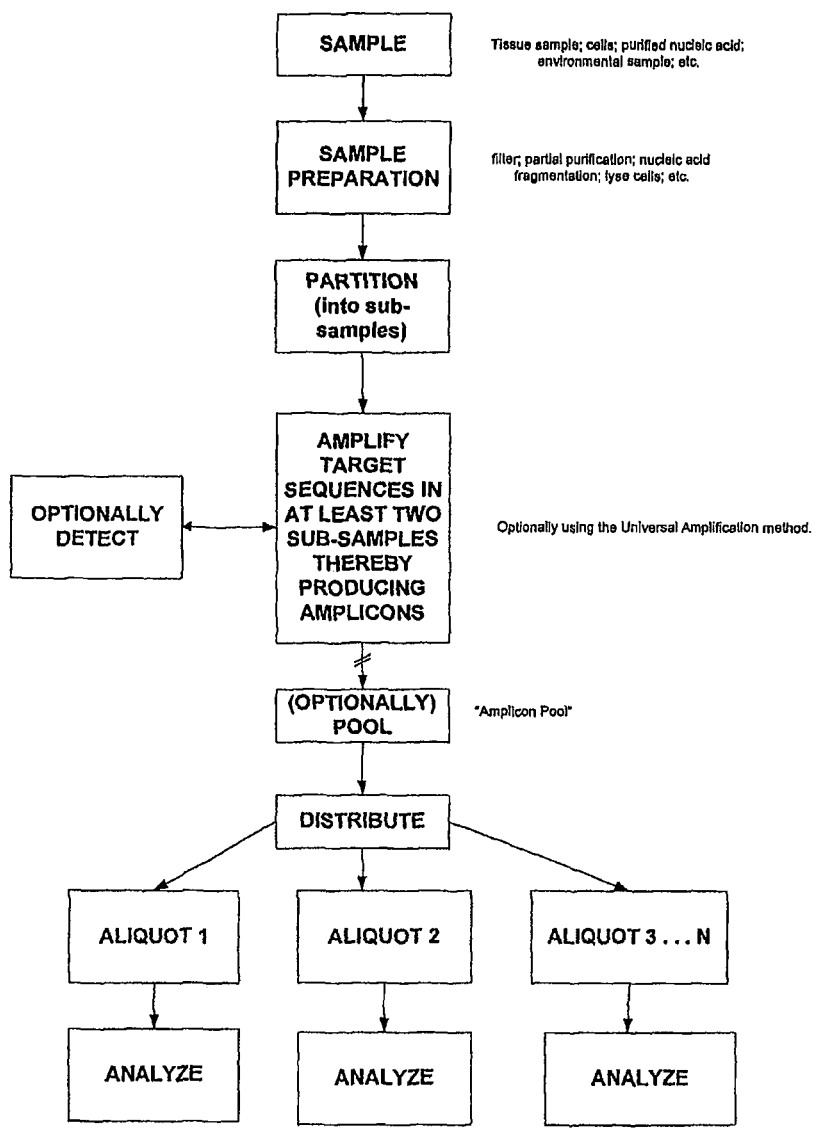
Figure 3B:
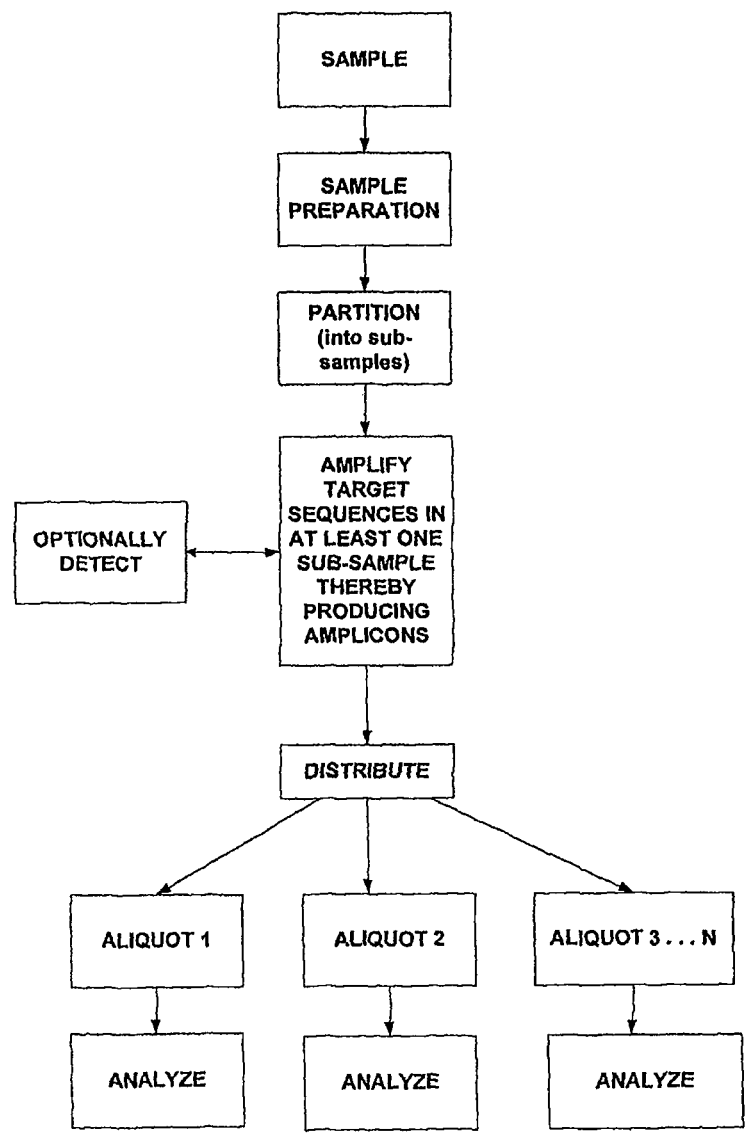
Figure 4:
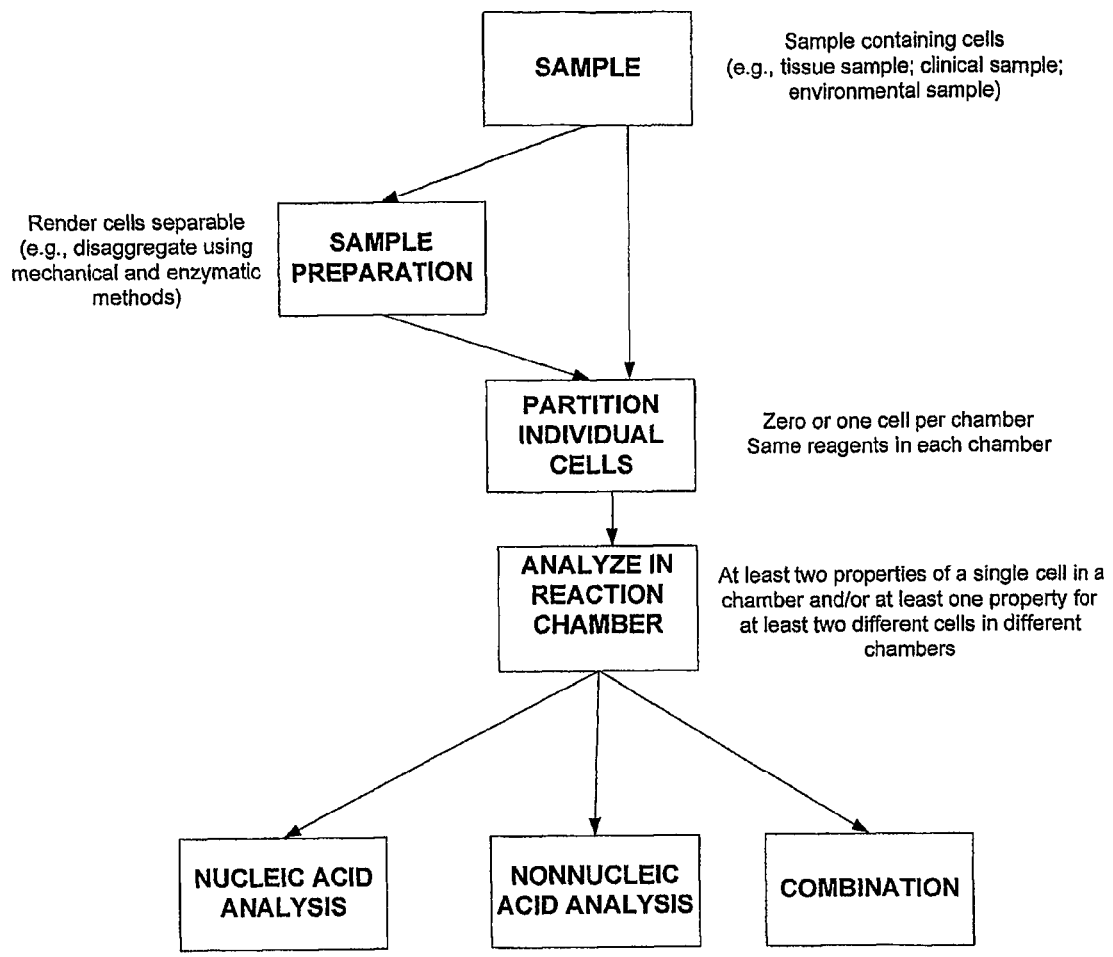
FIG. 4 is a flow chart illustrating partition of cells and analysis of their properties.
Figure 5:
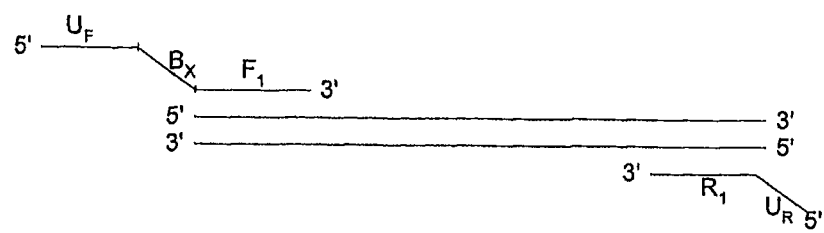
FIG. 5 is an illustration of primers used in the universal amplification method.
Figure 5:
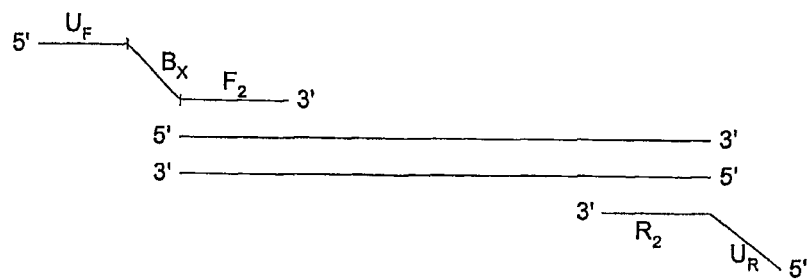

Analytical methods described in this section can be used for deleting the presence or absence of a target sequence, detection of polymorphisms; single polynucleotide polymorphism (SNP) analysis; haplotype analysis; amplification of a segment for sequence determination, gene expression analysis, quantification of nucleic acids, analysis of cells (see Section D, below), as well as other applications that will be apparent to one of skill guided by this disclosure. Although this section focuses on analysis of nucleic acids it will be appreciated by the reader that many aspects of the description in this section will be applicable, with appropriate modification, to analysis of other molecules and of cells. FIGS. 3A and 3B are flow charts illustrating partition and analysis of nucleic acids in which multiple targets are amplified in which amplicons may be pooled. FIG. 3B illustrates partition and analysis of nucleic acids in which, in one embodiment, target molecules in only a single chamber are amplified.

i) Samples Containing Nucleic Acids

In one step of the assay method, a sample containing a plurality of nucleic acid molecules is partitioned into a plurality of sub-samples, at least two of which each comprise at least one nucleic acid molecule.

Samples that may be analyzed according to the invention are any fluid sample that contains nucleic acids. A variety of types of samples can be used, so long as at least some nucleic acids can be partitioned from each other by the MPD. The nucleic acids can be free in solution or can be contained in particles or within cells suspended in a fluid. Samples may be processed so that any nucleic acids in the sample can be amplified. For example, in samples containing cells or viruses, the cells or viruses can be lysed or disrupted, using such routine methods as exposure to enzymes (such as lysozyme), detergents, denaturants (such as guanidine salts) and/or physical disruption) before the sample. Any method of liberating nucleic acids that results in nucleic acid molecules sufficiently intact and purified to amplify fragments is suitable. Examples of samples containing nucleic acids are cell lysates or cell fractions, water samples containing microorganisms, purified DNA resuspended in an aqueous buffer, sputum, blood, nucleated blood cells, tissue or fine needle biopsy samples, urine, peritoneal fluid, fecal samples, and fleural fluid, or cells therefrom. Exemplary samples include cells and cell lysates (e.g., eukaryotic cells, human cells, animal cells, plant cells, fetal cells, embryonic cells, stem cells, blood cells, lymphocytes, bacterial cells, recombinant cells and cells infected with a pathogen, tissue samples), viruses, purified or partially purified DNA or RNA, environmental samples (e.g., water samples), food samples, forensic samples, plant samples and the like. It will apparent that the sample can contain other compounds and macromolecules in addition to nucleic acids. If necessary for the functioning of a microfluidic device non-nucleic acid components and/or particulates can be removed by filtration, sedimentation or other methods.

In one embodiment of the invention, the nucleic acids are contained in cells, organelles, or viruses and the nucleic acids are not released (e.g., the cells are not lysed) until at least after a partitioning step. Particular aspects of this embodiment are discussed in Section D, below.

Analysis of nucleic acids in a sample generally involves determining whether the sample contains a nucleic acid having a particular target sequence. A target sequence may be predefined (i.e., known prior to analysis) or may be a sequence in a segment of a nucleic acid defined by other parameters (e.g., defined as the segment of a gene that can be amplified by a particular primer pair).

A target sequence can be any nucleic acid sequence of interest, such as a sequence associated with a gene, a sequence that identifies a particular allele or polymorphism, a sequence that, alone in combination with other genotypic or phenotypic markers, identifies the presence in the sample of a particular organism or strain, and the like. A target sequence can also include sequences flanking a sequence of interest, such as the sequences flanking a SNP. In addition, in some cases as will be recognized from context, a "target sequence" is a sequence added during an amplification step. For example, the B and U sequences discussed below in the context of a Universal Amplification method can be referred to as "target sequences" recognized by a probe or amplification primer.

A target sequence can be found in DNA (including genomic, mitochondrial DNA, viral DNA, recombinant DNA and complementary cDNA made from RNA) or in RNA (including rRNA, mRNA and iRNA). If a target sequence is detected in a sample it is possible to deduce that the sample contains a nucleic acid molecule containing the detected sequence or its complement. For example, a sample from a human patient can be analyzed to determine whether a viral nucleotide sequence (the target sequence) is detectable in the sample, in order to diagnose (or rule out) viral infection. As another example, genomic DNA from a human patient can be analyzed to determine whether a particular polymorphism is or is not present in a subject's genome.

In some cases, it will be advantageous to fragment the nucleic acid molecules prior to the partitioning step. For example, to characterize two genes on different regions of a eukaryotic chromosome it may be useful to fragment the DNA to produce smaller nucleic acid molecules so that the genes can be separately partitioned (i.e., partitioned into different sub-samples). Fragmentation can be accomplished enzymatically (e.g., using restriction enzymes), mechanically or chemically. In one embodiment, shearing is accomplished by passing the DNA through a channel of a MPD with a diameter (bore size) that is sufficiently small, or which varies in diameter along the length of the channel, so as to sheer large nucleic acids as they pass through. A sample containing a single DNA molecule (e.g., a single chromosome) contains a plurality of nucleic acids upon fragmentation of the single molecule.

ii) Partitioning of a Sample Containing Nucleic Acid Molecules

Methods for partitioning a sample using a MPD are provided in Section B, above. The terms "to partition," "partitioning," "partitioned," and grammatical equivalents refer to the process of separating a sample into a plurality of sub-samples using a MPD. A sample is partitioned by introducing the sample into the flow channels and reaction sites with valves open and then closing the valves to isolate each sub-sample. It will be recognized that each sub-sample is contained (for at least a period of time) in a separate reaction chamber such that the sample is isolated from (not in fluidic communication with) other sub-samples. It is sometimes convenient to refer to the "sample" even after it has been partitioned into sub-samples. Thus, in some contexts "sample" can refer to the aggregate contents of the sub-samples or chambers after partition, as well as before partition.

When a sample containing a complex mixture of nucleic acid molecules it is partitioned into very small-volume sub-samples, the effective concentration of the target sequence in the sub-sample(s) in which it is located is significantly increased. Effective concentration of the target occurs because, while the number of molecules of target in the sample does not change as a result of the partitioning, the number of other molecules (including molecules that can produce side reactions, e.g., primer-dimers and noncomplementary DNA sequences in the sample) is linearly proportional to volume. For example, if a 30 microliter sample containing one molecule of interest is partitioned into ten thousand subsamples (each with a volume of 3 nanoliters) the effective concentration of molecule of interest is enriched by a factor of $10^4$ in the chamber in which it is located. Since the ratio of target to side reactions is inversely proportional to volume, partitioning into a small volume increases this ratio (i.e., effectively concentrates). As noted by McBride et al., such an increase in effective concentration results in remarkable sensitivity and fidelity of PCR-based detection.

Typically the sample is partitioned into at least about $10^3$ different sub-samples or reaction chambers, sometimes at least about $5 \times 10^3$ different sub-samples or chambers, sometimes $10^4$ different sub-samples or chambers, often at least about $2 \times 10^4$ different sub-samples or chambers, sometimes at least about $3 \times 10^4$ different sub-samples or chambers, and sometimes at least about $10^5$ different sub-samples or chambers. In certain embodiments the sample is partitioned into between 100 and 100,000 sub-samples, more often between 1000 and 50,000 sub-samples, and sometimes between 1000 and 20,000 sub-samples.

Typically the volume of each sub-sample is less than about 1000 picoliters (pL), often less than about 500 pL, sometimes less than about 100 pL, and sometimes less than about 50 pL.

The relationship between the number of nucleic acid molecules (or non-nucleic acid macromolecules, particles or cells) in a sample, the number of chambers into which the sample is partitioned, and the distribution of number of nucleic acid molecules or other entities in each chamber can be estimated using well know methods. For example, to determine the number of chambers (C) into which the number (N) particles (e.g. cells, nucleic acid molecules, etc.) would be partitioned so that most or essentially all of the chambers contained either 0 or 1 particle can be determined using a Poisson Distribution:

$$P(x, \lambda) = \frac{e^{-\lambda}\lambda^x}{x!}. \quad [1]$$

$P(x,\lambda)$ is the probability of finding x particles if the average number of particles in a box is $\lambda$. We can get this by setting the average number ($\lambda$) such that $$P(0, \lambda) + P(1, \lambda) \geq x$$
$$\frac{e^{-\lambda}\lambda^0}{0!} + \frac{e^{-\lambda}\lambda^1}{1!} \geq x$$
$$e^{-\lambda} + e^{-\lambda}\lambda \geq x$$
$$e^{-\lambda}(1 + \lambda) \geq x$$

The average number of particles in a box is $\lambda$=N/C, so if you know $\lambda$ and N, you can find C:

$$C = \frac{N}{\lambda}$$

$\lambda$ is easily determined using eqn. [1] above.
For instance, if x is 0.99 (i.e. 99% chance of a chamber containing a 0 or 1 particle), $$e^{-\lambda}(1-\lambda) \geq 0.99$$

$$\lambda \leq \sim 0.1487$$

If N is 10,000, then $$C \cong \frac{10000}{0.1487}$$

C≥67250 chambers are required to have 99% likelihood of 0 or 1 particles per chamber. Although this calculation is provided for illustration it will be understood that any method (emperical or analytical) may be used. In some applications it will be useful to use such a calculation and adjust (e.g., dilute) the sample and/or select a MPD with an appropriate number of chambers for an increased likelihood there will be few, if any, chambers with more than a predetermined number of target molecules (e.g., 1) per chamber.

iii) Amplification of Partitioned Nucleic Acids

Following the partitioning step, any target sequences of interest that are in the sample are amplified. As used herein, nucleic acid "amplification" is a process that produces multiple nucleic acid molecules (called "amplicons") based on the presence of a particular target sequence. Most often the amplicons include a base sequence that is the same as, or complementary to, the target sequence so that amplification means that the number of copies of the target sequence increases. These identical or complementary amplicons are the products, for example and without limitation, of the Polymerase Chain Reaction (PCR) [see, Dieffenbach and Dvksler, 1995, PCR Primer: A Laboratory Manual. CSHL press, Cold Spring Harbor, USA]; Nucleic Acid Sequence Based Amplification (NASBA) [see Sooknanan and Malek, 1995, *BioTechnology* 13:563-65] SPIA™ Isothermal Linear Amplification, Ribo-SPIA, X-SPIA™ [Nugen Technologies, San Carlos Calif., see U.S. Pat. No. 6,251,639, WO 02/72772; US2003/0017591 A1]; the Ligase Chain Reaction (LCR) [Wu and Wallace, 1989, Genomics 4:560; Landegren et al., 1988, *Science* 241:1077]; Transcription amplification [Kwoh et al., 1989, *Proc. Natl. Acad. Sci. USA* 86:1173]; Self-sustained sequence replication [Guatelli et al., 1990, *Proc. Nat. Acad. Sci. USA* 87:1874]. In some embodiments, however, an amplicon is a nucleic acid with a sequence different from the target sequence and the process of amplification consists of increasing the number of amplicons if the target is present in a chamber, but not in the absence of the target sequence.

As noted above, typically the invention is used to simultaneously assay for multiple different target sequences in the same sample (e.g., sequences of multiple different genes or gene segments, or alternative sequences of a single gene). For example, provided with a patient blood sample, it may be useful to assay the sample for the presence of several (e.g., 10, 20 or 100) different sequences each characteristic of a different pathogen. In one embodiment, the different sequences are amplified in different reaction chambers. For example, an assay to detect the presence of multiple mutations in different genes from an individual sample will result in analysis of products in different reaction chambers if the genes are on fragments distributed to different sub-samples. In other embodiments, multiple different target sequences are assayed for and/or detected in a single reaction chamber, such as, for example, when the reaction chamber contains a single rare cell and the assay is designed to analyse several genetic loci in the cell genome. For example, an assay to determine which of several possible polymorphisms (e.g. defining a haplotype) are represented at a specific genomic site, multiple primers or probes may be used to determine which of several possible target sequences are present in a single reaction chamber. Very often both types of amplification are used.

A variety of methods are known for "multiplex" analysis (amplification of multiple sequences from one reaction) and can be adapted for use in a single reaction chamber MPDs. In one embodiment amplification is conducted using a universal primer strategy in which each target sequence is initially amplified by a pair of target sequence specific primers that include a 3-prime domain with a gene-specific sequence and a 5-prime domain with a universal (not target specific) sequence. For example, N different target sequences can be detected using primers 5'-$U_1$-$F_N$-3' and 5'-$U_2$-$R_N$-3' where $F_N$ and $R_N$ are forward and reverse PCR primers for each gene N, and $U_1$ and $U_2$ are sequences common to all of the primer pairs and $U_1$ and $U_2$ may be the same or different. Subsequent rounds of amplification can be conducted using primers 5'-$U_1$-3' and 5'-$U_2$-3'. See, e.g., Zhenwu Lin et al., 1996, "Multiplex genotype determination at a large number of gene loci" *Proc. Nat'l Acad. Sci USA* 93: 2582-87. When used in an MPD this strategy allows use of a low concentration of target specific primers (thereby reducing expense and the chances of primer dimer and other unintended side reactions) and a higher concentration of universal primers.

In one embodiment, the multiplex amplification is carried out in a MPD using the primers and strategy described below in Section C(v).

Amplification reagents, including primers, can be provided by prepositioning reagents in reaction chambers, by combining reagents with the sample before partitioning, by a combination of prepositioning and combining, or by any other suitable method. Specific amplification reagents will depend on the amplification method and sample, but can include primers, polymerase, reverse transcriptase, nucleotides, cofactors, metal ions, buffers, and the like. Methods for prepositioning reagents in a microfluidic device have been described (see McBride et al., supra). In addition, detection reagents such as labeled probes can be provided by prepositioning and/or combining.

To produce amplicons the environment of the MPD reaction chambers is manipulated as required to accomplish amplification by the amplification method selected. For example, thermocycling necessary for a PCR-type amplification reaction can be accomplished by placing the device on a thermocycling plate and cycling the device between the various required temperatures for melting of the DNA duplex (either target or amplicon), annealing of primers, and DNA synthesis. For example a protocol with an initial ramp to 95° C. and maintain for 1 m; three step thermocycling for 40 cycles [92° C. for 30 s, 54° C. for 30 s, and 72° C. for 1 m] or two step thermocycling for 40 cycles [92° C. for 30 s and 60° C. for 60 s] can be used. A variety of thermocycling plates are available from commercial sources, including for example the ThermoHybaid Px2 (Franklin, Mass.), MJ Research PTC-200 (South San Francisco, Calif.), Eppendorf Part# E5331 (Westbury, N.Y.), Techne Part#205330 (Princeton, N.J.).

Although in some cases a single target sequence in the sample is amplified, more often at least 2, at least 3, at least 5, at least 10, at least 20, at least 30, at least 40, at least 50, or at least 100 different target sequences are amplified. Thus, in some embodiments, sufficient reagents are provided to amplify more than one target sequence.

Thus, the amplification procedure can produce from zero (if no target sequence is present) to 100 or more different amplicons. Any particular chamber may have zero, one or more than one amplicons species (where amplicons corresponding to the same target sequence are of the same "species") depending on the nature of the assay and sample.

Usually, at least about $10^3$, at least about $10^4$, at least about $10^5$, at least about $10^6$, at least about $10^7$, or at least about $10^8$ amplicon molecules are produced corresponding to some or all of the target sequences present in the sample. Most typically, from about $10^7$ to about $10^9$ amplicon molecules are produced for each target sequence, although the number may be lower when multiple reactions are conducted in a single reaction chamber.

iv) Detection of Amplicons

The amplicon products can be detected in individual chambers and/or they can be pooled for subsequent detection and analysis (as described below in Section C(vi)). That is, amplicons can be detected and then pooled, pooled without previously being detected, or detected and not subsequently pooled.

Amplicons can be detected and distinguished (whether isolated in a reaction chamber or at any subsequent time) using routine methods for detecting nucleic acids. Amplicons comprising double-stranded DNA can be detected using intercalation dyes such as SYBR™, Pico Green (Molecular Probes, Inc., Eugene, Oreg.), ethidium bromide and the like (see Zhu et al., 1994, *Anal. Chem.* 66:1941-48) and/or gel electrophoresis. More often, sequence-specific detection methods are used (i.e., amplicons are detected based on their nucleotide sequence). Examples of detection methods include hybridization to arrays of immobilized oligo or polynucleotides, and use of differentially labeled molecular beacons or other "fluorescence resonance energy transfer" (FRET)-based detection systems. FRET-based detection is a preferred method for detection. In FRET-based assays a change in fluorescence from a donor (reporter) and/or acceptor (quencher) fluorophore in a donor/acceptor fluorophore pair is detected. The donor and acceptor fluorophore pair are selected such that the emission spectrum of the donor overlaps the excitation spectrum of the acceptor. Thus, when the pair of fluorophores are brought within sufficiently close proximity to one another, energy transfer from the donor to the acceptor can occur and can be detected. A variety of assays are known including, for example and not limitation, template extension reactions, quantitative RT-PCR, Molecular Beacons, and Invader assays, these are described briefly below.

FRET and template extension reactions utilize a primer labeled with one member of a donor/acceptor pair and a nucleotide labeled with the other member of the donor/acceptor pair. Prior to incorporation of the labeled nucleotide into the primer during an template-dependent extension reaction, the donor and acceptor are spaced far enough apart that energy transfer cannot occur. However, if the labeled nucleotide is incorporated into the primer and the spacing is sufficiently close, then energy transfer occurs and can be detected. These methods are particularly useful in conducting single base pair extension reactions in the detection of single nucleotide polymorphisms and are described in U.S. Pat. No. 5,945,283 and PCT Publication WO 97/22719.

Quantitative Real Time PCR. A variety of so-called "real time amplification" methods or "real time quantitative PCR" methods can also be used to determine the quantity of a target nucleic acid present in a sample by measuring the amount of amplification product formed during or after the amplification process itself. Fluorogenic nuclease assays are one specific example of a real time quantitation method which can be used successfully with the devices described herein. This method of monitoring the formation of amplification product involves the continuous measurement of PCR product accumulation using a dual-labeled fluorogenic oligonucleotide probe—an approach frequently referred to in the literature as the "TaqMan" method. See U.S. Pat. No. 5,723,591

Molecular Beacons: With molecular beacons, a change in conformation of the probe as it hybridizes to a complementary region of the amplified product results in the formation of a detectable signal. The probe itself includes two sections: one section at the 5' end and the other section at the 3' end. These sections flank the section of the probe that anneals to the probe binding site and are complementary to one another. One end section is typically attached to a reporter dye and the other end section is usually attached to a quencher dye. In solution, the two end sections can hybridize with each other to form a hairpin loop. In this conformation, the reporter and quencher dye are in sufficiently close proximity that fluorescence from the reporter dye is effectively quenched by the quencher dye. Hybridized probe, in contrast, results in a linearized conformation in which the extent of quenching is decreased. Thus, by monitoring emission changes for the two dyes, it is possible to indirectly monitor the formation of amplification product. Probes of this type and methods of their use are described further, for example, by Piatek et al., 1998, Nat. Biotechnol. 16:359-63; Tyagi, and Kramer, 1996, Nat. Biotechnology 14:303-308; and Tyagi, et al., 1998, Nat. Biotechnol. 16:49-53 (1998).

Scorpion: The Scorpion detection method is described, for example, by Thelwell et al. 2000, Nucleic Acids Research, 28:3752-3761 and Solinas et al., 2001, "Duplex Scorpion primers in SNP analysis and FRET applications" Nucleic Acids Research 29:20. Scorpion primers are fluorogenic PCR primers with a probe element attached at the 5'-end via a PCR stopper. They are used in real-time amplicon-specific detection of PCR products in homogeneous solution. Two different formats are possible, the 'stem-loop' format and the 'duplex' format. In both cases the probing mechanism is intramolecular. The basic elements of Scorpions in all formats are: (i) a PCR primer; (ii) a PCR stopper to prevent PCR read-through of the probe element; (iii) a specific probe sequence; and (iv) a fluorescence detection system containing at least one fluorophore and quencher. After PCR extension of the Scorpion primer, the resultant amplicon contains a sequence that is complementary to the probe, which is rendered single-stranded during the denaturation stage of each PCR cycle. On cooling, the probe is free to bind to this complementary sequence, producing an increase in fluorescence, as the quencher is no longer in the vicinity of the fluorophore. The PCR stopper prevents undesirable read-through of the probe by Taq DNA polymerase.

Invader: Invader assays (Third Wave Technologies, Madison, Wis.) are used particularly for SNP genotyping and utilize an oligonucleotide, designated the signal probe, that is complementary to the target nucleic acid (DNA or RNA) or polymorphism site. A second oligonucleotide, designated the Invader Oligo, contains the same 5' nucleotide sequence, but the 3' nucleotide sequence contains a nucleotide polymorphism. The Invader Oligo interferes with the binding of the signal probe to the target nucleic acid such that the 5' end of the signal probe forms a "flap" at the nucleotide containing the polymorphism. This complex is recognized by a structure specific endonuclease, called the Cleavase enzyme. Cleavase cleaves the 5' flap of the nucleotides. The released flap binds with a third probe bearing FRET labels, thereby forming another duplex structure recognized by the Cleavase enzyme. This time the Cleavase enzyme cleaves a fluorophore away from a quencher and produces a fluorescent signal. For SNP genotyping, the signal probe will be designed to hybridize with either the reference (wild type) allele or the variant (mutant) allele. Unlike PCR, there is a linear amplification of signal with no amplification of the nucleic acid. Further details sufficient to guide one of ordinary skill in the art are provided by, for example, Neri, B. P., et al., *Advances in Nucleic Acid and Protein Analysis* 3826:117-125, 2000) and U.S. Pat. No. 6,706,471.

Padlock probes: Padlock probes (PLPs) are long (e.g., about 100 bases) linear oligonucleotides. The sequences at the 3' and 5' ends of the probe are complementary to adjacent sequences in the target nucleic acid. In the central, non-complementary region of the PLP there is a "tag" sequence that can be used to identify the specific PLP. The tag sequence is flanked by universal priming sites, which allow PCR amplification of the tag. Upon hybridization to the target, the two ends of the PLP oligonucleotide are brought into close proximity and can be joined by enzymatic ligation. The resulting product is a circular probe molecule catenated to the target DNA strand. Any unligated probes (i.e., probes that did not hybridize to a target) are removed by the action of an exonuclease (which may be introduced before or after a pooling step). Hybridization and ligation of a PLP requires that both end segments recognize the target sequence. In this manner, PLPs provide extremely specific target recognition.

Using universal primers, the tag regions of circularized PLPs can be amplified and resulting amplicons detected. For example, TaqMan real time PCR can be carried out to detect and quantitate the amplicon. The presence and amount of amplicon can be correlated with the presence and quantity of target sequence in the sample. For descriptions of PLPs see, e.g., Landegren et al., 2003, Padlock and proximity probes for in situ and array-based analyses: tools for the post-genomic era, *Comparative and Functional Genomics* 4:525-30; Nilsson et al., 2006, Analyzing genes using closing and replicating circles *Trends Biotechnol.* 24:83-8; Nilsson et al., 1994, Padlock probes: circularizing oligonucleotides for localized DNA detection, *Science* 265:2085-8.

v) Detection of Multiple Different Target Nucleic Acid Sequences Using the "Universal Amplification" Method As described above, a variety of multiplex amplification systems can be used in conjunction with the present invention. In one type, several different targets can be detected simultaneously by using multiple differently labeled probes each of which is designed to hybridize only to a particular target. Since each probe has a different label, binding to each target to be detected based on the fluorescence signals. By judicious choice of the different labels that are utilized, analyses can be conducted in which the different labels are excited and/or detected at different wavelengths in a single reaction. See, e.g., Fluorescence Spectroscopy (Pesce et al., Eds.) Marcel Dekker, New York, (1971); White et al., Fluorescence Analysis: A Practical Approach, Marcel Dekker, New York, (1970); Berlman, Handbook of Fluorescence Spectra of Aromatic Molecules, 2nd ed., Academic Press, New York, (1971); Griffiths, Colour and Constitution of Organic Molecules, Academic Press, New York, (1976); Indicators (Bishop, Ed.). Pergamon Press, Oxford, 19723; and Haugland, Handbook of Fluorescent Probes and Research Chemicals, Molecular Probes, Eugene (1992).

Conventional multiplex fluorescence detection using many different probes is limited, however, by fluorescence background because probe concentration must be high enough to allow detection of many different probes (i.e., one for each sequence to be detected). Combining many probes results in fluorescence that is the sum of all the probes. This also results in a fluorescence background that is the sum of the background from all of the probes. This background may be so high as to interfere with detection of the reaction product(s). An alternative approach, referred to as the Universal Amplification ("UA") method uses multiple sets of primer pairs, referred to here as "UA primer" amplification in a PCR-type reaction. Universal amplification allows many different sequences in a sample to be amplified using a single reaction mixture, with lower background and cost than conventional systems, and is particularly well suited for use with an MPD.

UA primers can be used to determine whether or not any one or more of a number of different target nucleic acid sequences are present in a sample (without necessarily identifying which of the several target sequences is present). If the assay indicates that at least one of the different nucleic acid sequences is present in the sample, subsequent analysis can be conducted to determine which of the different sequences is present. Such two-step analysis is advantageous in many applications. For example, using the present invention, in a first step a sample can be assayed to determine whether any of 100 (for example) different pathogenic agents is present in the sample. If it is determined in the first step that at least one pathogenic agent is present, the sample can be subjected to further analysis to identify and characterize the particular pathogen.

In one aspect the invention provides a method for detecting multiple amplification products (i.e., amplicons) using the Universal Amplification method. The total number of target sequences detected is usually at least two, and is sometimes at least 5, more often at least 10, at least 20 or at least 30. In some embodiments the total number of target sequences is between 2 and 100, between 5 and 100, between 10 and 100, between 20 and 100, or between 30 and 100. In some embodiments the total number of target sequences is between 2 and 50, between 5 and 50, between 10 and 50, between 20 and 50, or between 30 and 50. In some embodiments the total number of target sequences is more than 100. The UA method makers use of three or more types of primers:

The Type 1 primer has the structure 5'-$U_F$-$B_X F_N$-3' where $U_F$ is a universal forward primer sequence, $B_x$ is a sequence recognized by a detectable (e.g., detectably labeled) probe, Probe X, and F is a forward primer sequence specific to a target sequence N so that $F_1$ is primer for a first target sequence, $F_2$ is a primer sequence for a second target sequence, and so on. Probe X can be a molecular beacon, Taqman-type probe, or other probe (such as, but not limited to, those described above) that specifically binds or hybridizes to sequence B.

The Type 2 primer has the structure 5'-$U_R$-$R_N$-3' where $U_R$ is a universal reverse primer sequence and $R_N$ is a primer specific to a target sequence N so that $R_1$ is primer for a first target sequence, $R_2$ is a primer for a second target sequence and so on. $U_R$ may or may not be the same sequence as $U_F$. In one embodiment, 5'-$U_R$-3' has the same sequence as 5'$U_F$-3'.

The Type 3 primer comprises the sequence 5'-$U_F$-3' (or 5'-$U_1$-3').

The Type 4 primer comprises the sequence 5'-$U_R$-3' (or 5'-$U_2$-3').

Each pair of Type 1 and Type 2 primers is specific to a particular target. The cognate pair of primers that amplify the same target is a "UA primer pair." Thus, if there are 20 target sequences to be detected (for example, sequences corresponding to 20 different pathogens) twenty different primer pairs can be prepared, i.e., 5'-$U_1$-$B_x$-$F_{[1 \to 20]}$-3' and 5'-$U_2$'-$R_{[1 \to 20]}$-3'. The various pairs of Type 1 and Type 2 primers are combined at low concentrations with the sample, and Type 3 and Type 4 primers are added at a higher concentration. During the initial rounds of amplification, the Type 1 and Type 2 primers will amplify any target sequences present in a sample or sub-sample. It will be appreciated that $U_1$ and $U_2$ sequences can be designed with sequences not present (or unlikely to be present) in the initial sample nucleic acid, to avoid amplification of non-target sequences in the sample. For example, for analysis of human DNA, $U_1$ and $U_2$ can be selected to have sequences not found on the human genome. During subsequent rounds of amplification, the amplification products generated in the first rounds of amplification are themselves amplified by the Type 3 and Type 4 primers. The resulting double stranded amplification products will have the structure (showing one strand):

5'-$U_1$-$B_x$-$F_1$-target sequence1-$R_1$'-$U_2$'-3'

5'-$U_1$-$B_x$-$F_2$-target sequence2-$R_2$'-$U_2$'-3'

5'-$U_1$-$B_x$$F_3$-target sequence3-$R_3$'-$U_2$'-3'

5'-$U_1$-$B_x$-$F_4$-target sequence4-$R_4$'-$U_2$'-3'

5'-$U_1$-$B_x$-$F_5$-target sequence5-$R_5$'-$U_2$'-3'

5'-$U_1$-$B_x$-$F_6$-target sequence6-$R_6$'-$U_{2\alpha}$'-3' etc.

where $U_1$' is the complement of $U_1$ and $U_2$' is the complement of $U_2$. Each of the amplification products shown above can be detected by a probe (e.g., molecular beacon, Invader probe, Scorpion probe) that hybridizes to $B_x$. Thus, using the UA universal probes described herein, a multiplicity of target sequences can be detected using a single probe. Most of the amplification steps involve amplification using a single primer (if $U_1$ and $U_2$ are the same) or primer pair. Methods for designing probes that recognize a specified sequence (e.g., $B_x$ are well known. For example, Molecular Beacons can be designed as described in Marras et al., 2003, Genotyping single nucleotide polymorphisms with molecular beacons. In Kwok, P.Y. (ed.), Single nucleotide polymorphisms: methods and protocols. The Humana Press Inc., Totowa, N.J., Vol. 212, pp. 111-128. Molecular Beacons can also be designed with the help of a dedicated software package called 'Beacon Designer,' which is available from Premier Biosoft International (www.premierbiosoft.com). However, it will be appreciated that the sequence of $B_x$ can be, and generally is, an artificial sequence (i.e., not found in the in the initial sample nucleic acid) that can be recognized by the probe.

Primer concentration(s) will vary with the length, composition, and nature of the sample and targets. Those primer pairs with sequences specific to each of the targets (e.g., Type 1 and 2 primers) are required only in the first few rounds of amplification and can be provided in very small quantities (for example and not limitation, e.g., typically less than about 50 nM, more often less than about 30 nM and sometimes less than about 20 nM). Type 3 and 4 primers can be provided at somewhat higher concentration (for example and not limitation, e.g., typically from about 100 nM to 1 uM, such as from about 200 nM to about 900 nM). The practicioner guided by this disclosure will be able to select appropriate concentration using routine methods.

The method can be modified in a variety of ways to achieve particular results. In one version of the method, a relatively small number of probe sequences can be used with a larger number of unique target sequences, with different classes of target specific sequences associated with differently labeled probes. For example, if target sequences 1-20 are characteristic of a viral pathogen, target sequences 21-40 are characteristic of a bacterial pathogen, and target sequences 41-45 are positive control sequences (human genes), amplification of a human patient sample could give zero, one or more than one of the following 45 amplification products:

Set 1: 20 products (from 5'-$U_F$-$B_V$-target sequence1-$U_R$'-3' to 5'-$U_F$-$B_V$-target sequence20-$U_R$'-3')

Set 2: 20 products (from 5'-$U_F$-$B_B$-target sequence21'-$U_R$-3' to 5'-$U_F$-$B_B$-target sequence40-$U_R$'-3')

Set 1: 5 products (from 5'-$U_F$-$B_C$-target sequence41'-$U_R$'-3' to 5'-$U_F$-$B_C$-target sequence45-$U_R$'-3')

By using differently labeled probes $B_V$ (hybridizes to Set 1 products), $B_B$ (hybridizes to Set 2 products), and $B_C$ (hybridizes to Set 3 products) the classes of amplification products can be detected and distinguished. Thus, if the human sample produced any amplicon to which Probe $B_V$ hybridized and emitted signal it would indicate that the patient was infected with one of 20 viruses. If desired, the precise identity of the viral pathogen could be determined in a second assay step. Similarly, if the human sample produced any amplicon to which Probe $B_B$ hybridized and emitted signal (different from the signal emitted by Probe $B_V$) it would indicate that the patient was infected with one of 20 bacteria. Other types of samples, such as food or agricultural sample can be screened for many different pathogens simultaneously and if any hits are detected the sample can be selected for further analysis to determine which of the many pathogen(s) was responsible for the signal. If there is no signal, the sample can be concluded to be pathogen free.

Numerous primer pairs are know for detection and analysis of pathogens, and other primer combinations can be prepared using well established methods. For illustration and not limitation see, e.g., U.S. Pat. No. 6,503,722 "Detection of toxigenic strains of *Clostridium difficile* using a PCR-based assay" [e.g., 5'CCCCAATAGAAGATTCAATATTAAG

[SEQ ID NO.: 1] with 5'ATGTAGAAGTAAACTTACT TGGATG [SEQ ID NO.: 2] to detect strains expressing toxin A; 5' GGTGGAGCTTCAATTGGAGAG [SEQ ID NO.: 3] with 5' GTGTAACCTACTTTCATAACACCA [SEQ ID NO.: 4] to detect strains expressing toxin B; and 5' AAGT-GTTCTGTAACAGGTATACC [SEQ ID NO.: 5] with 5' GGTCCATTAGCAGCCTCACA [SEQ ID NO.: 6] to detect glutamate dehydrogenase (positive control for presence of bacteria)]; U.S. Pat. No. 6,723,505 "Method for identification of the indicators of contamination in liquid samples"; U.S. Pat. No. 6,632,642 "Genes for detecting bacteria and detection method by using the same"; U.S. Pat. No. 6,387,652 "Method of identifying and quantifying specific fungi and bacteria"; U.S. Pat. No. 6,013,435 "Drug resistance screening method using multiplex amplification"; U.S. Pat. No. 5,932,415 "Processes and agents for detecting listerias"; U.S. Pat. No. 6,225,094 "Method for the genus-specific or/and species-specific detection of bacteria in a sample liquid"; Di Pinto, 2005, A collagenase-targeted multiplex PCR assay for identification of *Vibrio alginolyticus, Vibrio cholerae,* and *Vibrio parahaemolyticus*", *J Food Prot.* 68(1):150-3; Maher et al., 2003, "Use of PCR to detect *Campylobacter* species in samples" *J. Clin. Micro.* 41(7):2980 [5' AGTCGTAACA AGGTAGCCG [SEQ ID NO.: 7] with 5' CYRYTGCCAAG-GCATCCACC] [SEQ ID NO.: 8]; Lim et al., "Use of PCR to detect *heliobacter pylori* in gastric mucosa of patients" *J. Clin. Micro.* 41(7):3387 [5' ACTTTAAACGCATGAA-GATAT [SEQ ID NO.: 9] with 5' ATATTTTGACCT-TCTGGGGT] [SEQ ID NO.: 10]; and Wilson et al., 2003, "Use of PCR to detect *Legionella pneumophila*" *J. Clin. Micro.* 41(7):3327 [5' GCAATGTCAACAGCAA [SEQ ID NO.: 11] with 5' CATAGCGTCTTGCATG] [SEQ ID NO.: 12].

Although the "Universal Amplification" method described above is suited for use in MPD-based analyses, it will be appreciated that this method can be used in a variety of formats (both microfluidic and nonmicrofluidic).

vi) Pooling of Amplicons

In some embodiments of the invention, following amplification and optional detection of amplicons, the contents of the sub-samples, including any amplicons in them, are pooled (i.e., allowed to combine or mix at least partially). Pooling combines the amplicons (if present) from multiple sub-samples. Pooling can be accomplished by, for example, opening the valves of an elastomeric microfluidic device in which partitioning and amplification occurred such that the contents of multiple sub-samples (e.g., at least about $10^3$, at least about $5\times10^3$, at least about $10^4$, at least about $2\times10^4$, at least about $3\times10^4$, or at least about $10^5$ sub-samples) are in fluidic communication with each other, constituting a "post-amplification sample" that consists of the contents of all of the chambers. Amplicons can mix by diffusion, which can be accelerated using thermal, mechanical, acoustic, or chemical energy. In one embodiment, pooling occurs primarily as a result of active mixing (e.g., by pumping the fluid through flow channels in the device using a rotary peristaltic pump or other mechanism). Alternatively or in combination with the methods above, a portion, all or substantially all of the post-amplification sample can be pumped out of or otherwise withdrawn from the device, thereby pooling and mixing any amplicons present in the sample. Any method that results in a distribution of amplicons sufficient to carry out subsequent detection steps may be used.

It is not necessary that the various amplicons diffuse (or are mixed) to equilibrium in the post-amplification sample, but it is desirable that sufficient mixing occur so that an aliquot of post-amplification sample contains a number of molecules of each amplicon (e.g., at least 10, at least 100, at least 1000, or at least 5000 molecules) from each sub-sample in which amplicons were produced. For illustration, consider carrying out an amplification reaction that produces 100,000 copies of each of three distinct amplicons, i.e., amplicon A in chamber 1, amplicon B in chamber 2, and amplicon C in chamber 3. The sub-samples are pooled (by releasing valves) and one-fifth of the volume of the post-amplification sample removed from the device or from the partition region of the device (see Section C (viii), below). If the amplicons had diffused to equilibrium in the post-amplification sample, and assuming no loss of material, the one-fifth volume would contain about 20,000 molecules of each of the three amplicons. If diffusion was less than complete, the one-fifth volume could contain unequal amounts of each amplicon, for example 50,000 molecules of amplicon A, 20,000 molecules of amplicon B and 15,000 molecules of amplicon C.

Alternatively, all or substantially all, of the post-amplification sample (or substantially all of it) can be withdrawn from the device, thereby mixing any amplicons present in the sample.

vii) Subsequent Analysis of Amplicons

Following pooling (e.g., diffusion and/or mixing) all or a portion of the amplicon pool can be used for subsequent analyses. Typically the amplicon pool is divided into a plurality of aliquots and each aliquot separately analyzed to determine a property (e.g., a nucleotide sequence or the presence or absence of a predetermined nucleotide sequence) of an amplicon or amplicons in that aliquot. If desired, the volume of the amplicon pool can be increased by addition of a suitable solution such as aqueous buffer or a reaction mixture containing amplification and/or detection reagents. The amplicon pool can be divided into aliquots manually or can be divided using an appropriately designed MPD (see Section C (viii), below).

It will be apparent from the discussion above that each of the aliquots from the amplicon pool will contain essentially the same set of amplicons (i.e., the same amplicon species will be represented in each aliquot). Each of the aliquots can be used for a different analysis. For example, a first aliquot can be assayed for the presence of a first target sequence (e.g., a first SNP in an amplified gene sequence), a second aliquot can be assayed for the presence of a second target sequence (e.g., a second SNP in the same amplified gene sequence), a third aliquot can be assayed for the presence of a third target sequence (e.g., a first SNP of a different amplified gene) and so on. It will be appreciated that target sequences of interest are not limited to SNPs.

The subsequent analysis of amplicons can be carried out using any desired technique including, without limitation, hybridization to a target nucleic acid or array of targets, PCR amplification, FRET-assays, hybridization to probes, and the like.

viii) Devices

Figure 2:
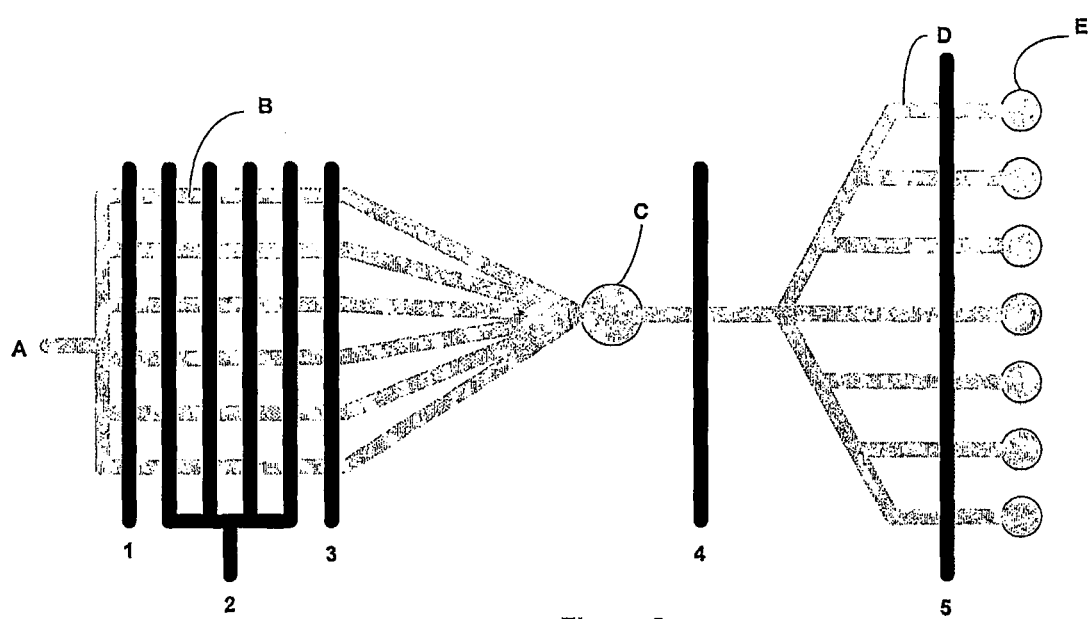
FIG. 2 shows an exemplary design of a MPD with two banks: a first bank in which nucleic acids are partitioned and amplified in individual chambers, and a second bank in which subsequent analysis of the amplicon pool occurs.

As noted above, massive partitioning is accomplished using an elastomeric MPD. Subsequent analyses can also be accomplished using any suitable assay. In certain embodiments, an elastomeric microfluidic device is used for subsequent analyses. In some embodiments the initial partitioning and amplification, the subsequent mixing of applications, and the subsequent analysis of amplicons are carried out using different sections (i.e., different banks) of the same the same device. For example, an elastomeric device can be fabricated with three regions: a first region that is a MPD in which target sequences, cells or molecules are amplified in individual chambers to produce amplicons and then allowed to mix to produce an amplicon pool, a second region (which can be as small as a single flow channel) by which the amplicon pool is transferred to the third region, and a third region having a plurality of flow channels with a region of each flow channel defining a reaction site in which subsequent analysis of the amplicon pool occurs. In one embodiment, the flow channels in the third region are blind flow channels with reaction sites near the channel terminus. A schematic of an exemplary device is shown in FIG. 2. In this schematic five control channels (1, 2, 3, 4 and 5) are shown in black. A branched flow channel system is shown in gray. It will be appreciated, as discussed above, that the flow channel configuration need not be branched. In the device shown, a sample containing an amplification mixture and nucleic acids is injected into inlet A with the values formed by control channels 1 and 2 open, and control channel 3 actuated (closed). Control channel 2 is then actuated to isolate the sample in multiple chambers (B). The samples are then subject to thermocycling and optionally detection of the amplification products (e.g., using a commercially available fluorescence reader). Control channel 1 is then closed and control channel 2 opened to allow mixing of amplicons in the various chambers to produce an amplicon pool, a portion of which is then pumped into blind channels (D) with control channels 3, 4 (if present) and 5 open. Alternatively, control channels 2 and 3 are both opened and a portion of the amplicon pool is pumped to a mixing chamber (C) with control channel 4 closed. Control channel 3 is then closed and channels 4 and 5 are opened and portion of the amplicon pool is pumped into blind channels (D). Control channel 5 is then closed isolating blind reaction chambers (E) and the subsequent round of analysis takes place.

In one embodiment the device is configured so that reagents can be added to the pooled amplicon sample; for example, the mixing chamber (C) shown in FIG. 2 may be fluidically linked to a reservoir containing reagents (e.g., nuclease, probes or primers) that can be added prior to distributing the amplicon pool into a reaction chambers.

ix) Systems

In one aspect, the invention provides a system for analysis of nucleic acids, proteins or cells comprising a massively partioning device and an external collection reservoir for collection of an amplicon pool. The external reservoir can be any type of container or tube that is fluidically connected to the MPD, so that the contents of the MPD chambers can be transferred from the MPD to the reservioir. Transfer can be by displacement of the MPD contents using a displacement fluid, by active pumping, or by other means.

In one aspect, the invention provides a system for analysis of nucleic acids, proteins or cells comprising a massively partitioning device, optionally including an integral or external reservoir for collection of an amplicon pool, and an (additional) external component. In one embodiment the MPD includes a region with a plurality of flow channels defining a reaction sites for subsequent analysis of the amplicon pool aliquots (e.g., the "third" region of the device described above in Section (viii).

In one aspect, the invention provides a system for analysis of nucleic acids, proteins or cells comprising a massively partitioning device as described in Section (viii) above, where the MPD has three regions: a first region that is a MPD in which target sequences, cells or molecules are amplified in individual chambers to produce amplicons and then allowed to mix to produce an amplicon pool, a second region (which can be as small as a single flow channel) by which the amplicon pool is transferred to the third region, and a third region having a plurality of flow channels with a region of each flow channel defining a reaction site in which subsequent analysis of the amplicon pool occurs.

Additional external components of the system may include sensors, actuators (e.g., pumps; see U.S. Pat. No. 6,408,878), control systems for actuating valves, data storage systems, reagent storage units (reservoirs), monitoring devices and signal detectors Signal detectors may detect visible, fluorescent, and UV light (intensity, scattering, absorption) luminescence, differential reflectivity, electrical resistance, resistivity, impedance, or voltage, in chambers or reaction sites. In one embodiment the external component is a temperature control component such as a thermocycler (e.g., Peltier device, resitive heaters, and heat exchangers; see e.g., U.S. Pat. No. 6,960,437 B2).

In one aspect, the invention provides a system for analysis of nucleic acids, proteins or cells comprising a massively partitioning device, optionally including an integral or external reservoir for collection of an amplicon pool, optionally including a plurality of flow channels defining a reaction sites for subsequent analysis of the amplicon pool aliquots, and optionally including and an additional reagent positioned in the chambers of the MPD and/or the reaction sites for subsequent analysis of the amplicon pool aliquots. Exemplary additional reagents include enzymes (e.g., nuclease, polymerase, or ligase); primers and probes (PCR primers, molecular beacons, padlock probes, proximity ligation probes, Universal Amplification primers), amplification reagents and the like.

For illustration and not limitation, particular systems may comprise an MPD and a heat source (e.g., thermocycler) positioned to regulate the temperature of the contents of reaction chambers. In one embodiment, heat is transmitted from the heat source to the MPD by conduction (e.g., the heat source being adjacent and in contact with the MPD). In one embodiment the MPD is fixed (e.g., clamped) to the heat source.

For illustration and not limitation, particular systems may comprise an MPD and a signal detector positioned to detect signal emanating from reaction chambers in the MPD system. In one embodiment, a fluorescent signal is detected. In one embodiment the system includes an appropriately programmed computer coupled to the signal detector capable of storing information such as the position, intensity and/or duration of a signal emanating from reaction chambers in the MPD system.

For example, when the MPD comprises reaction chambers for analysis of amplicon pool aliquots, the signal detector, heat source, or other component of the system may be associated with those reaction chambers, reaction chambers produced in the partitioning step, or both. Other particular systems may comprise a MPD comprising prepositioned reagents in one or more reaction chambers or mixing chambers.

x) Illustrative Examples

The following prophetic examples are intended to illustrate aspects of the invention. However, they are for illustration only and are not intended to limit the invention in any fashion.

1. SNP Analysis

In this illustration, 200 different genes of an individual are screened for the presence of mutations.

A sample containing genomic DNA from the subject is obtained. A small number of genome equivalents is sufficient for analysis. Thus the sample may be from a small number of cells (for example, fewer than 10 cells, and as few as one cell) which may be treated to release and fragment genomic DNA. Alternatively isolated or purified DNA may be used. Usually the DNA is fragmented by shearing, enzymatic or chemical cleavage, or other methods known in the art. In one embodiment the DNA is sheared by transport through a channel with varying cross-dimensions.

The reagents for amplification of target sequences are added to the sample. The amplification reagents include the following:

a) Primer pairs for each of the 200 gene segments to be analyzed. The primer pairs can be selected, for example, to (i) amplify a target polymorphic site sequence only if site has a particular sequence (i.e., a specified SNP allele is present) or (ii) amplify the target polymorphic site sequence using primers that flank the SNP site, so that the segment is amplified without regard to what SNP is present. Each primer pair includes both a target specific sequence and one of two 5' universal sequences shared by all of the forward or all of the reverse primers, allowing all of the amplicons produced using the target specific primers to be amplified with the same universal primers.

b) A pair of universal primers capable of amplifying all of the amplicons produced using the target specific primers.

Primers are selected so that all of the first round amplifications (using target specific primers) can occur under the same reaction conditions.

c) Amplification reagents (polymerase, cofactors, nucleotides, metal ions, buffer, etc.). The reagents may be added to the sample before partition, may be prepositioned in the reaction chambers, or some reagents may be added and others prepositioned.

The sample is injected into the partitioning channel system of a MPD having 40,000 chambers. After injection of the sample, valves are closed creating 40,000 isolated reaction chambers. Each reaction chamber contains all of the probes described above, and some of the chambers contain a nucleic acid molecule with a target sequence of interest as a consequence of the partitioning. The MPD is placed on a thermocycler and cycled using an appropriate protocol (e.g., 2 min at 51° C., 1 sec at 96° C. and 59 sec at 95° C., followed by 40 cycles of 1 min at 58° C., 1 sec at 96° C. and 59 sec at 95° C.). Following amplification, the values are opened and subsamples allowed to mix (e.g., by diffusion or active mixing) producing the amplicon pool.

A portion of the resulting amplicon pool is withdrawn from the MPD and distributed into two hundred (200) aliquots, and each aliquot is subjected to a different SNP assay. Alternatively, different sets of SNP assays can be conducted using multiplex methods. The individual SNP assays can be carried out using, for example, a Taqman™-type probe, Molecular Beacon, Scorpion, or other detection methods and detected using a fluorescence detector.

2. Analysis of Many Sequences Using Nucleic Acids from a Single Cell or Very Few Cells In one embodiment, a nucleic acid analysis is conducted on a single cell. Such an analysis is useful for diagnostic or prognostic methods when tissue is limited such as, for example, genetic testing of a single blastocyst of a pre-implantation embryo produced using in vitro fertilization techniques. Such testing is also useful in the study or cloning of non-human animals. For example, blastocyst cells obtained from a non-human animal can be assayed for the presence, expression or characteristics of a transgene or endogenous gene. It can be verified that the genotype or expression profile of the embryo is consistent with the goals of the researcher prior to implantation into a surrogate mother, resulting in savings of time and resources. Such testing is also useful in forensic analysis in which very few cells may be available or in which cells must be analyzed individually because a sample is contaminated with cells from multiple sources.

Analysis of nucleic acids of a single cell is illustrated by the flow chart in FIG. 3C. It will be appreciated that the figure is provided to assist the reader in understanding the invention, and is not intended to limit the invention in any fashion.

In this method, the single cell (or small number of cells) is provided in a solution or combined with a solution. The cell is treated to release DNA. Any number of methods for cell lysis (e.g., using sonication, denaturants, etc.) are suitable. If genomic DNA is being analyzed it is fragmented. The desired fragment size will be based on the method of detection of the target sequence and the number of reaction chambers on the chip. The goal is to end up with large enough fragments so that target sequences can be amplified (typically >300 bp) and enough fragments so that different amplicons (i.e., amplicons corresponding to different sequences) will be generated is separate reaction chambers. Thus, the intended average size will depend on the number of target sequences to be detected and the number of partitions available. Fragments can be created by restriction digestion or other DNA fragmentation methods. In one embodiment, DNA is sheared by driving it thorough a narrow opening. Thus, a MPD can be designed with a via or flow channel of sufficiently small diameter narrowness to shear DNA to the desired fragment size. In an embodiment the diameter of the via or flow channel varies across its length (e.g., narrow-wide-narrow-wide) to drive the fragmentation. The sample is introduced into a MPD and the MPD valves are actuated to partition the DNA fragments, or RNA molecules, into separate reaction chambers.

Reagents sufficient to amplify each of the target sequences of interest are provided in each reaction chamber. For purposes of this example, assume 50 different loci containing SNPs are of interest, and at each of the 50 polymorphic loci there are two different possible sequences at the SNP site, with the 100 total different target sequences designated SNP 1A, 1B, 2A, 2B, . . . 50A, and 50B. As discussed above, the reagents can be added to the solution containing the intact cell, can be prelocated in the reaction chambers, or some combination of the two. In this example, the amplification reagents include primers sufficient to amplify gene segments spanning each of the 50 loci to produce the SNP site and 40 basepairs of flanking sequence on each side. UA amplification primers may be used. Amplification is then carried out (e.g., by thermocycling if the amplification method is PCR or reverse transcription-PCR). Amplicons are produced in those reaction chambers that contain a nucleic acid molecule (i.e., DNA fragment or RNA molecule) comprising one of the target sequences.

As described above, following amplification the valves are opened and amplicons allowed to mix to produce an amplicon pool. The pool is than divided into 100 different aliquots (optionally using a duel bank MPD as described in Section C (viii), above). In each aliquot a single assay is carried out for an individual SNP using, for example, a Taqman™-type probe, Molecular Beacon, Scorpion, or other detection methods known in the art.

3. Detection of Pathogens Using the UA System

In this illustration, a sample is assayed for the presence of 150 different pathogens. Exemplary samples for the method include (i) a sample is obtained from a patient, (ii) an environmental sample (e.g., from a pond or reservoir) and (iii) a sample from a poultry processing facility.

The reagents for amplification of target sequences are added to the sample. The amplification reagents include the following:

a) Fifty UA primer pairs for gene segments found in fifty different bacterial pathogens. The forward primer of these UA primer pairs includes a recognition site for a molecular beacon labeled with the blue fluorescing dye Cy 5.5.

b) Fifty UA primer pairs for gene segments found in fifty different fungal pathogens. The forward primer of these UA primer pairs includes a recognition site for a molecular beacon labeled with the green fluorescing dye 6-FAM (Fluorescein).

c) Fifty UA primer pairs for gene segments found in fifty different viral pathogens. The forward primer of these UA primer pairs includes a recognition site for a molecular beacon labeled with the red fluorescing dye Cy 3.

d) Type 3 and Type 4 primers corresponding to the UA primer pairs Primers 5'-$U_A$-3' and 5'-$U_B$-3'.

Primer sequences are selected so that all of the UA primer pairs produce amplicons that can be amplified using the same Type 3 and Type 4 primers; and all of the first round amplifications can occur under the same reaction conditions.

e) Molecular beacons that recognize the recognition sites of the three UA forward primers and are labeled as indicated above.

f) Amplification reagents (polymerase, cofactors, nucleotides, metal ions, buffer, etc.). The reagents may be added to the sample before partition, may be prepositioned in the reaction chambers, or some reagents may be added and others prepositioned.

The sample is injected into the partitioning channel system of a MPD having 40,000 chambers. After injection of the sample each valves are closed creating 40,000 isolated reaction chambers. Each reaction chamber contains all of the probes described above, and some of the chambers contain a nucleic acid molecule with a target sequence of interest. The MPD is placed on a thermocycler and cycled using an appropriate protocol (e.g., 2 min at 51° C., 1 sec at 96° C. and 59 sec at 95° C., followed by 40 cycles of 1 min at 58° C., 1 sec at 96° C. and 59 sec at 95° C.). Following amplification, the device is imaged using a commercially available, modified, or custom made fluorescence reader.

The appearance of chambers fluorescening blue indicates that there is at least one bacterial pathogen present in the sample. The appearance of chambers fluorescening green indicates that there is at least one fungal pathogen present in the sample. The appearance of chambers fluorescesing red indicates that there is at least one viral pathogen present in the sample.

If none of the chambers is emits blue, green or red fluorescence when illuminated at the proper wavelengths this is an indication that none of the pathogens tested for are present (typically assays would also include a positive control). If, however, red fluorescence was detected, this would be an indication that a virus is present. Further testing could then be carried out to identify the viral pathogen. For further testing, the values of the MPD are opened and sub-samples allowed to pool by diffusion or active mixing, producing the amplicon pool. A portion of the resulting amplicon pool is withdrawn from the MPD and divided into fifty (50) aliquots each containing reagents for identification of one of the 50 viruses assayed for in the initial part of the screen. An exemplary detection method uses 50 molecular beacons (one in each aliquot) that each recognize a different virus specific sequence in the amplicon. By determining which of the molecular beacons bind a target sequence present in the amplicon pool (or the portion contained in an aliquot) the identity of the pathogen is determined.

4. Additional Applications

It will be appreciated to the reader that the methods of the invention can be used in many applications not specifically described, including, for example and not limitation, detection of gene mutations (substitutions, deletions, translocations, amplifications, etc.) in samples from cancer patients and others. Many of these assays can be carried out without using the optional pooling step and subsequent analysis steps.

D. Partitioning, Detection and Analysis of Proteins and Other Biomolecules

Proteins and other biomolecules can be partitioned in a manner analogous to that described above for nucleic acid molecules. Any suitable method can be used to produce an amplification product indicative of the presence of a protein. In one method, a proximity ligation procedure is used. The proximity ligation procedure is analogous in certain respects to the use of padlock probes, described above in Section C, but is used for detecting proteins and other analytes. The proximity ligation procedure uses specific protein binding agents linked to oligonucleotides. Examples of specific protein binding agents include, but are not limited to, antibodies (defined as any specific binding agent comprising a CDR, including phage display antibodies, single chain antibodies, monoclonal antibodies, and the like) and nucleic acid aptamers. The proximity ligation procedure is described in Landegren et al., 2003, supra; Landegren et al., 2004, Molecular tools for a molecular medicine: analyzing genes, transcripts and proteins using padlock and proximity probes, *J Mol Recognit.* 7:194-7; Gullberg et al., 2004, Cytokine detection by antibody-based proximity ligation, *Proc Natl Acad Sci USA* 101(22):8420-4; Fredriksson et al., 2002, Protein detection using proximity-dependent DNA ligation assays, *Nat Biotechnol.* 20:448-9; and Landegren, 2002, Methods and kits for proximity probing *United States Patent Application* 20020064779. Briefly, a pair of protein binding agents that recognize different epitopes of a target protein are used. Each of the binding agents is attached (e.g., via streptavidin-biotin linkage) to a synthetic DNA strand that includes a PCR primer binding site. The synthetic DNA strands are brought into proximity when both binding agents bind the same target molecule. A connector oligonucleotide that hybridizes to sequences at the ends of both of the synthetic DNAs is added in excess, bringing termini of the DNA strands together so that they can be joined by ligase. In the presence of PCR reagents and primers that recognize the primer binding sites on the two DNA strands, a region of the ligated sequence may be amplified and detected by real time PCR. In contrast, unligated strands are not amplified and therefore not detected in the assay.

It will be appreciated that the assay also may be used to assay for non-protein molecules that are specifically bound by a nucleic acid aptamer, antibody or other binding agent. Proximity ligation methods can also be used to detect nucleic acid targets. In this approach, nucleotide sequences complementary to the target are used rather than protein binding agents.

E. Partitioning of Cells

In another aspect of the invention, individual cells are isolated by partitioning using a MPD, and one or more properties of one or more of the individual cells are determined. Using this method, analysis of individual cells can be carried out without background from other cells in a sample.

Virtually any property of an individual cell can be assayed. For illustration, cell properties include the presence or absence of a target nucleic acid sequence in the cell (where the nucleic acid is RNA or DNA; recombinant or naturally occurring; cellular or viral; nuclear, cytoplasmic or from an organelle);

the presence or absence of a protein or epitope in the cell or on the cell surface;

secretion by the cell of a protein or non-protein molecule, for example in response to a stimulus;

metabolic reactions or changes in cell metabolism, for example in response to a stimulus;

other properties of cells (which will be recognized by those of skill in the art);

combinations of two, three, or more than three different properties (e.g., the presence in a cell of two different target nucleic acid sequences; the presence in a cell of a target nucleic acid sequence and a protein epitope; a change in a metabolic property of a cell and expression of a nucleic acid sequence in the cell; a cell surface epitope and secretion of a cytokine by the cell in response to a stimulus, etc.).

For this analysis, a liquid sample containing a plurality of separable cells is introduced into the MPD and the cells partitioned. A "separable cell" is a cell that is physically separated from other cells and can be partitioned into a chamber without other cells. In some cases (e.g., blood cells, lymphocytes, spermatocytes, oocytes, yeast, certain bacteria or other microorganisms) seperable cells can be obtained from a patient or other source with little processing. In other cases (e.g., liver biopsy, cultured cells, blastocyte) it will be necessary to disrupt a tissue or aggregate mechanically, enzymatically, or using other methods well known in the art. See, e.g., Ausubel et al., 2004, Current Protocols In Molecular Biology, Greene Publishing and Wiley-Interscience, New York; Chapter 25. Examples of cells that can be assayed in this method include eukaryotic cells, human cells, animal cells, plant cells, fetal cells, embryonic cells, stem cells, blood cells, lymphocytes, bacterial cells, recombinant cells and cells infected with a pathogen. Further, although this section describes analysis of cells, the reader will appreciate that the same methods can be used for analysis of other biological entities, such as viruses and organelles.

In one aspect, the method includes partitioning a sample comprising a plurality of seperable cells into at least $10^3$ separate reaction chambers in an MPD, where after partitioning at least two chambers comprise exactly one cell each. Often the sample is partitioned into at least $10^4$ separate reaction chambers, at least $2 \times 10^4$ separate reaction chambers or at least $3 \times 10^4$ separate reaction chambers. The number of cells introduced into the MPD and/or the number of chambers in the MPD are selected so that most or virtually all of the chambers contain either no cells or a single cell. This can be determined from the Poisson distribution (based on the number of chambers in the device and number of cells injected into the device) or empirically (e.g., by detecting the number of chambers that contain cells). Usually at least 90% of the chambers contain zero or one cell, often at least 99% of the chambers contain zero or one cell, and in some cases virtually all of the chambers contain zero or one cell.

Each of the plurality of chambers contains the same reagents for conducting the analysis. All or some of these reagents can added to the sample or cells prior to injection into the device and/or can be prepositioned in the chambers and/or provided in inactive form, as described above. Because the reagents are constant, any chamber-to-chamber differences in analytical results are due to the presence of different cells (or no cell) and reflect differences in the properties of the cells. By detecting different signals from different chambers, a property or properties of cells in chambers can be determined and compared. This method finds a variety of applications in which it is informative to determine that a sample contains a cell having two or more properties detectable in separate assays. This method also finds a variety of applications in which the cell of interest is a rare cell in a background of many other cells.

The nature or type of reagents used will depend on the type of assay contemplated and specific properties to be detected. Generally the properties that can be assayed can be divided into two groups: properties determined based on the presence or absence of a nucleic acid target sequence and properties determined based on something other than the presence or absence of a nucleic acid target sequence. In many applications both a nucleic acid analysis and detection of a different type of property are carried out.

In embodiments in which the analysis of cell properties includes a detecting a nucleic acid sequence (i.e., one, two or more target sequences are detected for an isolated cell) reagents suitable for nucleic acid analysis include those used for nucleic acid amplification (including but not limited to the PCR, SPIA, Invader, and other amplification methods described in this disclosure or known in the art) and those used for detection (including but not limited to, FRET based methods and other detection methods described in this disclosure or known in the art). In one embodiment the UA amplification/detection methods described in Section C (v) are used.

Methods are known in the art for assay of a multitude of cell properties other than or in addition to the characteristics of nucleic acids. For example, proximity ligation and FRET-based assays can be used to detect the presence of proteins or epitopes in a cell; presence, activation or change in enzymatic activities; intracellular organelle function; pathogen (e.g., viral) infection; intracellular signaling; protein-protein interactions; protein-DNA interactions; colocalization of proteins cell cycle; metabolic reactions such as generation of reactive oxygen species; mitochondrial membrane potential; apoptosis; intracellular organelle function; changes in representations of cell types in cell populations; and subcellular localization of macromolecules.

In some embodiments of the invention the cell(s) is destroyed in the course of the process of detecting the cell property. Alternatively, numerous fluorescence based assays that can be carried out on living cells can readily be adapted for use in the present invention and/or reagents used in such assays may be used in the methods of the present invention. See, e.g., Dirks et al., 2003, *Visualizing RNA molecules inside the nucleus of living cells, Methods*, 29:51-7; Santangelo et al., 2004, *Dual FRET molecular beacons for mRNA detection in living cells, Nucleic Acids Res.*, 32:e57; Awais et al., 2004, *A genetically encoded fluorescent indicator capable of discriminating estrogen agonists from antagonists in living cells, Anal Chem.*, 76:2181-6; Nohe et al., 2004, *Analyzing for co-localization of proteins at a cell membrane, Curr Pharm Biotechnol.*, 5:213-20; Thoren et al., 2004, *Membrane binding and translocation of cell-penetrating peptides, Biochemistry*, 43:3471-89; Balaji et al., 2004, *Live cell ultraviolet microscopy: a comparison between two- and three-photon excitation, Microsc Res Tech*, 63:67-71; Gardiner, 2002, *Spatial and temporal analysis of Rac activation during live neutrophil chemotaxis, Curr Biol.*, 12:2029-34; Moshinsky et al., 2003, *A Widely Applicable, High-Throughput TR-FRET Assay for the Measurement of Kinase Autophosphorylation: VEGFR-2 as a Prototype Journal of Biomolecular Screening*, 8:447-452; U.S. Pat. Nos. 4,822,733, 5,622,821, 5,639,615, and 5,656,433 [describing the Invitrogen LanthaScreen™ TR-FRET Kinase Assays for Tyrosine and Serine/Threonine Kinases]; Zhang et al., (2004), *Detection of mitochondrial caspase activity in real time in situ in live cells, Microsc Microanal.*, 10:442-8; Martin-Fernandez et al., 2004, *Aden-* ovirus type-5 entry and disassembly followed in living cells by FRET, fluorescence anisotropy, and FLIM, Biophys J., 87:1316-27; Zorov et al., 2004, Examining intracellular organelle function using fluorescent probes: from animalcules to quantum dots, Circ Res., 95:239-52; Mongillo et al., 2004, Fluorescence resonance energy transfer-based analysis of cAMP dynamics in live neonatal rat cardiac myocytes reveals distinct functions of compartmentalized phosphodiesterases, Circ Res., 95:67-75, Chigaev et al., 2004, Conformational regulation of alpha 4 beta 1-integrin affinity by reducing agents. "Inside-out" signaling is independent of and additive to reduction-regulated integrin activation, J Biol Chem., 279:32435-43; Zaccolo et al., 2004, Use of chimeric fluorescent proteins and fluorescence resonance energy transfer to monitor cellular responses, Circ Res., 94:866-73; Nohe et al., 2004, Analyzing for co-localization of proteins at a cell membrane, Curr Pharm Biotechnol., 5:213-20; Thoren et al., 2004, Membrane binding and translocation of cell-penetrating peptides, Biochemistry, 43:3471-89; Balaji et al., 2004, Live cell ultraviolet microscopy: a comparison between two- and three photon excitation, Microsc Res Tech., 63:67-71; Gardiner, 2002, Spatial and temporal analysis of Rac activation during live neutrophil chemotaxis, Curr Biol., 12:2029-34.

In addition, many cell-based assays developed for use in Laser Scanning Cytometry technology (e.g., CompuCyte Corp., Cambridge, Mass.) can be readily adapted for use in the methods of the invention and/or regents used in such assays may be used in the methods of the present invention. See, e.g., Adams et al., 2004, Increase of Circulating Endothelial Progenitor Cells in Patients With Coronary Artery Disease After Exercise-Induced Ischemia, Arterioscler. Thromb. Vasc. Biol.; Akimitsu et al., 2003, Enforced cytokinesis without complete nuclear division in embryonic cells depleting the activity of DNA topoisomerase IIalpha, Genes Cells, 8:393-402; Amirlak and Couldwell, 2003, Apoptosis in glioma cells: review and analysis of techniques used for study with focus on the laser scanning cytometer, J. Neurooncol., 63:129-45; Balmer et al., 2003, Elevated methyl-CpG-binding protein 2 expression is acquired during postnatal human brain development and is correlated with alternative polyadenylation, J Mol Med., 81:61-8; Baskin et al., 2003, Thimerosal Induces DNA Breaks, Caspase-3 Activation, Membrane Damage, and Cell Death in Cultured Human Neurons and Fibroblasts, Toxicol. Sci., 74:361-368; Beliakoff et al., 2003, Hormone-Refractory Breast Cancer Remains Sensitive to the Antitumor Activity of Heat Shock Protein 90 Inhibitors, Clin Cancer Res., 9:4961-4971; Bocsi et al., 2004, Scanning fluorescent microscopy analysis is applicable for absolute and relative cell frequency determinations, Cytometry, 61A:1-8; Bollmann et al., 2003, Determination of features indicating progression in atypical squamous cells with undetermined significance, Cancer, 99:113-7; Bollmann, et al., 2003, Human papillomavirus typing and DNA ploidy determination of squamous intraepithelial lesions in liquid-based cytologic samples, Cancer, 99:57-62; Braunschweig et al., 2004, X-chromosome inactivation ratios affect wild-type MeCP2 expression within mosaic Rett syndrome and Mecp2−/+ mouse brain, Hum. Mol. Genet., 13:1275-86; Brower, 2003, Evidence of Efficacy: Researchers Investigating Markers for Angiogenesis Inhibitors, J Natl Cancer Inst., 95:1425-1427; Cai et al., 2003, Toxicity of Acetaminophen, Salicylic Acid, and Caffeine for First-Passage Rat Renal Inner Medullary Collecting Duct Cells, J. Pharmacol. Exp. Ther., 306:35-42; Cheng et al., 2003, Immunocytochemical analysis of prostate stem cell antigen as adjunct marker for detection of urothelial transitional cell carcinoma in voided urine specimens, J.

Urol., 169:2094-100; Chung et al., 2003, Tea and Cancer Prevention: Studies in Animals and Humans, J. Nutr., 133: 3268 S-3274S; Claytor et al., 2003, The cleaved peptide of PAR1 is a more potent stimulant of platelet-endothelial cell adhesion than is thrombin, J Vasc Surg., 37:440-5; Crowder et al., 2004, PML mediates IFN{alpha} induced apoptosis in myeloma by regulating TRAIL induction, Blood; Cummins et al., 2003, Persistent Localization of Activated Extracellular Signal-Regulated Kinases (ERK1/2) Is Epithelial Cell-Specific in an Inhalation Model of Asbestosis, Am J Pathol., 162:713-20; D'Amico et al., 2003, The Role of Ink4a/Arf in ErbB2 Mammary Gland Tumorigenesis, Cancer Res., 63:3395-3402; Davis et al. 2003, Automated quantification of apoptosis after neoadjuvant chemotherapy for breast cancer: early assessment predicts clinical response, Clin Cancer Res., 9:955-60; Davis et al., 2003, Surrogate markers in antiangiogenesis clinical trials, Br J Cancer, 89:8-14; Davis, et al., 2003, Antiangiogenic tumor therapy, Biotechniques, 34:1048-50, 1052, 1054 passim; Davis et al., 2004, Quantitative Analysis of Biomarkers Defines an Optimal Biological Dose for Recombinant Human Endostatin in Primary Human Tumors, Clin. Cancer Res., 10:33-42; Denmeade et al., 2003, Prostate-Specific Antigen-Activated Thapsigargin Prodrug as Targeted Therapy for Prostate Cancer, J Natl Cancer Inst., 95:990-1000; Dmitrieva et al., 2003, High NaCl causes Mre11 to leave the nucleus, disrupting DNA damage signaling and repair, Am J Physiol Renal Physiol., 285:F266-274; Dmitrieva et al., 2004, Cells adapted to high NaCl have many DNA breaks and impaired DNA repair both in cell culture and in vivo, PNAS, 101:2317-2322; Doyle et al., 2004, Toll-like Receptors Induce a Phagocytic Gene Program through p38, J. Exp. Med., 199:81-90; Fortunel et al., 2003, Long-term expansion of human functional epidermal precursor cells: promotion of extensive amplification by low TGF-{beta} 1 concentrations, J. Cell Sci., 116:4043-4052; Foster et al., 2004, Laser scanning cytometry for the detection of neoplasia in urologic cytology specimens, Cancer, 102:115-23; Furuta et al., 2003, Phosphorylation of Histone H2AX and Activation of Mre11, Rad50, and Nbs1 in Response to Replication-dependent DNA Double-strand Breaks Induced by Mammalian DNA Topoisomerase I Cleavage Complexes, J. Biol. Chem., 278:20303-20312; Furuya et al., 2004, A Novel Technology Allowing Immunohistochemical Staining of a Tissue Section with 50 Different Antibodies in a Single Experiment, J. Histochem. Cytochem., 52:205-210; Gerstner et al., 2004, Eosinophilia in nasal polyposis: its objective quantification and clinical relevance, Clin Exp Allergy, 34:65-70; Gerstner et al., 2003, Analysis of ploidy in hypopharyngeal cancer by laser scanning cytometry on fine needle aspirate biopsies, Anal Cell Pathol., 25:51-62; Gerstner et al., 2003, Slide-based cytometry for predicting malignancy in solid salivary gland tumors by fine needle aspirate biopsies, Cytometry, 53B:20-5; Gerstner et al., 2004, Quantitative histology by multicolor slide-based cytometry, Cytometry, 59A:210-9; Gniadecki, and Bang, 2003, Flotillas of Lipid Rafts in Transit Amplifying Cell-Like Keratinocytes, J. Invest. Dermatol., 121:522-528; Gniadecki and Rossen, 2003, Expression of T-cell activation marker CD134 (OX40) in lymphomatoid papulosis, Br J. Dermatol., 148:885-91; Greene et al., 2004, Secretory Leucoprotease Inhibitor Impairs Toll-Like Receptor 2- and 4-Mediated Responses in Monocytic Cells, Infect. Immun., 72:3684-3687; Griffin et al., 2003, Neutrophil elastase up-regulates human beta-defensin-2 expression in human bronchial epithelial cells, FEBS Lett., 546:233-6; Gui and Zheng, 2003, Epidermal Growth Factor Induction of Phenotype-dependent Cell Cycle Arrest in Vascular Smooth Muscle Cells Is through the Mitogen-activated Protein Kinase Pathway, J.

Biol. Chem., 278:53017-53025; Haider et al., 2003, *Dual Functionality of Cyclooxygenase-2 as a Regulator of Tumor Necrosis Factor-Mediated G1 Shortening and Nitric Oxide-Mediated Inhibition of Vascular Smooth Muscle Cell Proliferation, Circulation*, 108:1015-1021; Haider et al., 2003, *In vitro model of "wound healing" analyzed by laser scanning cytometry: Accelerated healing of epithelial cell monolayers in the presence of hyaluronate, Cytometry*, 53A:1-8; Heitmann et al., 2003, *Solution structure of the matrix attachment region-binding domain of chicken MeCP2, Eur. J. Biochem.*, 270:3263-3270; Hennerbichler et al., 2003, *Fetal nucleated red blood cells in peripheral blood of pregnant women: detection and determination of location on a slide using laser-scanning cytometry, Prenat Diagn.*, 23:710-5; Heymach et al., 2004, *Phase II study of the antiangiogenic agent SU5416 in patients with advanced soft tissue sarcomas, Clin Cancer Res.*, 10:5732-40; Hirabayashi et al., 2004, *The Wnt/{beta}-catenin pathway directs neuronal differentiation of cortical neural precursor cells, Development*, 131:2791-181; Huang et al., 2004, *Histone H2AX phosphorylation induced by selective photolysis of BrdU-labeled DNA with UV light: Relation to cell cycle phase, Cytometry*, 62A:1-7; Huang et al., 2004, *Assessment of histone H2AX phosphorylation induced by DNA topoisomerase I and II inhibitors topotecan and mitoxantrone and by the DNA cross-linking agent cisplatin, Cytometry*, 58A:99-110; Huang et al., 2003, *DNA Damage Induced by DNA Topoisomerase I- and Topoisomerase II Inhibitors Detected by H1stone H2AX Phosphorylation in Relation to the Cell Cycle Phase and Apoptosis, Cell Cycle*, 2:614-9; Isaka et al. 2003, *Chromosomal Variations Within Aneuploid Cancer Lines, J. Histochem. Cytochem.*, 51:1343-1353; Johnson et al., 2004, *Aluminum-Maltolate Induces Apoptosis and Necrosis in Neuro-2a Cells: Potential Role for p53 Signaling, Toxicol Sci.*, 83(2):329-39; Kamat et al., 2004, *The proteasome inhibitor bortezomib synergizes with gemcitabine to block the growth of human 253JB-V bladder tumors in vivo, Mol. Cancer Ther.*, 3:279-290; Kang et al. 2003, *Analysis of tyrosine phosphorylation in resident peritoneal cells during diet restriction by laser scanning cytometry, Shock*, 19:238-44; Kang et al., 2003, *Brief refeeding rapidly reverses dietary restriction-induced nuclear factor-kappaB downregulation in peritoneal resident cells, JPEN J Parenter Enteral Nutr,* 27:193-7 and discussion, 197; Kawamura et al., 2003, *Centrosome hyperamplification and chromosomal instability in bladder cancer,* Eur Urol. 43:505-15; Kawasaki et al., 2003, *11q23-24 loss is associated with chromosomal instability in endometrial cancer, Int J Mol Med.,* 12:727-31; Kobie et al., 2003, *Transforming Growth Factor {beta} Inhibits the Antigen-Presenting Functions and Antitumor Activity of Dendritic Cell Vaccines, Cancer Res.,* 63:1860-1864.; Kolek et al., 2003, *Antiproliferative and apoptotic effect of TGF-beta 1 in bovine mammary epithelial BME-UV1 cells, Comp Biochem Physiol C Toxicol Pharmacol.,* 134:417-30; Kolek et al., 2003, *Co-localization of apoptosis-regulating proteins in mouse mammary epithelial HC11 cells exposed to TGF-beta1, Eur J Cell Biol.,* 82:303-12; Kranc et al., 2003, *Transcriptional Coactivator Cited2 Induces Bmi1 and Mel18 and Controls Fibroblast Proliferation via Ink4a/ARF, Mol. Cell. Biol.,* 23:7658-7666; Kriaucionis and Bird, 2003, *DNA methylation and Rett syndrome, Hum. Mol. Genet.,* 12:221R-227R; Kulkarni et al., 2004, *Micropatterning of endothelial cells by guided stimulation with angiogenic factors, Biosens Bioelectron.,* 19:1401-7; Lamas et al., 2003, *Quantitative Fluorescence Imaging Approach for the Study of Polyploidization in Hepatocytes, J. Histochem. Cytochem.,* 51:319-330; Lima and Kultz, 2004, *Laser scanning cytometry and tissue microarray analysis of salinity effects on killifish chloride cells, J Exp Biol.,* 207:1729-39; Lin et al., 2004, *Evaluation of adipocyte apoptosis by laser scanning cytometry, Int J Obes Relat Metab Disord.,* 28:1535-40; Ma et al., 2003, *E2FBP1/DRIL1, an AT-Rich Interaction Domain-Family Transcription Factor, Is Regulated by p53, Mol. Cancer Res.,* 1:438-444; Maruvada et al., 2004, *Cell cycle-dependent expression of thyroid hormone receptor-{beta} is a mechanism for variable hormone sensitivity, Mol. Biol. Cell,* 15:1895-903; Masiuk et al., 2004, *Simultaneous measurement of nucleolin and estrogen receptor in breast cancer cells by laser scanning cytometry, Anticancer Res.,* 24:963-6; Mazur et al., 2003, *Induction of apoptosis in bone marrow cells after treatment of mice with WR-2721 and gamma-rays: relationship to the cell cycle, Cell Biol Toxicol.,* 19:13-27; Medina et al. 2003, *LAV694, a new antiproliferative agent showing improved skin tolerability vs. clinical standards for the treatment of actinic keratosis, Biochem Pharmacol.,* 66:1885-95; Megyeri et al., 2004, *Laser Scanning Cytometry for selection of green fluorescent protein transgenic mice using small number of blood cells, J Biochem Biophys Methods,* 61:183-7; Miyaji-Yamaguchi et al., 2003, *Involvement of Nucleocytoplasmic Shuttling of Yeast Nap1 in Mitotic Progression, Mol. Cell. Biol.,* 23:6672-6684; Mocellin et al., 2003, *Use of laser scanning cytometry to study tumor microenvironment, Histol Histopathol.,* 18:609-15; Moos et al., 2004, *Curcumin impairs tumor suppressor p53 function in colon cancer cells, Carcinogenesis,* 25:1611-7; Morales et al., 2003, *Role for the BRCA1 C-terminal Repeats (BRCT) Protein 53BP1 in Maintaining Genomic Stability, J. Biol. Chem.* 278:14971-14977.; Nawrocki et al. 2004, *The proteasome inhibitor bortezomib enhances the activity of docetaxel in orthotopic human pancreatic tumor xenografts, Mol. Cancer Ther.,* 3:59-70; Oleinik and Krupenko, 2003, *Ectopic Expression of 10-Formyltetrahydrofolate Dehydrogenase in A549 Cells Induces G1 Cell Cycle Arrest and Apoptosis, Mol. Cancer Res.,* 1:577-588; Oswald et al., 2004, *Mesenchymal Stem Cells Can Be Differentiated Into Endothelial Cells In Vitro, Stem Cells,* 22:377-384; Oswald et al., 2004, *Comparison of flow cytometry and laser scanning cytometry for the analysis of CD34+ hematopoietic stein cells, Cytometry,* 57A:100-7; Pfau et al., 2004, *Environmental oxygen tension affects phenotype in cultured bone marrow-derived macrophages, Am J Physiol Lung Cell Mol Physiol.,* 286:L354-62; Pina-Vaz et al., 2004, *Novel Method Using a Laser Scanning Cytometer for Detection of Mycobacteria in Clinical Samples, J. Clin. Microbiol.,* 42:906-908; Pozarowski at al., 2003, *Cell Cycle Effects and Caspase-Dependent and Independent Death of and Jurkat Cells Treated with the Inhibitor of NF-kappaB Parthenolide, Cell Cycle,* 2:377-83; Pozarowski et al., 2004, *Simple, semiautomatic assay of cytostatic and cytotoxic effects of antitumor drugs by laser scanning cytometry: Effects of the bis-intercalator WP631 on growth and cell cycle of T-24 cells, Cytometry,* 57A:113-9; Pullen et al., 2003, *The flame retardants tetrabromobisphenol A and tetrabromobisphenol A-bisallylether suppress the induction of interleukin-2 receptor alpha chain (CD25) in murine splenocytes, Toxicology,* 184:11-22; Reed et al., 2004, *Mutation of hCDC4 Leads to Cell Cycle Deregulation of Cyclin E in Cancer, Cancer Res.,* 64:795-800; Roth et al., 2003, *Effects of epithelial growth factor receptor (EGFR) kinase inhibitors on genetically reconstituted mouse mammary glands, Exp Toxicol Pathol.,* 55:237-45; Samaco et al., 2004, *Multiple pathways regulate MeCP2 expression in normal brain development and exhibit defects in autism-spectrum disorders, Hum. Mol. Genet.,* 13:629-39; Schumann et al., 2003, *Parenchymal, But Not Leukocyte, TNF Receptor 2 Mediates T Cell-Dependent Hepatitis in Mice, J. Immunol.,*

170:2129-2137; Schwartz et al., 2004, *Inhibition of experimental tobacco carcinogen induced head and neck carcinogenesis*, Oral Oncol., 40:611-23; Schwartz et al., 2003, *Oral cytology assessment by flow cytometry of DNA adducts, aneuploidy, proliferation and apoptosis shows differences between smokers and non-smokers*, Oral Oncol., 39:842-54; Shackney et al., 2004, *A suitable method for identifying cell aggregates in laser scanning cytometry listmode data for analyzing disaggregated cell suspensions obtained from human cancers*, Cytometry, 59B:10-23; Shackney et al., 2004, *Intracellular Patterns of Her-2/neu, ras, and Ploidy Abnormalities in Primary Human Breast Cancers Predict Postoperative Clinical Disease-Free Survival*, Clin. Cancer Res., 10:3042-3052; Shakhman et al., 2003, *Induction by {beta}-bungarotoxin of apoptosis in cultured hippocampal neurons is mediated by Ca2+-dependent formation of reactive oxygen species*, J. Neurochem., 87:598-608; Shibata et al., 2004, *Lovastatin inhibits tumor growth and lung metastasis in mouse mammary carcinoma model: a p53-independent mitochondrial-mediated apoptotic mechanism*. Carcinogenesis, 25:1887-98; Smith et al., 2003, *LFA-1-induced T cell migration on ICAM-1 involves regulation of MLCK-mediated attachment and ROCK-dependent detachment*, J. Cell Sci., 116:3123-3133; Smolewska et al., 2003, *Apoptosis of peripheral blood lymphocytes in patients with juvenile idiopathic arthritis*, Ann. Rheum. Dis., 62:761-763; Smolewski et al., 2003, *Caspase-mediated cell death in hematological malignancies: theoretical considerations, methods of assessment, and clinical implications*, Leuk Lymphoma, 44:1089-104; Strasberg Rieber et al. 2004, *Tumor apoptosis induced by ruthenium(II)-ketoconazole is enhanced in nonsusceptible carcinoma by monoclonal antibody to EGF receptor*, Int J Cancer, 112:376-84; Strife et al., 2003, *Direct Evidence That Bcr-Abl Tyrosine Kinase Activity Disrupts Normal Synergistic Interactions Between Kit Ligand and Cytokines in Primary Primitive Progenitor Cells*, Mol, Cancer Res., 1:176-185; Szodoray et al., 2003, *Programmed cell death in rheumatoid arthritis peripheral blood T-cell subpopulations determined by laser scanning cytometry*, Lab Invest., 83:1839-48; Takemoto et al., 2004, *Cell Cycle-dependent Phosphorylation, Nuclear Localization, and Activation of Human Condensin*, J. Biol. Chem., 279:4551-4559; Takita et al., 2003, *An analysis of changes in the expression of cyclins A and B1 by the cell array system during the cell cycle: Comparison between cell synchronization methods*, Cytometry, 55A:24-9; Tamamori-Adachi et al., 2003, *Critical Role of Cyclin D1 Nuclear Import in Cardiomyocyte Proliferation*, Circ. Res., 92:12e-19; Tamamori-Adachi et al., 2004, *Down-regulation of p27Kip1 promotes cell proliferation of rat neonatal cardiomyocytes induced by nuclear expression of cyclin D1 and CDK4. Evidence for impaired Skp2-dependent degradation of p27 in terminal differentiation*, J. Biol Chem., 279:50429-36; Valet et al., 2004, *Cytomics—new technologies: towards a human cytome project*. Cytometry, 59A:167-71; Vieyra et al., 2003, *Altered Subcellular Localization and Low Frequency of Mutations of ING1 in Human Brain Tumors*, Clin. Cancer Res., 9:5952-5961; Villamarin et al., 2003, *A comparative analysis of the time-dependent antiproliferative effects of daunorubicin and WP631*, Eur. J. Biochem., 270:764-770; Walker et al., 2003, *Phenotype versus Genotype in Gliomas Displaying Inter- or Intratumoral Histological Heterogeneity*, Clin. Cancer Res., 9:4841-4851; Wang et al., 2003, *Loss of 13q14-q21 and Gain of 5p14-pter in the Progression of Leiomyosarcoma*, Mod. Pathol., 16:778-785; Wang et al., 2003, *Genomic instability and endoreduplication triggered by RAD17 deletion*, Genes & Dev., 17:965-970; Williams et al., 2003, *Differential effects of the proteasome inhibitor bortezomib on apoptosis and angiogenesis in human prostate tumor xenografts*, Mol. Cancer Ther., 2:835-843; Wu et al., 2003, *Telomere dysfunction: a potential cancer predisposition factor*. J Natl Cancer Inst., 95:1211-8; Yellon et al., 2003, *The role of leukocyte traffic and activation in parturition*, J Soc Gynecol Investig., 10:323-38; Yuan et al., 2004, *The duration of nuclear extracellular signal-regulated kinase 1 and 2 signaling during cell cycle reentry distinguishes proliferation from apoptosis in response to asbestos*, Cancer Res., 64:6530-6, Zabaglo et al., 2003, *Measurement of proliferation marker Ki67 in breast tumour FNAs using laser scanning cytometry in comparison to conventional immunocytochemistry*. Cytometry, 56B:55-61; Zabaglo et al., 2003, *Cell filtration-laser scanning cytometry for the characterisation of circulating breast cancer cells*, Cytometry, 55A:102-108; Zhang et al., 2004, *From The Cover: High urea and NaCl carbonylate proteins in renal cells in culture and in vivo, and high urea causes 8-oxoguanine lesions in their DNA*, PNAS, 101:9491-9496; Zheng et al., 2004, *Calphostin-C induction of Vascular Smooth Muscle Cell Apoptosis Proceeds through Phospholipase D and Microtubule Inhibition*, J. Biol. Chem., 279:7112-18.

Many other assay methods are known or can be developed. Reagents appropriate for each reaction type will be provided in the sample and/or prepositioned in the reaction chamber. Exemplary reagents include antibodies, ligands, enzyme substrates, effectors and the like.

Exemplary Applications

The following prophetic examples are intended to illustrate aspects of the invention. However, these examples are for illustration only and are not intended to limit the invention in any fashion.

1. Detection and Characterization of Pathogens

The methods of the invention may be used for detection, identification and characterization of pathogens. There are many situations in which a sample contains a heterogeneous mixture of microorganisms (e.g., various bacterial species or strains, viruses, fungi) for which rapid detection and identification would be advantageous. For example, clinical (patient) samples often contain small numbers of microorganisms (e.g., bacteria, fungi) or viruses. Rapid characterization would permit earlier administration of appropriate drugs, if necessary. Similarly, the ability to rapidly detect and identify cellular and viral pathogens would be of value in the medical, veterinary, and agricultural fields, as well as in response to actual or suspected bioterrorism and for rapid detection water or food contaminants. In many cases a relatively small number of cells are available to work with, and, as noted, the cells are often available as a heterogeneous mixture with other cells.

In one illustrative embodiment, the method is used to determine whether a patient is infected with methicillin-resistance *S. aureus*. *S. aureus* can be identified using a bacteria-specific probe (e.g. to a rRNA gene). An methicillin resistant strain is distinguished from non-resistant strains based on a characteristic genetic sequence such as an open reading frame (gene or gene segment) or single polynucleotide polymorphism. A sample containing bacteria cells is obtained from a patient (e.g., a nose swab containing about 100 bacterial cells) and diluted into a reaction mixture containing nucleic acid primers and other reagents for amplification and detection of target sequences (e.g., PCR reagents, molecular beacons, polymerase, nucleotides, agents that lyse cells for nucleic acid release, etc.). Exemplary PCR primers are described in Huletsky et al., 2004, "New real-time PCR assay for rapid detection of methicillin-resistant *Staphylococcus aureus* directly from specimens containing a mixture of staphylococci." *J Clin Microbiol.* 42:1875-84. One primer/probe set in the reaction mixture emits a red fluorescence signal in the presence of a *S. aureus* target sequence found in both resistant and non-resistant stains while the second primer/probe set emits a green fluorescence signal only in the presence of a *S. aureus* target sequence found in the resistant strain. The cells are injected into a MPD and control channels actuated to create separate reaction chambers (e.g., a sample containing about 100 bacterial cells is partitioned into 2000 chambers) all or most of which contain zero or one cell. The device is placed on the thermocycler or amplification is otherwise initiated. Detection in a chamber of only a red signal indicates the presence in the sample of non-resistant *S. aureus*; detection in a chamber of both a red and green signal indicates the presence in the sample of drug resistant *S. aureus*; detection or no signal indicates no *S. aureus* bacteria are present in the sample.

2. Quantitation of Cells in a Population Having Specific Properties

In one aspect, the method is used for quantization of cells in a heterogeneous population having specific properties. For illustration, a cell population (e.g., peripheral blood mononuclear cells (PBMC)) containing cytotoxic T lymphocytes (CTL) (effector cells) can be partitioned and the ability of the cells to be stimulated by an antigen tested. The antigen reagent can be prepositioned in chambers or combined with cells immediately before partition. The proportion or type of cells activated in the presence can be assayed using any of a variety of assays for effector cell activation. For example, by performing in vitro stimulation after limiting dilution of circulating CTLs with the gag antigens of human immunodeficiency virus (HIV), the precursor population of gag-specific CTL can be quantitated and/or characterized. See, e.g., Koup "Limiting dilution analysis of cytotoxic T lymphocytes to human immunodeficiency virus gag antigens in infected persons: in vitro quantitation of effector cell populations with p17 and p24 specificities" *J Exp Med.* 1991 Dec. 1; 174(6): 1593-600.

3. Characterization of a Rare Cell in a Background of Other Cells

It is often advantageous to quantitate and/or characterize rare cells in a background of other cells. For example, in cancer, individual disseminated cancer cells may be found in blood. Further, biopsies may recover only a few malignant cells in a background of normal cells. The methods of the present invention allow the malignant cells to be isolated, identified based on a property (e.g., antigen, mutation or expression pattern) unique to the cancer cell, and then a different property of the cell determined.

In another example, nucleated fetal red blood cells are found at low levels in the blood of pregnant women and are a potential source of information about the fetal genome including any sequences associated with disease or propensity to disease. However, even enriched 10,000-fold fetal cells may be less than 0.1% of a sample making analysis by conventional methods difficult. Cells from a sample enriched for fetal NRBCs can be partitioned using the methods disclosed herein. Chambers containing fetal cells can be identified using a fetal-specific probe (e.g., a probe specific for the Y chromosome; abundance of RNA encoding fetal forms of hemoglobin) and assayed for several genetic characteristics using a multiplex assay. Other examples of rare cells in a background of different cells include, for example, a virally infected cell in a background of uninfected cells, a cell expressing a gene in a background of cells not expressing the gene; and the like.

In one embodiment, the MPD is used to partition a mixed population of cells to detect a property characteristic of a rare cell type in the population, i.e., cells comprising less than about 1%, more often less than about 0.1%, and very often less than about 0.01% of the cells in the population. There are many cases in which it advantageous to determine the properties of a rare cell in a population of other cells. The methods of the present invention enable analysis of a rare cell without background or interference for other cells. In general, the method involves partitioning cells and assaying individual cells for at least two properties at least one of which identifies the rare cell.

4. Expression Analysis of Individual Cells

In one embodiment the nucleic acid being analyzed is or includes RNA, and the expression level of specified genes in an individual cell is determined. Again using the example of a virus-infected cell, the expression profile for several host genes in a single cell can be correlated with the presence or absence of virus or with viral load. Gene expression profiles can also be correlated with cell identity (e.g., different expression profiles for different cells in a sample containing a heterogeneous mixture of cells) or cell response to a stimulus (e.g., the presence of a ligand that binds a cell receptor).

Because expression analysis typically involves a quantitative analysis, detection is typically achieved using one of the quantitative real time reverse transcriptase PCR methods described above. Thus, if a TaqMan approach is utilized, the reagents that are introduced (or previously spotted) in the reaction sites can include one or all of the following: primer, labeled probe, nucleotides and polymerase. Another approach is Ribo-SPIA (see above).

While the present invention has been described with reference to the specific embodiments thereof, it should be understood by those skilled in the art that various changes can be made and equivalents can be substituted without departing from the scope of the invention. In addition, many modifications can be made to adapt a particular situation, material, composition of matter, process, process step or steps, to achieve the benefits provided by the present invention without departing from the scope of the present invention. All such modifications are intended to be within the scope of the claims appended hereto.

All publications and patent documents cited herein are incorporated herein by reference as if each such publication or document was specifically and individually indicated to be incorporated herein by reference. Citation of publications and patent documents is not intended as an indication that any such document is pertinent prior art, nor does it constitute any admission as to the contents or date of the same.

The invention claimed is:

1. An assay method comprising
   (a) using a microfluidic device to distribute a sample into a plurality of sub-samples, wherein each sub-sample is distributed into a reaction site by the action of flow channels, control channels and valves:
      (i) said sample comprises a rare cell in a background of other cells, wherein the rare cell is less than 1% of the cells in the sample, and
      (ii) at least two sub-samples comprise exactly one cell each, one of which is said rare cell;
   (b) providing the same reagents in each sub-sample;
   (c) conducting a reaction in each sub-sample; and
   (d) analyzing the results of each reaction to detect at least two properties of a cell, at least one of which identifies the rare cell, wherein at least one cell analyzed comprises said rare cell.

2. The method of claim 1 wherein the sample is partitioned into 100-100,000 sub-samples.

3. The method of claim 1, wherein said analyzing comprises detecting a nucleic acid molecule.

4. The method of claim 3, wherein said nucleic acid molecule comprises RNA.

5. The method of claim 3, wherein said analyzing comprises detecting said nucleic acid molecule by amplification.

6. The method of claim 5, wherein said amplification is by PCR or RT-PCR.

7. The method of claim 1, wherein at least 99% of the sub-samples contain zero or one cell.

8. The method of claim 1, wherein the cells are bacterial cells.

9. The method of claim 1 wherein at least one property is the presence or absence in the cell of a nucleic acid having a specified sequence.

10. The method of claim 1 wherein at least one property is other than the presence or absence in the cell of a nucleic acid having a specified sequence.

11. The method of claim 3, wherein said analyzing comprises determining the nucleic acid sequence of the nucleic acid molecule.

12. The method of claim 3, wherein said analyzing comprises single nucleotide polymorphism analysis.

13. The method of claim 3, wherein said analyzing comprises quantification of the nucleic acid molecule.

14. The method of claim 1, wherein the analyzing comprises detecting the presence of absence of a protein or epitope in the cell or on the cell surface.

15. The method of claim 1, wherein said analyzing comprises detecting secretion of a protein or non-protein molecule by the cell.

16. The method of claim 1, wherein said analyzing comprises detecting a metabolic reaction or change in cell metabolism.

17. The method of claim 1, wherein at least one cell analyzed comprises a fetal cell.

18. The method of claim 1, wherein at least one cell analyzed comprises a cancer cell.

19. The method of claim 18, wherein the cancer cell is a disseminated cancer cell obtained from blood.

20. The method of claim 1, wherein the sample comprises peripheral blood mononuclear cells (PBMC).

21. The method of claim 1, wherein the rare cell is less than 0.1% of the cells in the sample.

22. The method of claim 1, wherein the rare cell is less than 0.01% of the cells in the sample.

* * * * *